(12) United States Patent
Fernandez Farres et al.

(10) Patent No.: US 11,696,596 B2
(45) Date of Patent: Jul. 11, 2023

(54) PROCESS FOR THE PREPARATION OF PICKERING EMULSION FORMING PARTICLES BY DERIVATIZATION OF CELLULOSE-RICH DIETARY FIBERS WITH ENZYMES AND EMULSIONS PREPARED

(71) Applicant: SOCIETE DES PRODUITS NESTLE S.A., Vevey (CH)

(72) Inventors: Isabel Fernandez Farres, Lausanne (CH); Zeynel Deniz Gunes, Lausanne (CH); Christina Vafeiadi, Lausanne (CH); Lionel Jean Rene Bovetto, Lucens (CH); Anna Mosior, Bern (CH)

(73) Assignee: Societe des Produits Nestle S.A., Vevey (CH)

(*) Notice: Subject to any disclaimer, the term of this patent is extended or adjusted under 35 U.S.C. 154(b) by 210 days.

(21) Appl. No.: 16/954,812

(22) PCT Filed: Dec. 19, 2018

(86) PCT No.: PCT/EP2018/085741
§ 371 (c)(1),
(2) Date: Jun. 17, 2020

(87) PCT Pub. No.: WO2019/121852
PCT Pub. Date: Jun. 27, 2019

(65) Prior Publication Data
US 2021/0204584 A1    Jul. 8, 2021

(30) Foreign Application Priority Data
Dec. 20, 2017  (EP) .................................. 17209097

(51) Int. Cl.
| | | |
|---|---|---|
| A23L 33/21 | (2016.01) | |
| C08L 1/02 | (2006.01) | |
| C12P 19/14 | (2006.01) | |
| C12N 9/24 | (2006.01) | |
| A23L 33/18 | (2016.01) | |
| C08L 5/06 | (2006.01) | |

(52) U.S. Cl.
CPC ................. *A23L 33/18* (2016.08); *C08L 1/02* (2013.01); *C08L 5/06* (2013.01); *C12P 19/14* (2013.01)

(58) Field of Classification Search
CPC .................................. C08L 1/02; C12P 19/14
See application file for complete search history.

(56) References Cited

U.S. PATENT DOCUMENTS 5,266,473 A * 11/1993 Nielsen ..................... A23L 5/25
   435/219
2009/0311376 A1 * 12/2009 Rao ......................... A23L 7/115
   426/28

FOREIGN PATENT DOCUMENTS

JP            265137       * 9/2003

OTHER PUBLICATIONS

Kato et al. "Protein Flexibility and Functional Properties of Heat-denatured Ovalbumin and Zysozyme" Agric. Biol. Chem., 1986, vol. 50, No. 2, pp. 417-420.
Karunasawat et al. "Effect of depolymerized mango pulp as a stabilizer in, oil-in-water emulsion containing sodium caseinate" Food and Bioproducts Processing, 2010, vol. 88, pp. 202-208.
Dickinson, Eric "Biopolymer-based particles as stabilizing agents for emulsions and foams" Food Hydrocolloids, 2017, vol. 68, pp. 219-231.
Xu et al. "Impact of whey protein—Beet pectin conjugation on the physicochemical stability of beta-carotene emulsions" Food Hydrocolloids, 2012, vol. 28, pp. 258-266.
Tamayo Tenorio et al. "Interfacial properties of green leaf cellullosic particles" Food Hydrocolloids, 2017, vol. 71, pp. 8-16.

* cited by examiner

*Primary Examiner* — Maryam Monshipouri
(74) *Attorney, Agent, or Firm* — K&L Gates LLP

(57) ABSTRACT

The present invention relates to a process for forming a functionalised dietary fibre comprising admixing an enzyme and an aqueous suspension of dietary fibre, wherein said dietary fibre is at a $D_{50}$ particle size distribution of less than 30 microns after degradation by the enzyme and comprises less than 25 wt. % soluble fibres and at least 40% wt. % cellulose; denaturing said enzyme to form a functionalised, amphiphilic dietary fibre with adsorbed enzyme. The present invention further relates to a Pickering particle comprising a functionalised dietary fibre and denatured enzyme and the use of the functionalised dietary fibre and denatured enzyme according to present invention or the Pickering particle according to the present invention to stabilize an emulsion.

4 Claims, 28 Drawing Sheets
Specification includes a Sequence Listing.

Scale bar: 100μm     Scale bar: 50μm     Scale bar: 50μm

FIG. 28A

SEQ ID No. 1

```
Met Ile Val Gly Ile Leu Thr Thr Leu Ala Thr Leu Ala Thr Leu Ala
1               5                   10                  15
Ala Ser Val Pro Leu Glu Glu Arg Gln Ala Cys Ser Ser Val Trp Gly
                20                  25                  30
Gln Cys Gly Gly Gln Asn Trp Ser Gly Pro Thr Cys Cys Ala Ser Gly
                35                  40                  45
Ser Thr Cys Val Tyr Ser Asn Asp Tyr Tyr Ser Gln Cys Leu Pro Gly
            50                  55                  60
Ala Ala Ser Ser Ser Ser Ser Thr Arg Ala Ala Ser Thr Thr Ser Arg
65                  70                  75                  80
Val Ser Pro Thr Thr Ser Arg Ser Ser Ser Ala Thr Pro Pro Pro Gly
                85                  90                  95
Ser Thr Thr Thr Arg Val Pro Pro Val Gly Ser Gly Thr Ala Thr Tyr
                100                 105                 110
Ser Gly Asn Pro Phe Val Gly Val Thr Pro Trp Ala Asn Ala Tyr Tyr
                115                 120                 125
Ala Ser Glu Val Ser Ser Leu Ala Ile Pro Ser Leu Thr Gly Ala Met
                130                 135                 140
Ala Thr Ala Ala Ala Ala Val Ala Lys Val Pro Ser Phe Met Trp Leu
145                 150                 155                 160
Asp Thr Leu Asp Lys Thr Pro Leu Met Glu Gln Thr Leu Ala Asp Ile
                165                 170                 175
```

FIG. 28B

```
Arg Thr Ala Asn Lys Asn Gly Gly Asn Tyr Ala Gly Gln Phe Val Val
                180                 185                 190
Tyr Asp Leu Pro Asp Arg Asp Cys Ala Ala Leu Ala Ser Asn Gly Glu
                195                 200                 205
Tyr Ser Ile Ala Asp Gly Gly Val Ala Lys Tyr Lys Asn Tyr Ile Asp
            210                 215                 220
Thr Ile Arg Gln Ile Val Glu Tyr Ser Asp Ile Arg Thr Leu Leu
225                 230                 235                 240
Val Ile Glu Pro Asp Ser Leu Ala Asn Leu Val Thr Asn Leu Gly Thr
                245                 250                 255
Pro Lys Cys Ala Asn Ala Gln Ser Ala Tyr Leu Glu Cys Ile Asn Tyr
                260                 265                 270
Ala Val Thr Gln Leu Asn Leu Pro Asn Val Ala Met Tyr Leu Asp Ala
                275                 280                 285
Gly His Ala Gly Trp Leu Gly Trp Pro Ala Asn Gln Asp Pro Ala Ala
                290                 295                 300
Gln Leu Phe Ala Asn Val Tyr Lys Asn Ala Ser Ser Pro Arg Ala Leu
305                 310                 315                 320
Arg Gly Leu Ala Thr Asn Val Ala Asn Tyr Asn Gly Trp Asn Ile Thr
                325                 330                 335
Ser Pro Pro Ser Tyr Thr Gln Gly Asn Ala Val Tyr Asn Glu Lys Leu
                340                 345                 350
Tyr Ile His Ala Ile Gly Arg Leu Leu Ala Asn His Gly Trp Ser Asn
                355                 360                 365
Ala Phe Phe Ile Thr Asp Gln Gly Arg Ser Gly Lys Gln Pro Thr Gly
                370                 375                 380
Gln Gln Gln Trp Gly Asp Trp Cys Asn Val Ile Gly Thr Gly Phe Gly
```

FIG. 28C

```
385                         390                         395                         400
Ile Arg Pro Ser Ala Asn Thr Gly Asp Ser Leu Leu Asp Ser Phe Val
                    405                         410                         415
Trp Val Lys Pro Gly Gly Glu Cys Asp Gly Thr Ser Asp Ser Ser Ala
                    420                         425                         430
Pro Arg Phe Asp Ser His Cys Ala Leu Pro Asp Ala Leu Gln Pro Ala
                    435                         440                         445
Pro Gln Ala Gly Ala Trp Phe Gln Ala Tyr Phe Val Gln Leu Leu Thr
        450                         455                         460
Asn Ala Asn Pro Ser Phe Leu
465                 470
```

FIG. 29A

SEQ ID No. 2

```
Met Tyr Arg Lys Leu Ala Val Ile Ser Ala Phe Leu Ala Thr Ala Arg
1               5                   10                  15
Ala Gln Ser Ala Cys Thr Leu Gln Ser Glu Thr His Pro Pro Leu Thr
                20                  25                  30
Trp Gln Lys Cys Ser Ser Gly Gly Thr Cys Thr Gln Gln Thr Gly Ser
                35                  40                  45
Val Val Ile Asp Ala Asn Trp Arg Trp Thr His Ala Thr Asn Ser Ser
            50                  55                  60
Thr Asn Cys Tyr Asp Gly Asn Thr Trp Ser Ser Thr Leu Cys Pro Asp
65                  70                  75                  80
Asn Glu Thr Cys Ala Lys Asn Cys Cys Leu Asp Gly Ala Ala Tyr Ala
                    85                  90                  95
Ser Thr Tyr Gly Val Thr Thr Ser Gly Asn Ser Leu Ser Ile Gly Phe
                100                 105                 110
Val Thr Gln Ser Ala Gln Lys Asn Val Gly Ala Arg Leu Tyr Leu Met
                115                 120                 125
Ala Ser Asp Thr Thr Tyr Gln Glu Phe Thr Leu Leu Gly Asn Glu Phe
                130                 135                 140
Ser Phe Asp Val Asp Val Ser Gln Leu Pro Cys Gly Leu Asn Gly Ala
145                 150                 155                 160
Leu Tyr Phe Val Ser Met Asp Ala Asp Gly Gly Val Ser Lys Tyr Pro
                165                 170                 175
Thr Asn Thr Ala Gly Ala Lys Tyr Gly Thr Gly Tyr Cys Asp Ser Gln
```

FIG. 29B

```
              180                       185                       190
Cys Pro Arg Asp Leu Lys Phe Ile Asn Gly Gln Ala Asn Val Glu Gly
              195                       200                       205
Trp Glu Pro Ser Ser Asn Asn Ala Asn Thr Gly Ile Gly Gly His Gly
              210                       215                       220
Ser Cys Cys Ser Glu Met Asp Ile Trp Glu Ala Asn Ser Ile Ser Glu
225                       230                       235                       240
Ala Leu Thr Pro His Pro Cys Thr Thr Val Gly Gln Glu Ile Cys Glu
              245                       250                       255
Gly Asp Gly Cys Gly Gly Thr Tyr Ser Asp Asn Arg Tyr Gly Gly Thr
              260                       265                       270
Cys Asp Pro Asp Gly Cys Asp Trp Asn Pro Tyr Arg Leu Gly Asn Thr
              275                       280                       285
Ser Phe Tyr Gly Pro Gly Ser Ser Phe Thr Leu Asp Thr Thr Lys Lys
              290                       295                       300
Leu Thr Val Val Thr Gln Phe Glu Thr Ser Gly Ala Ile Asn Arg Tyr
305                       310                       315                       320
Tyr Val Gln Asn Gly Val Thr Phe Gln Gln Pro Asn Ala Glu Leu Gly
              325                       330                       335
Ser Tyr Ser Gly Asn Glu Leu Asn Asp Asp Tyr Cys Thr Ala Glu Glu
              340                       345                       350
Ala Glu Phe Gly Gly Ser Ser Phe Ser Asp Lys Gly Gly Leu Thr Gln
              355                       360                       365
Phe Lys Lys Ala Thr Ser Gly Gly Met Val Leu Val Met Ser Leu Trp
              370                       375                       380
Asp Asp Tyr Tyr Ala Asn Met Leu Trp Leu Asp Ser Thr Tyr Pro Thr
385                       390                       395                       400
```

FIG. 29C

```
Asn Glu Thr Ser Ser Thr Pro Gly Ala Val Arg Gly Ser Cys Ser Thr
                405                 410                 415
Ser Ser Gly Val Pro Ala Gln Val Glu Ser Gln Ser Pro Asn Ala Lys
            420                 425                 430
Val Thr Phe Ser Asn Ile Lys Phe Gly Pro Ile Gly Ser Thr Gly Asn
        435                 440                 445
Pro Ser Gly Gly Asn Pro Pro Gly Gly Asn Arg Gly Thr Thr Thr Thr
    450                 455                 460
Arg Arg Pro Ala Thr Thr Thr Gly Ser Ser Pro Gly Pro Thr Gln Ser
465                 470                 475                 480
His Tyr Gly Gln Cys Gly Gly Ile Gly Tyr Ser Gly Pro Thr Val Cys
                485                 490                 495
Ala Ser Gly Thr Thr Cys Gln Val Leu Asn Pro Tyr Tyr Ser Gln Cys
            500                 505                 510
Leu
```

FIG. 30A

SEQ ID No. 3

```
Ala Thr Thr Cys Thr Phe Ser Gly Ser Asn Gly Ala Ser Ser Ala Ser
1               5                   10                  15
Lys Ser Lys Thr Ser Cys Ser Thr Ile Val Leu Ser Asn Val Ala Val
            20                  25                  30
Pro Ser Gly Thr Thr Leu Asp Leu Thr Lys Leu Asn Asp Gly Thr His
            35                  40                  45
Val Ile Phe Ser Gly Glu Thr Thr Phe Gly Tyr Lys Glu Trp Ser Gly
    50                  55                  60
Pro Leu Ile Ser Val Ser Gly Ser Asp Leu Thr Ile Thr Gly Ala Ser
65                  70                  75                  80
Gly His Ser Ile Asn Gly Asp Gly Ser Arg Trp Trp Asp Gly Glu Gly
                85                  90                  95
Gly Asn Gly Gly Lys Thr Lys Pro Lys Phe Phe Ala Ala His Ser Leu
            100                 105                 110
Thr Asn Ser Val Ile Ser Gly Leu Lys Ile Val Asn Ser Pro Val Gln
            115                 120                 125
Val Phe Ser Val Ala Gly Ser Asp Tyr Leu Thr Leu Lys Asp Ile Thr
    130                 135                 140
Ile Asp Asn Ser Asp Gly Asp Asn Gly Gly His Asn Thr Asp Ala
145                 150                 155                 160
Phe Asp Ile Gly Thr Ser Thr Tyr Val Thr Ile Ser Gly Ala Thr Val
                165                 170                 175
Tyr Asn Gln Asp Asp Cys Val Ala Val Asn Ser Gly Glu Asn Ile Tyr
            180                 185                 190
```

FIG. 30B

```
Phe Ser Gly Gly Tyr Cys Ser Gly Gly His Gly Leu Ser Ile Gly Ser
            195                 200                 205
Val Gly Gly Arg Ser Asp Asn Thr Val Lys Asn Val Thr Phe Val Asp
            210                 215                 220
Ser Thr Ile Ile Asn Ser Asp Asn Gly Val Arg Ile Lys Thr Asn Ile
225                 230                 235                 240
Asp Thr Thr Gly Ser Val Ser Asp Val Thr Tyr Lys Asp Ile Thr Leu
            245                 250                 255
Thr Ser Ile Ala Lys Tyr Gly Ile Val Val Gln Gln Asn Tyr Gly Asp
            260                 265                 270
Thr Ser Ser Thr Pro Thr Thr Gly Val Pro Ile Thr Asp Phe Val Leu
            275                 280                 285
Asp Asn Val His Gly Ser Val Val Ser Ser Gly Thr Asn Ile Leu Ile
            290                 295                 300
Ser Cys Gly Ser Gly Ser Cys Ser Asp Trp Thr Trp Thr Asp Val Ser
305                 310                 315                 320
Val Ser Gly Gly Lys Thr Ser Ser Lys Cys Thr Asn Val Pro Ser Gly
            325                 330                 335
Ala Ser Cys
```

PROCESS FOR THE PREPARATION OF PICKERING EMULSION FORMING PARTICLES BY DERIVATIZATION OF CELLULOSE-RICH DIETARY FIBERS WITH ENZYMES AND EMULSIONS PREPARED

CROSS REFERENCE TO RELATED APPLICATIONS

The present application is a National Stage of International Application No. PCT/EP2018/085741, filed on Dec. 19, 2018, which claims priority to European Patent Application No. 17209097.9, filed on Dec. 20, 2017, the entire contents of which are being incorporated herein by reference.

FIELD OF THE INVENTION

The present invention relates to a process for forming a functionalized dietary fibre. The present invention further relates to compositions comprising a functionlised dietary fibre and denatured enzyme. The present invention further relates to Pickering particles. The present invention further relates to use of functionlised dietary fibre and denatured enzyme or to a Pickering particle of the present invention to stabilize emulsions and to an emulsion or product comprising same.

BACKGROUND

Plant cell walls, which are the main source of dietary fibre, are composed of a primary and a secondary layer that consist of different macromolecules forming a complex network (McDougall et al. 1996 Processing and Function. *Journal of the Science of Food and Agriculture*, 70(2), pp. 133-150). The primary walls from higher plants largely consist of polysaccharides (up to 90% w/w of dm), most of which are resistant to enzymatic breakdown in the human gut, hence termed dietary fibre. The remaining components are relatively small proportions of structural glycoproteins (2-10%), phenolic esters (<2%), minerals (1-5%) and enzymes.

Cellulose represents the main cell wall polysaccharide. In general, cellulose is a water-insoluble homopolymer consisting of a linear chain of repeating ß-1,4-glucosyl units. Individual celluloses chains are tightly bundled together into microfibrils and are held together by hydrogen bonding. Cellulose can vary in the ratio of amorphous and crystalline regions, of which the latter is very resistant to hydrolysis.

Pectins are a diverse group of polysaccharides and have the most complex structures (Vincken, Voragen and Beldman, 2003 Enzymes degrading rhamnogalacturonan and xylogalacturonan. In: J. Whitaker, A. Voragen and D. Wong, ed., Handbook of food enzymology, 1st ed. New York: Marcel Dekker, pp. 930-941). Structures that belong to this group are: homogalacturonan, rhamnogalacturonan 1 and 2, xylogalacturonan, arabinan, arabinogalactan 1 and 2 (Bonnin, Garnier, & Ralet, 2014 *Applied Microbiology and Biotechnology*, 98(2), pp. 519-532). Depending on the plant or plant fraction the type of pectin may differ.

SUMMARY OF THE INVENTION

According to a first aspect the present invention provides a process for forming a functionalised dietary fibre comprising admixing an enzyme and an aqueous suspension of dietary fibre, wherein said dietary fibre is at a D90 particle size distribution of less than 800 microns, suitably less than 500 microns, and comprises less than 25 wt. % soluble fibres and at least 40% wt. % cellulose, wherein said enzyme is capable of degrading the dietary fibre; denaturing said enzyme to form an aqueous suspension comprising a functionalised dietary fibre and denatured enzyme.

According to a further aspect the present invention provides a process for forming a functionalised dietary fibre comprising admixing an enzyme and an aqueous suspension of dietary fibre, wherein said dietary fibre is at a $D_{50}$ particle size distribution of less than 30 microns after degradation by the enzyme, and comprises less than 25 wt. % soluble fibres and at least 40% wt. % cellulose; denaturing said enzyme to form a functionalised, amphiphilic dietary fibre with adsorbed enzyme.

According to a further aspect of the present invention there is provided a functionalised dietary fibre and denatured enzyme obtainable or obtained by the process according to the present invention.

In a further aspect, the present invention provides a Pickering particle comprising a functionalised dietary fibre and denatured enzyme.

In one aspect of the present invention, there is provided use of the functionalised dietary fibre and denatured enzyme according to the present invention or of the Pickering particle according to the present invention to stabilize a water-in-oil emulsion or an oil-in-water emulsion.

The present invention yet further provides an oil-in-water emulsion or water-in-oil emulsion comprising the functionalised dietary fibre and denatured enzyme according to the present invention or the Pickering particle according to the present invention.

The present invention further provides a food product or a cosmetic product or a skin care product or a pharmaceutical product or a personal hygiene product or a hairstyling product comprising (e.g. stabilised by) the functionalised dietary fibre and denatured enzyme according to the present invention or the Pickering particle according to the present invention.

BRIEF DESCRIPTION OF THE DRAWINGS

Embodiments of the invention will now be described, by way of example only, with reference to accompanying drawings, in which:

FIGS. 28A-C shows SEQ ID No. 1 a polypeptide sequence for a cellobiohydrolase obtainable from *Trichoderma reesei*

FIGS. 29A-C shows SEQ ID No. 2 a polypeptide sequence for a cellobiohydrolase obtainable from *Trichoderma reesei*

FIGS. 30A-B shows SEQ ID No. 3 a polypeptide sequence for a polygalacturonase obtainable from *Aspergillus aculeatus.*

DETAILED DESCRIPTION

Figure 1:
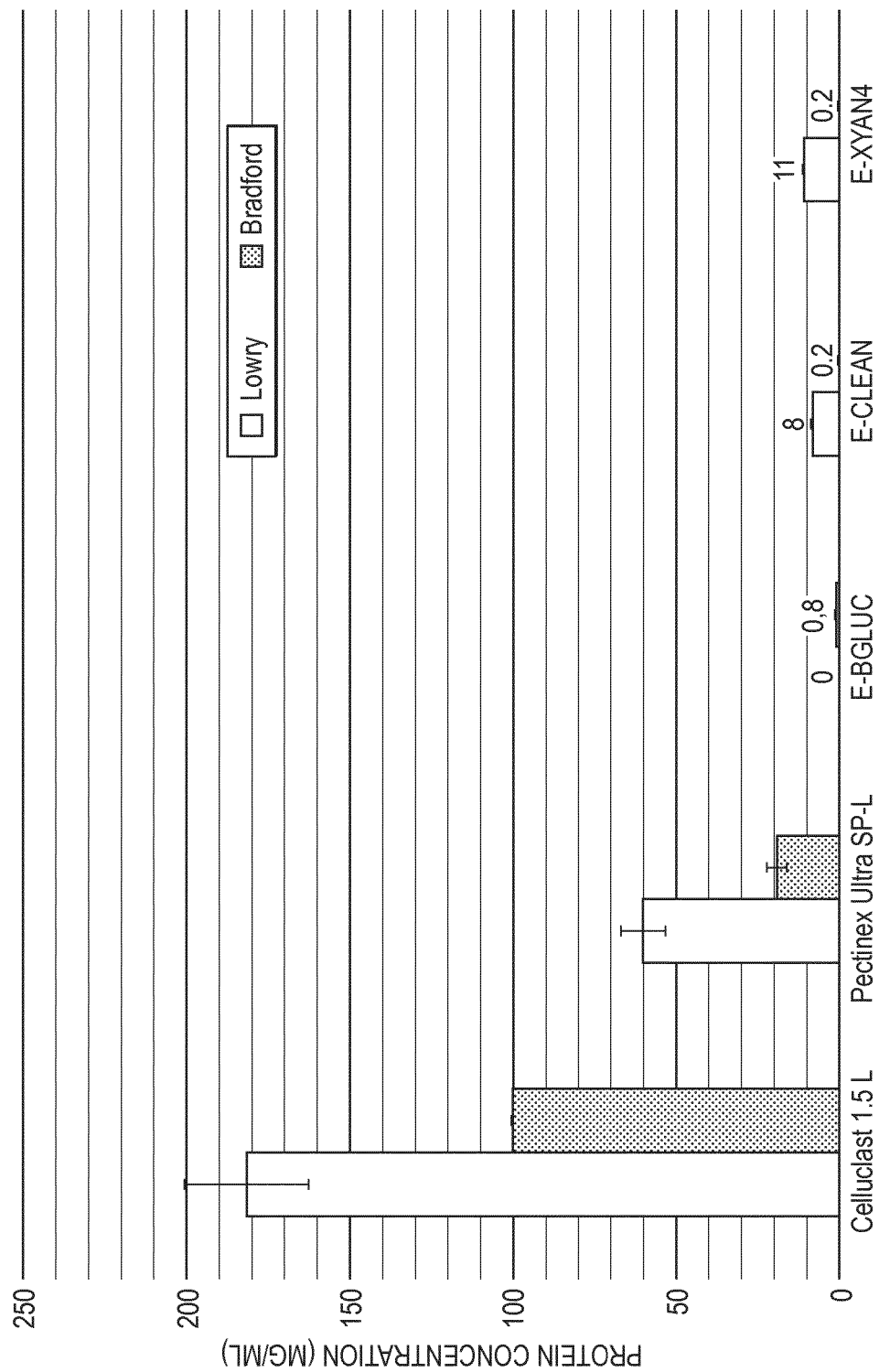
FIG. 1 shows the Protein content of purified enzymes and commercial enzyme cocktails measured with Bradford and Lowry method.

A seminal finding of the present invention is that treatment of dietary fibre, which is high in cellulose and low in soluble fibres, with an enzyme capable of degrading dietary fibre results in a composition comprising a functionalised dietary fibre and denatured enzyme which can be used to stabilise an emulsion.

For the first time the present inventors have shown that a functionalised dietary fibre and denatured enzyme according to the present invention acts as a Pickering particle.

Based on these findings, we provide a process for forming a functionalised dietary fibre comprising admixing an enzyme and an aqueous suspension of dietary fibre, wherein said dietary fibre is at a D90 particle size distribution of less than 800 microns, suitably less than 500 microns, and comprises less than 25 wt. % soluble fibres and at least 40% wt. % cellulose, wherein said enzyme is capable of degrading the dietary fibre; denaturing said enzyme to form an aqueous suspension comprising a functionalised dietary fibre and denatured enzyme.

In one embodiment the functionalised dietary fibre and denatured enzyme form interactions between the denatured enzyme and the functionalised dietary fibre which results in the formation of Pickering particles. The enzyme of the present invention may have affinity for the fibre as a substrate (and so bind onto it). Enzyme degradation of the dietary fibre may suitably reduce its particle size. The enzyme for use in the present invention is capable of degrading the dietary fibre. Functionalised dietary fibre (e.g. dietary fibre particles) in combination with a denatured enzyme(s) exhibit surface-activity and act as Pickering particles. The functionalised dietary fibre particles and denatured enzyme(s) may form functionalised enzyme-complexed dietary fibre. The functionalised enzyme-complexed dietary fibre according to the present invention may act as Pickering particles. The enzyme(s) may remain attached to the functionalised dietary fibre surface serving as a proteinaceous structural component that anchors the particle to the oil/water or water/oil interface.

Without wishing to be bound by theory, the emulsion stabilization properties of dietary fibre, e.g. PHF, can be improved by reducing particle size and inducing amphiphilicity of any part of the fibre/particle which may be exposed to water (including the particle surface and internal regions of the particle which are exposed to water) using one or more enzymes with fibre degrading activities. Inducing amphiphilicity may increase the average wetting property of the particle. Without wishing to be bound by theory the purpose of the enzymatic treatment may be to modify the particle surface (e.g. the part of the particle that may be exposed to water) amphiphilicity and size by disrupting the fibre network such that hydrophobic groups become exposed at the particle surface. This can be achieved by exposing crystalline cellulose structures, using enzymes that degrade the disordered amorphous part of the cellulose or by exposing hydrophobic groups present on the pectin backbone (methyl-, acetyl- and ferulic acid esters). In addition, structural proteins associated with the dietary fibre may contribute to an enhanced surface activity of the functionlised dietary fibre.

In some embodiments the dietary fibre may not be degraded or hydrolysed by the enzyme. However, the enzyme should be one which is capable of hydrolysing the dietary fibre. An enzyme which is capable of hydrolysing the dietary fibre is an enzyme which has an affinity for the dietary fibre as a substrate and so which binds to the dietary fibre.

In one embodiment the enzyme is an enzyme which hydrolyses the dietary fibre.

In one embodiment the dietary fibre may be hydrolysed with said one or more enzymes for a period up to 24 hours.

In one embodiment the dietary fibre may be hydrolysed for between about 10 minutes and about 24 hours. In some embodiments the dietary fibre may be hydrolysed for between about 30 minutes to 20 hours, suitably 4 hours to 20 hours, suitably 14 hours to 20 hours.

In some embodiments the dietary fibre may be hydrolysed for between about 6 and about 24 hours. In some embodiments the dietary fibre may be hydrolysed for between 4-10 hours.

In some embodiments the dietary fibre may be hydrolysed for less than about 8 hours e.g. in order to reduce the secondary hydrolysis that can occur thereafter.

In some embodiments the dietary fibre may be hydrolysed for at least 30 minutes, e.g. at least 1 hour, or at least 4 h or at least 6 hours or at least 10 h or at least 15 h.

In some embodiments the dietary fibre may be hydrolysed for about 16 h.

In one embodiment the enzyme hydrolysis may hydrolyse polysaccharide components to oligosaccharides, but may avoid complete breakdown of the oligosaccharides to monosaccharides. In some embodiments the process is continued until approximately 35-50% of the polysaccharides or 35-50% of the cellulose is degraded to monosaccharides, suitably until approximately 40-48% of the polysaccharides or 40-48% of the cellulose is degraded to monosaccharides.

Conditions for hydrolysis will be optimum conditions for the specific enzyme being used. These are typically indicated when purchasing the enzyme, or determined experimentally. Suitably the hydrolysis may be carried out at the optimum pH for the enzyme(s) used. Suitably the hydrolysis may be carried out at a pH of between 5 and 8. Suitably the hydrolysis may be carried out at the optimum temperature for the enzyme(s) used. Suitably the hydrolysis may be carried out at a temperature between 45 and 65° C. Suitably the hydrolysis may be carried out with continuous stirring.

Suitably the enzyme treatment of the dietary fibre reduces the particle size. In other words the particle size of the functionalised dietary fibre is smaller than that of the dietary fibre before treatment. In some embodiments enzyme treatment may reduce the mean volume diameter of the dietary fibre by a factor of about ten.

The dietary fibre (e.g. before treatment) suitably has a D90 particle size distribution of less than 800 μm.

The dietary fibre (e.g. before treatment or after treatment) suitably has a D90 particle size distribution of less than 500 μm.

In one embodiment the dietary fibre (e.g. before treatment or after treatment) may have a D90 particle size distribution of less than 30 μm.

In one embodiment the dietary fibre (e.g. before treatment or after treatment) may have a D90 particle size distribution of less than 10 μm.

In one embodiment the dietary fibre (e.g. before treatment of after treatment) may have a D90 particle size distribution of less than 3 μm.

The dietary fibre (e.g. starting dietary fibre before treatment) may be milled to a suitable D90 particle size distribution, e.g. of less than 800 μm, or less than 500 μm, or less than 30 μm, or less than 10 μm or less than 3 μm by any suitable means. One suitable means may be jet milling. By way of example the dietary fibre may be milled in an IKA M20 batch mill (Milian, Switzerland) at a constant speed of 2000×g for 10 seconds.

In one embodiment the milling of the dietary fibre may occur before enzyme treatment.

In one embodiment the milling of the dietary fibre may occur after enzyme treatment, e.g. after drying said aqueous suspension.

In one embodiment the milling of the dietary fibre may occur both before and after enzyme treatment.

When the milling of the dietary fibre occurs, preferably the dietary fibre is in a relatively dry state.

The present invention further provides a process for forming a functionalised dietary fibre comprising admixing an enzyme and an aqueous suspension of dietary fibre, wherein said dietary fibre is at a D50 particle size distribution of less than 30 microns after degradation by the enzyme, and comprises less than 25 wt. % soluble fibres and at least 40% wt. % cellulose; denaturing said enzyme to form a functional amphiphilic dietary fibre with adsorbed enzyme. Functionalised dietary fibre (e.g. dietary fibre particles) in combination with a denatured enzyme(s) exhibit surface-activity and act as Pickering particles. The enzyme(s) may remain attached to the functionalised dietary fibre surface serving as a proteinaceous structural component that anchors the particle to the oil/water or water/oil interface.

Without wishing to be bound by theory, the emulsion stabilization properties of dietary fibre, e.g. PHF, can be improved by reducing particle size and inducing amphiphilicity of any part of the fibre/particle which may be exposed to water (including the particle surface and internal regions of the particle which are exposed to water) using one or more enzymes with fibre degrading activities. Inducing amphiphilicity may increase the average wetting property of the particle. Without wishing to be bound by theory the purpose of the enzymatic treatment may be to modify the particle surface (e.g. the part of the particle that may be exposed to water) amphiphilicity and size by disrupting the fibre network such that hydrophobic groups become exposed at the particle surface. This can be achieved by exposing crystalline cellulose structures, using enzymes that degrade the disordered amorphous part of the cellulose or by exposing hydrophobic groups present on the pectin backbone (methyl-, acetyl- and ferulic acid esters). In addition, structural proteins associated with the dietary fibre may contribute to an enhanced surface activity of the functionlised dietary fibre.

The dietary fibre is degraded or hydrolysed by the enzyme. An enzyme which hydrolyses the dietary fibre is an enzyme which has an affinity for the dietary fibre as a substrate and so which binds to the dietary fibre.

In one embodiment the dietary fibre may be hydrolysed with said one or more enzymes for a period up to 24 hours.

In one embodiment the dietary fibre may be hydrolysed for between about 10 minutes and about 24 hours. In some embodiments the dietary fibre may be hydrolysed for between about 30 minutes to 20 hours, suitably 4 hours to 20 hours, suitably 14 hours to 20 hours.

In some embodiments the dietary fibre may be hydrolysed for between about 6 and about 24 hours. In some embodiments the dietary fibre may be hydrolysed for between 4-10 hours.

In some embodiments the dietary fibre may be hydrolysed for less than about 8 hours e.g. in order to reduce the secondary hydrolysis that can occur thereafter.

In some embodiments the dietary fibre may be hydrolysed for at least 30 minutes, e.g. at least 1 hour, or at least 4 h or at least 6 hours or at least 10 h or at least 15 h.

In some embodiments the dietary fibre may be hydrolysed for about 16 h.

In one embodiment the enzyme hydrolysis may hydrolyse polysaccharide components to oligosaccharides, but may avoid complete breakdown of the oligosaccharides to monosaccharides. In some embodiments the process is continued until approximately 35-50% of the polysaccharides or 35-50% of the cellulose is degraded to monosaccharides, suitably until approximately 40-48% of the polysaccharides or 40-48% of the cellulose is degraded to monosaccharides.

Conditions for hydrolysis will be optimum conditions for the specific enzyme being used. These are typically indicated when purchasing the enzyme, or determined experimentally. Suitably the hydrolysis may be carried out at the optimum pH for the enzyme(s) used. Suitably the hydrolysis may be carried out at a pH of between 5 and 8. Suitably the hydrolysis may be carried out at the optimum temperature for the enzyme(s) used. Suitably the hydrolysis may be carried out at a temperature between 45 and 65° C. Suitably the hydrolysis may be carried out with continuous stirring.

The enzyme treatment of the dietary fibre reduces the particle size. In other words the particle size of the functionalised dietary fibre is smaller than that of the dietary fibre before treatment.

In some embodiments enzyme treatment may reduce the mean volume diameter of the dietary fibre by a factor of about ten.

In one embodiment the dietary fibre after treatment may have a D50 particle size distribution of less than 10 μm.

In one embodiment the dietary fibre after treatment may have a D50 particle size distribution of less than 3 μm.

The dietary fibre (e.g. starting dietary fibre before treatment) may be milled to a suitable D50 particle size distribution, e.g. of less than 800 μm, or less than 500 μm, or less than 30 μm, or less than 10 μm or less than 3 μm by any suitable means. One suitable means may be jet milling. By way of example the dietary fibre may be milled in an IKA M20 batch mill (Milian, Switzerland) at a constant speed of 2000×g for 10 seconds.

In one embodiment the milling of the dietary fibre may occur before enzyme treatment.

In one embodiment the milling of the dietary fibre may occur after enzyme treatment, e.g. after drying said aqueous suspension.

In one embodiment the milling of the dietary fibre may occur both before and after enzyme treatment.

When the milling of the dietary fibre occurs, preferably the dietary fibre is in a relatively dry state.

Without wishing to be bound by theory the denatured enzyme of the present invention enzyme is believed to form amphiphilic complexes with the size-reduced fibre, thereby conveying surface-activity to the otherwise hydrophilic particle.

In one embodiment suitably the functionalised dietary fibre or Pickering particle has a $D_{90}$ particle size distribution of less than about 300 μm. In one embodiment the functionalised dietary fibre or Pickering particle has a $D_{90}$ particle size distribution of less than about 50 μm.

In one embodiment the functionalised dietary fibre or Pickering particle has a $D_{90}$ particle size distribution of less than about 25 μm.

In one embodiment the functionalised dietary fibre or Pickering particle has a $D_{90}$ particle size distribution of about 10 μm or less.

In one embodiment the functionalised dietary fibre or Pickering particle has a $D_{90}$ particle size distribution of about 3 μm or less.

In one embodiment the functionalised dietary fibre or Pickering particle has a $D_{50}$ particle size distribution of less than about 25 μm.

In one embodiment the functionalised dietary fibre or Pickering particle has a $D_{50}$ particle size distribution of about 10 μm or less.

In one embodiment the functionalised dietary fibre or Pickering particle has a $D_{50}$ particle size distribution of about 3 μm or less.

$D_{P,3}$ is measured in units of length (e.g. microns) and denotes that particle diameter for which P % of the total volume taken by the particle in the sample have a diameter smaller or equal to the length given for this parameter. Thus for example if $D_{90,3}=1$ micron, this means 90% of the total volume of particle in the sample is provided by those particles having a diameter 1 micron or less.

For example the volume mean particle size may be measured by a method which obtains a mean volume diameter of the particles by laser diffraction using a Malvern optical instrument (Mastersizer 2000, Malvern, UK).

In some preferred embodiments of the invention the functionalized dietary fibre particles of and/or used in the present invention may also have a Vol. PSD which is bi or mono-modal.

In some embodiments the functionalised dietary fibre or Pickering particle to oil size ratio (in an emulsion may be in the range of 1:10. In other words in some embodiments the functionalised dietary fibre (in combination with the denatured enzyme) or the Pickering particle should be at least one order of magnitude smaller than the oil droplets they stabilize.

In one embodiment the process according to the present invention comprises drying said aqueous suspension comprising a functionalised dietary fibre and denatured enzyme.

Drying may be undertaken by any known suitable means, including spray drying, vacuum drying, drum drying, freeze drying (or lyophilisation), or supercritical drying.

In one preferred embodiment the functionalised dietary fibre and denatured enzyme according to the present invention or Pickering particle according to the present invention is freeze dried.

The functionalised dietary fibre and denatured enzyme according to the present invention or the Pickering particle according to the present invention may be used in a dry state.

The functionalised dietary fibre and denatured enzyme according to the present invention or the Pickering particle according to the present invention may be in any suitable form. In one embodiment the present invention or the Pickering particle according to the present invention may be in the form of a granule or a powder.

In one preferred embodiment the present invention or the Pickering particle according to the present invention may be a powder.

There term "Pickering particle" as used herein means a solid particle which adsorb onto the interface between the oil and water phases in an emulsion, e.g. due to their wetting properties, to stabilize the emulsion thus forming a Pickering emulsion. The Pickering particle as used here may mean a particle which is interfacially active at the oil/water interface. In the present invention, the Pickering particles of the present invention may stabilise both oil in water and water in oil emulsions.

Enzyme(S)

Suitably the enzyme for use in the present invention may be one or more enzymes selected from the group consisting of endo-1,4-β-glucanase, cellobiohydrolase, β-glucosidase, endo-polygalacturonase, exo-polygalacturonase, pectin-methyl-esterase, endo-pectate lyase, exo-pectate lyase and pectin lyase.

Cellulose represents the main cell wall polysaccharide. In general, cellulose is a water-insoluble homopolymer consisting of a linear chain of repeating ß-1,4-glucosyl units. Individual celluloses chains are tightly bundled together into microfibrils and are held together by hydrogen bonding. Cellulose can vary in the ratio of amorphous and crystalline regions, of which the latter is very resistant to hydrolysis. Three different classes of enzymes are required for the depolymerisation of this unbranched and homogenous polymer: endo-1,4-β-glucanases (which hydrolyze cellulose to glucooligosaccharides); exoglucanases or cellobiohydrolases (which release cellobiose from cellulose and glucooligosaccharides) and ß-glucosidases (which degrade the cellobiose to glucose). The inaccessibility of cellulose to hydrolytic enzymes in the cell wall matrix is a key obstacle for its deconstruction. To make the cellulose more available, the cooperative action of pectin- and hemicellulose degrading enzymes and/or a suitable pretreatment may be needed. Pectins are a diverse group of polysaccharides and have the most complex structures (Vincken, Voragen and Beldman, 2003 Enzymes degrading rhamnogalacturonan and xylogalacturonan. In: J. Whitaker, A. Voragen and D. Wong, ed., Handbook of food enzymology, 1st ed. New York: Marcel Dekker, pp. 930-941). Structures that belong to this group are: homogalacturonan, rhamnogalacturonan 1 and 2, xylogalacturonan, arabinan, arabinogalactan 1 and 2 (Bonnin, Garnier, & Ralet, 2014 *Applied Microbiology and Biotechnology*, 98(2), pp. 519-532). Depending on the plant or plant fraction the type of pectin may differ.

Pectins are degraded by different types of pectinases, which can be distinguished depending on their action side and the type of degradation. Endo-polygalacturonase, exo-polygalacturonase and pectin/pectate lyases split the backbone of the smooth regions. Methyl-esterases and acetyl esterases are involved in the removal of methanol and acetylesters from galacturonic acid, respectively.

In one embodiment suitably the enzyme for use in the present invention may be an enzyme composition comprising more than one enzyme or more than one enzyme activity.

In one embodiment preferably the enzyme for use in the present invention comprises two or more enzyme activities selected from the group consisting of endo-1,4-β-glucanase, cellobiohydrolase, β-glucosidase, endo-polygalacturonase, exo-polygalacturonase, pectin-methyl-esterase, endo-pectate lyase, exo-pectate lyase and pectin lyase.

In the present invention one or more enzymes which act on cellulose, e.g. one or more of endo-1,4-β-glucanase, cellobiohydrolase, β-glucosidase may be used in combination with one or more pectin degrading enzymes, e.g. one or more of endo-polygalacturonase, exo-polygalacturonase, pectin-methyl-esterase, endo-pectate lyase, exo-pectate lyase and pectin lyase.

In one embodiment the one or more enzymes for use in the present invention is an enzyme cocktail that comprises endo-1,4-β-glucanase and β-glucosidase activity.

In one embodiment the one or more enzymes for use in the present invention is an enzyme cocktail that comprises cellobiohydrolase activity.

In one embodiment the one or more enzymes for use in the present invention is an enzyme cocktail that comprises endo-1,4-β-glucanase, cellobiohydrolase and β-glucosidase activity.

In one embodiment the one or more enzymes for use in the present invention is an enzyme cocktail comprising one or more of the enzyme activities selected from: endo-polygalacturonase, exo-polygalacturonase, pectin-methyl-esterase, endo-pectate lyase, exo-pectate lyase and pectin lyase.

In one embodiment of the present invention an enzyme cocktail comprising two or more of an endo-1,4-β-glucanase, cellobiohydrolase and/or β-glucosidase may be used in combination with one or more pectin degrading enzymes, e.g. one or more of endo-polygalacturonase, exo-polygalacturonase, pectin-methyl-esterase, endo-pectate lyase, exo-pectate lyase and pectin lyase.

In one embodiment of the present invention an enzyme cocktail comprising two or more of an endo-1,4-β-glucanase, cellobiohydrolase and/or β-glucosidase may be used in combination with a polygalacturonase, e.g. an endo-polygalacturonase or exo-polygalacturonase.

In one embodiment of the present invention an enzyme cocktail comprising a cellobiohydrolase may be used in combination with a polygalacturonase, e.g. an endo-polygalacturonase or exo-polygalacturonase.

In one embodiment of the present invention said one or more enzymes for use in the present invention may be one or more enzymes comprising (or having or consisting of) the polypeptide sequences shown herein as SEQ ID No. 1, SEQ ID No. 2 or SEQ ID No. 3 or a polypeptide sequence having at least 70% identity therewith.

In one embodiment of the present invention said one or more enzymes for use in the present invention may be one or more enzymes comprising (or having or consisting of) the polypeptide sequences shown herein as SEQ ID No. 1, SEQ ID No. 2 or SEQ ID No. 3 or a polypeptide sequence having at least 80% identity therewith.

In one embodiment of the present invention said one or more enzymes for use in the present invention may be one or more enzymes comprising (or having or consisting of) the polypeptide sequences shown herein as SEQ ID No. 1, SEQ ID No. 2 or SEQ ID No. 3 or a polypeptide sequence having at least 90% identity therewith.

In one embodiment of the present invention said one or more enzymes for use in the present invention may be one or more enzymes comprising (or having or consisting of) the polypeptide sequences shown herein as SEQ ID No. 1, SEQ ID No. 2 or SEQ ID No. 3 or a polypeptide sequence having at least 95% identity therewith.

In one embodiment of the present invention said one or more enzymes for use in the present invention may be a polypeptide having cellobiohydrolase activity comprising (or having or consisting of) a polypeptide sequence shown herein as SEQ ID No. 1 or SEQ ID No. 2 or an amino acid sequence which comprises a conservative substitution of at least one of the amino acids; or a variant, homologue or derivative of SEQ ID No. 1 or SEQ ID No. 2 having at least 70% identity therewith.

In one embodiment of the present invention said one or more enzymes for use in the present invention may be a polypeptide having polygalacturonase activity comprising (or having or consisting of) a polypeptide sequence shown herein as SEQ ID No. 3 or an amino acid sequence which comprises a conservative substitution of at least one of the amino acids; or a variant, homologue or derivative of SEQ ID No. 3 having at least 70% identity therewith.

In one embodiment of the present invention the one or more enzymes is encoded by a nucleotide sequence which encodes a polypeptide sequence selected from the group consisting of SEQ ID No. 1, SEQ ID No. 2 or SEQ ID No. 3 or an amino acid sequence which comprises a conservative substitution of at least one of the amino acids; or a variant, homologue or derivative of SEQ ID No. 1, SEQ ID No. 2 or SEQ ID No. 3 having at least 70% identity therewith.

In one embodiment of the present invention said one or more enzymes for use in the present invention may be a combination of a polypeptide shown herein as SEQ ID No. 1 or SEQ ID No. 2 or an amino acid sequence which comprises a conservative substitution of at least one of the amino acids; or a variant, homologue or derivative of SEQ ID No. 1 or SEQ ID No. 2 having at least 70% identity therewith, and a polypeptide having polygalacturonase activity comprising (or having or consisting of) a polypeptide sequence shown herein as SEQ ID No. 3 or an amino acid sequence which comprises a conservative substitution of at least one of the amino acids; or a variant, homologue or derivative of SEQ ID No. 3 having at least 70% identity therewith.

In one embodiment the enzyme is an endo-1,4-β-glucanase. Endo-1,4-β-glucanase enzymes can be characterised as having E.C. 3.2.1.4 according to the International Union of Biochemistry and Molecular Biology (IUBMB) Enzyme Nomenclature recommendations. This enzyme endohydrolyses (1→4)-β-D-glucosidic linkages in cellulose, lichenin and cereal β-D-glucans. Other names for this enzyme may include cellulase, β-1,4-glucanase; β-1,4-endoglucan hydrolase; cellulase A; cellulosin AP; endoglucanase D; alkali cellulase; cellulase A 3; celludextrinase; 9.5 cellulase; avicelase; pancellase SS; 1,4-(1,3;1,4)-β-D-glucan 4-glucanohydrola. The systemic name for this enzyme is 4-(1,3;1,4)-β-D-glucan 4-glucanohydrolase.

In one embodiment the enzyme is a β-glucosidase. β-glucosidase may be characterised as having E.G. classification 3.2.1.21 according to the International Union of Biochemistry and Molecular Biology (IUBMB) Enzyme Nomenclature recommendations. In some embodiments this enzyme hydrolyses terminal, non-reducing β-D-glucosyl residues with release of β-D-glucose. Other names for this enzyme may include gentiobiase; cellobiase; emulsin; elaterase; aryl-β-glucosidase; β-D-glucosidase; β-glucoside glucohydrolase; arbutinase; amygdalinase; p-nitrophenyl β-glucosidase; primeverosidase; amygdalase; linamarase; salicilinase; β-1,6-glucosidase. The systemic name for this enzyme is β-D-glucoside glucohydrolase. In one embodiment the enzyme may be a GH3 enzyme as classified using the Carbohydrate active enzyme database.

In one embodiment the enzyme is a cellobiohydrolase. The cellobiohydrolase may be cellulose 1,4-β-cellobiosidase (non-reducing end). The cellobiohydrolase may be characterised as having E.C. classification 3.2.1.91 according to the International Union of Biochemistry and Molecular Biology (IUBMB) Enzyme Nomenclature recommendations. In some embodiments this enzyme hydrolyses (1→4)-β-D-glucosidic linkages in cellulose and cellotetraose, releasing cellobiose from the non-reducing ends of the chains. Other names for this enzyme may include exo-cellobiohydrolase; β-1,4-glucan cellobiohydrolase; β-1,4-glucan cellobiosylhydrolase; 1,4-β-glucan cellobiosidase; exoglucanase; avicelase; CBH 1; C₁ cellulase; cellobiohydrolase I; cellobiohydrolase; exo-β-1,4-glucan cellobiohydrolase; 1,4-β-D-glucan cellobiohydrolase; cellobiosidase. The systemic name for this enzyme is 4-β-D-glucan cellobiohydrolase (non-reducing end).

In one embodiment the enzyme is an endo-polygalacturonase. In one embodiment the enzyme is an endo-1,4-α-polygalacturonase. Endo-1,4-α-polygalacturonase may be characterised as having E.C. classification 3.2.1.15 according to the International Union of Biochemistry and Molecular Biology (IUBMB) Enzyme Nomenclature recommendations. In some embodiments this enzyme hydrolyses (1→4)-α-D-galactosiduronic linkages in pectate and other galacturonans. Other names for this enzyme may include polygalacturonase, pectin depolymerase; pectinase; endopolygalacturonase; pectolase; pectin hydrolase; pectin polygalacturonase; endo-polygalacturonase; poly-α-1,4-galacturonide glycanohydrolase; endogalacturonase; endo-D-galacturonase; poly(1,4-α-D-galacturonide) glycanohydrolase. The systemic name for this enzyme is (1→4)-α-D-galacturonan glycanohydrolase.

In one embodiment the enzyme is an exo-polygalacturonase. Exo-polygalacturonases may be characterised as having E.C. classification 3.2.1.67 according to the International Union of Biochemistry and Molecular Biology (IUBMB) Enzyme Nomenclature recommendations. In some embodiments this enzyme hydrolyses the following reaction: [(1→4)-α-D-galacturonide]$_n$+H$_2$O=[(1→4)-α-D-galacturonide]$_{n-1}$+D-galacturonate. Other names for this enzyme may include galacturan 1,4-α-galacturonidase; poly(galacturonate) hydrolase; exo-D-galacturonase; exo-D-galacturonanase; exopoly-D-galacturonase; poly(1,4-α-D-galacturonide) galacturonohydrolase. The systemic name for this enzyme is poly[(1→4)-α-D-galacturonide]galacturonohydrolase.

In one embodiment the enzyme is a pectin-methyl-esterase. Pectin-methyl-esterases may be characterised as having E.C. classification 3.1.1.11 according to the International Union of Biochemistry and Molecular Biology (IUBMB) Enzyme Nomenclature recommendations. In some embodiments this enzyme hydrolyses the following reaction: pectin+n H$_2$O=n methanol+pectate. Other names for this enzyme may include Pectin demethoxylase: pectin methoxylas; pectin methylesterase. The systemic name for this enzyme is pectin pectylhydrolase.

In one embodiment the enzyme is an endo-pectate lyase. Endo-pectate lyases may be characterised as having E.C. classification 4.2.2.2 according to the International Union of Biochemistry and Molecular Biology (IUBMB) Enzyme Nomenclature recommendations. In some embodiments this enzyme hydrolyses the following reaction: eliminative cleavage of (1→4)-α-D-galacturonan to give oligosaccharides with 4-deoxy-α-D-galact-4-enuronosyl groups at their non-reducing ends. Other names for this enzyme may include alpha-1,4-D-endopolygalacturonic acid lyase; endo-alpha-1,4-polygalacturonic acid lyase; endogalacturonate transeliminase; endopectin methyltranseliminase; pectate transeliminase; pectic acid lyase; pectic acid transeliminase; pectic lyase; pectin trans-eliminase; PGA lyase; polygalacturonate lyase; polygalacturonic acid lyase; polygalacturonic acid trans-eliminase; polygalacturonic transeliminase; PPase-N. The systemic name for this enzyme is (1→4)-α-D-galacturonan lyase.

In one embodiment the enzyme is an exo-pectate lyase. Exo-pectate lyases may be characterised as having E.C. classification 4.2.2.9 according to the International Union of Biochemistry and Molecular Biology (IUBMB) Enzyme Nomenclature recommendations. In some embodiments this enzyme hydrolyses the following reaction: Eliminative cleavage of 4-(4-deoxy-α-D-galact-4-enuronosyl)-D-galacturonate from the reducing end of pectate, i.e. de-esterified pectin. Other names for this enzyme may include exo-PATE;

exo-PGL; exopectate lyase; exopectic acid transeliminase; exopolygalacturonate lyase; exopolygalacturonic acid-transeliminase; PATE; pectate exo-lyase. The systemic name for this enzyme is (1→4)-α-D-galacturonan reducing-end-disaccharide-lyase.

In one embodiment the enzyme is a pectin lyase. Pectin lyases may be characterised as having E.C. classification 4.2.2.10 according to the International Union of Biochemistry and Molecular Biology (IUBMB) Enzyme Nomenclature recommendations. In some embodiments this enzyme hydrolyses the following reaction: eliminative cleavage of (1→4)-α-D-galacturonan methyl ester to give oligosaccharides with 4-deoxy-6-O-methyl-α-D-galact-4-enuronosyl groups at their non-reducing ends. Other names for this enzyme may include endo-pectin lyase; pectin methyltranseliminase; pectin trans-eliminase; pectolyase; PL; PMGL; PNL; polymethylgalacturonic transeliminase. The systemic name for this enzyme is (1→4)-6-O-methyl-α-D-galacturonan lyase.

In one embodiment enzyme activity can be measured in accordance with the enzyme assays presented in section 1.2.1 of the Examples section.

In one embodiment the enzyme may be selected from the group consisting of:

| | | |
|---|---|---|
| Cellulases including endoglucanase and beta-glucosidase | Novozymes (Sigma-Aldrich) | Celluclast ® Particularly Celluclast ® 1.5 L |
| beta-Glucanase | ABVista | Econase ® BG |
| β-glucosidase | Danisco | Accellerase ® BGTM |
| beta-Glucanase | Huvepharma | Hostazym C ® |
| beta-Glucanase | Le Saffre | Safizyme G |
| beta-Glucanase | Lyven | Feedlyve AGL |
| polygalacturonase | Novozymes (Sigma-Aldrich) | Pectinex Ultra SP-L |

In one embodiment suitably the enzyme may be Celluclast® 1.5 L or Pectinex Ultra SP-L or a combination thereof.

In one embodiment the enzyme may be an enzyme complex comprising more than one enzyme activity.

The process of the present invention provides that the enzyme(s) are denatured. Without wishing to be bound by theory, the enzyme(s) in their active and soluble form did not show any emulsifying properties in combination with the functionalised dietary fibre. However, when the enzyme(s) were deactivated or denatured, they became surface-active agents, and stabilized the emulsion in the presence of functionalised dietary fibre. Without wishing to be bound by theory, the denatured enzyme(s) may form amphiphilic complexes with the functionalised dietary fibre, thus conveying surface activity to the otherwise hydrophilic fibre particle. The data show that the enzyme(s) is/are bound to the functionalised dietary fibre as the enzyme is not extracted with the soluble phase and can be measured in the insoluble phase by SDS PAGE.

The enzyme(s) may be denatured by any suitable means, for example by heat, such as increasing the temperature above 60° C., e.g. 100° C. for 10 minutes; or by extremes of pH, e.g. alkali treatment such as by increasing the pH to above 9.

In one embodiment the functionalised dietary fibre and denatured enzyme of the present invention or the Pickering particle of the present invention comprises denatured enzyme at a ratio above 0.25 mg denatured enzyme: 1 g oil.

In one embodiment the enzyme may be selected to be one with an optimal pH within the pH range for product application. This may ensure stability against flocculation in the final product.

Dietary Fibre

The present invention relates to a process for forming functionalised dietary fibre.

The present invention comprises admixing an enzyme and a dietary fibre which is at a D90 particle size distribution of less than 800 microns and which comprises from at least 40 wt. % cellulose.

In one embodiment the dietary fibre may have at least 50% wt. % cellulose.

In one embodiment the dietary fibre may have at least 55% wt. % cellulose.

In one embodiment the dietary fibre may have at least 60% wt. % cellulose.

In one embodiment the dietary fibre may have between about 40-98 wt. % cellulose.

In one embodiment the dietary fibre may have between about 50-80 wt. % cellulose.

In one embodiment the dietary fibre may have between about 60-75 wt. % cellulose.

The present invention comprises admixing an enzyme and a dietary fibre which is at a D50 particle size distribution of less than 30 microns and which comprises from at least 40 wt. % cellulose.

In one embodiment the dietary fibre may have at least 50% wt. % cellulose.

In one embodiment the dietary fibre may have at least 55% wt. % cellulose.

In one embodiment the dietary fibre may have at least 60% wt. % cellulose.

In one embodiment the dietary fibre may have between about 40-98 wt. % cellulose.

In one embodiment the dietary fibre may have between about 50-80 wt. % cellulose.

In one embodiment the dietary fibre may have between about 60-75 wt. % cellulose.

In one embodiment the dietary fibre in accordance with the present invention may be a plant hull fibre. In another embodiment the dietary fibre may be from a fibre-rich fraction of a vegetable or fruit.

The hull or husk of a plant is the outer shell or coating of a seed. A husk or hull includes the protective outer covering of a seed, fruit or vegetable. The hull of a legume and some similar fruits may be called a pod.

In one embodiment the plant hull fibre may be any plant hull fibre which comprises less than 25 wt. % soluble fibres.

In one embodiment the plant hull fibre may be any plant hull fibre which comprises less than 20 wt. % soluble fibres.

In one embodiment the plant hull fibre may be any plant hull fibre which comprises less than 15 wt. % soluble fibres.

In one embodiment the plant hull fibre may be any plant hull fibre which comprises less than 10 wt. % soluble fibres.

In one embodiment the plant hull fibre may be any plant hull fibre which comprises less than 25 wt. % soluble fibres and at least 40% wt. % cellulose.

In one embodiment the plant hull fibre may be any plant hull fibre which comprises less than 20 wt. % soluble fibres and at least 50% wt. % cellulose.

In one embodiment the plant hull fibre may be any plant hull fibre which comprises less than 15 wt. % soluble fibres and at least 55% wt. % cellulose.

In one embodiment the plant hull fibre may be any plant hull fibre which comprises less than 10 wt. % soluble fibres and at least 60% wt. % cellulose.

In one embodiment the plant hull fibre is selected from the group consisting of pea hull fibre, pulse hulls (e.g. lentil, beans), bamboo fibre, cocoa fibres and coffee fibres. The plant hull fibre may be pea hull fibre.

In one embodiment the dietary fibre may be selected on taste as well as other characteristics.

By way of example the dietary fibre may be one with a neutral taste or one which is tasteless.

In one embodiment the dietary fibre may be selected on colour as well as other characteristics.

By way of example the dietary fibre may be one which is light in colour or neutral in colour or colourless.

In one embodiment the dietary fibre may be selected on smell as well as other characteristics.

By way of example the dietary fibre may be one which is odourless.

In one embodiment the dietary fibre is not wheat-bran (or wheat fibre).

In one embodiment the dietary fibre is not apple pomace or apple fibre.

In one embodiment the dietary fibre is not *psyllium*.

In one embodiment the dietary fibre is not a high soluble pectin fibre, e.g. the dietary fibre may be one which has less than 50% soluble pectin.

In one embodiment the dietary fibre is not a low cellulose containing fibre, e.g. is not one with less 60 wt % cellulose.

TABLE A

Composition of commercially available pea hull fibres as % w/w of dm (as reviewed by Guillon & Champ, 2002)

|  | Pea cotyledon | Pea hull |
|---|---|---|
| Total dietary fibre | 55 | 89 |
| Soluble dietary fibre | 14 | 7 |
| Protein | 17 | 5 |
| Lipid | 0.5 | 1.5 |
| Available carbohydrates[a] | 23 | 2 |
| Mineral | 4 | 4 |

[a]Digestible poly-, oligo- and monosaccharides

The term "fibre" as used herein means dietary material containing substances such as cellulose, lignin, and pectin, that are resistant to the action of digestive enzymes.

A detailed knowledge about the chemical structure of the fibres may be desirable in order to select an optimal enzyme preparation for their degradation. Cell walls of the pea hulls consist of approximately 69% w/w cellulose, 16.8% w/w pectin and 7.5% w/w hemicellulose on dry basis (Reichert, 1982), which is consistent with the neutral sugar composition reported in several studies (see Table B). Pea hulls are only poorly lignified (<1.5% w/w of dm) and therefore are considered not to have a high amount of secondary cell walls (Weightman et al. 1995 *Carbohydrate Polymers*, 26, pp. 121-128; Reichert 1981 *Cereal Chemistry*, 58(4), pp. 266-270).

TABLE B

Composition (mg/g) of pea hulls (Weightman et al., 1995 *Carbohydrate Polymers*, 26, pp.121-128)

| Sugar | Rhamnose | Fucose | Arabinose | Xylose | Galactose | Glucose | AUA[b] |
|---|---|---|---|---|---|---|---|
| mg/g | 16 | nd[a] | 39 | 122 | 28 | 581 | 150 |

[a]nd, not detected
[b]AUA, anhydrouronic acids

The term "functionlised" as used herein means that the dietary fibre is modified (e.g. by the method of the present invention) by admixing with an enzyme to have emulsion stabilization properties when in combination with denatured enzyme. The term "functionalised" as used herein can mean capable of providing a function e.g. oil-in-water emulsion stabilizer. The term "functionlised" as used herein may mean that the dietary fibre is modified (e.g. by the method of the present invention) to form a Pickering particle. Without wishing to be bound by theory, the dietary fibre e.g. PHF, may be modified by reducing particle size and inducing amphiphilicity at the particle surface using one or more enzymes with fibre degrading activities.

Peas (*Pisum sativum* L.) are a rich source of complex carbohydrates and have gained interest as a fibre-rich by-product of commercial value (Weightman et al. 1995). The amount of total dietary fibre and the relative content of cellulosic and non-cellulosic polysaccharides depends on their localization in the cotyledon or the hull of the pea (Guillon & Champ 2002). In this study, we chose to work with a commercial pea hull fibre preparation from yellow pea (Exafine, Cosucra), because of its generally higher total dietary fibre content and due to less starch and protein contaminants (see Table A).

Besides being rich in cellulose, pea hulls contain significant amounts of pectin and hemicellulose. Pectic fractions from pea hulls contain both homogalacturonan and rhamnogalacturonan regions with very complex and diverse side-chains primarily consisting of arabinosyl, galactosyl and xylosyl residues. In pea hulls, rhamnosyl residues occurred in (1→2)-linked, (1→2,4)-linked and terminal form (Renard et al. 1997). Rhamnogalacturonans with 1→5 linked arabinans associated with type 1 and 2 (arabino) galactans are reported the most common feature. Arabinans also occur in their free form in pea hulls (Weightman et al. 1995 *Carbohydrate Polymers*, 26, pp. 121-128; Renard et al. 1997 (see below); Ralet et al. 1993 (see below)). Uronic acids mainly consist of galacturonic acid with a galacturonic acid/glucuronic acid ratio of 97:3 (Weightman et al., 1994 *Carbohydrate Polymers*, 24(2), pp. 139-148). The homogalacturonan fraction from pea hulls is reported to have a relatively low degree of methylation (approx. 12-50) and to be highly acetylated, which distinguishes them from the highly methylated pectins usually found in primary cell walls of fruits (Weightman et al. 1995 *Carbohydrate Polymers*, 26, pp. 121-128; Le Goff et al. 2001 *Carbohydrate Polymers*, 45(4), pp. 325-334; Weightman et al. 1994 *Carbohydrate Polymers*, 24(2), pp. 139-148). Several studies also reported a significant amount of xylogalacturonan in pea hulls (18 mg/g), in which xylosyl units are present as single units or short side-chains on a galacturonic acid backbone (Le Goff et al. 2001 *Carbohydrate Polymers*, 45(4), pp. 325-334; Weightman et al. 1995 *Carbohydrate Polymers*, 26, pp. 121-128; Ralet et al. 1993 *Biochemical Engineering Journal*, 16(2), pp. 191-201; Renard et al. 1997 *International Journal of Biological Macromolecules*, 21(1-2), pp. 155-162). Methylation analysis identified (1,4)- and (1,3,4)-linked galacturonic acid residues and terminal xylosyl residues, suggesting substitution of the galacturonan backbone by xylose on O-3. In addition, some oligomeric side-chains of (1→2)-linked xylose were identified. The molar ratio of xylose to galacturonic acid was reported to be 0.76 (Le Goff et al., 2001 *Carbohydrate Polymers*, 45(4), pp. 325-334). Xylogalacturonans can be considered as a subfraction of the hairy regions of pectins (Schols et al., 1995 *Carbohydrate Research*, 279, pp. 265-279).

Xylans are the most abundant hemicellulose found in pea hulls (Weightman et al. 1994 *Carbohydrate Polymers*, 24(2), pp. 139-148; Tosh & Yada 2010 *Food Research International*, 43(2), pp. 450-460). The xylans found in pea hulls are mostly acidic xylans having a (1→4)-$\beta$-$_D$-xylan backbone with few branching points at O-2 and arabinoxylans (Banerji & Rao 1963 Structural Studies On An Arabinoxylan From Pea Skin (*Pisum Sativum*): Part I. Methylation Studies. *Canadian Journal of Chemistry*, 41(11), pp. 2844-2848; Renard et al. 1997 *International Journal of Biological Macromolecules*, 21(1-2), pp. 155-162; Weightman et al. 1994 *Carbohydrate Polymers*, 24(2), pp. 139-148; Ralet et al. 1993 *Biochemical Engineering Journal*, 16(2), pp. 191-201). The arabinose to xylose ratio in the hemicellulotic fraction extracted from pea hulls is 0.36 (Ralet et al. 1993 supra). The presence of a small amount of xyloglucan is also shown by Weightman et al. (1994 *Carbohydrate Polymers*, 24(2), pp. 139-148), but these structures are more frequently found in the cotyledon of the peas (Hayashi & MacLachlan 1984 *Plant Physiology*, 75(3), pp. 596-604).

Emulsions

Emulsions are a mixture of two immiscible fluids, in most cases water (w) and oil (o), in which the oil phase is dispersed in the aqueous phase in the form of oil droplets (o/w emulsions) or in which water droplets are dispersed in an oil phase (w/o emulsions). An emulsion is a thermodynamically unstable system (Floury, Desrumaux and Lardibres, 2000 *Innovative Food Science & Emerging Technologies*, 1(2), pp. 127-134). Amphiphilic proteins or low-molecular-weight emulsifiers (LMWE) that adsorb at the o/w interface, are most commonly used to delay the thermodynamically driven phase separation of the emulsion by reducing surface tension. Naturally-occurring fibre materials, including PHF, are predominantly hydrophilic and hence have no tendency to adsorb at the oil-water interface. Fibres, when used as hydrocolloids, are typically added to o/w emulsions at high concentrations where their ability to thicken/gel the water-continuous phase physically traps the oil droplets hence slowing down creaming and coalescence of oil droplets.

Pickering particles need to have adequate size and wettability for both phases in order to adsorb at the interface. The most common technique to characterize the wettability of a material is to measure the contact angle that a liquid interface makes with a solid. The principle of this measurement is based on Young's equation $y_{lv} \cos \theta_Y = y_{sv} - y_{sl}$, where $y_{lv}$, $y_{sv}$ and $y_{sl}$ represent liquid-vapour, solid-vapour and solid-liquid interfacial tensions, respectively and $\theta_Y$ is the contact angle (Bracco and Holst, 2013 Surface Science Techniques. 51st ed. Heidelberg: Springer). The particle size and particularly its contact angle will determine the particle's position at the interface, which defines the energy that is needed for desorption of such particles from the interface. With an adequate contact angle ($30° < \theta_Y < 150°$) the energy of desorption can be of several thousand kTs for all particles above 10 nm, therefore particles are said to be irreversibly attached (Hunter et al., 2008 *Advances in Colloid and Interface Science*, 137(2), pp. 57-81), providing long-term stability to the emulsion.

Without wishing to be bound by theory dietary fibre (plant hull fibre) structural components, like crystalline cellulose and hydrophobic methyl-, acetyl- and ferulic acid esters on the pectin backbone may become exposed at the particle surface by the enzyme treatment in accordance with the present invention and hence confer a certain degree of amphiphilicity to the otherwise very hydrophilic surface.

The functionalised dietary fibre and denatured enzyme according to the present invention or the Pickering particle in accordance with the present invention may be used to stabilise and emulsion. The emulsion may be an oil in water (o/w) emulsion or a water in oil (w/o) emulsion or an oil continuous dispersion or a double-emulsion (e.g. w/o/w).

The present invention provides an oil-in-water emulsion or water-in-oil emulsion comprising the functionalised dietary fibre and denatured enzyme according to the present invention or the Pickering particle according to the present invention.

In one embodiment the functionalised dietary fibre and denatured enzyme according to the present invention or the Pickering particle in accordance with the present invention may be used in combination with another emulsifier e.g. Na-Caseinate.

In one embodiment the functionalised dietary fibre and denatured enzyme according to the present invention or the Pickering particle in accordance with the present invention comprise a significant amount of protein, e.g. more than 0.5 mg/1 g oil, such as between 0.6 and 0.9 mg/1 g oil.

Uses

The functionalised dietary fibre and denatured enzyme of the present invention or the Pickering particle according to the present invention may be used to stabilize an emulsion, e.g. a water-in-oil emulsion or an oil-in-water emulsion.

The emulsion may be one that is used in any product, such as in a food product or a cosmetic product or a pharmaceutical product.

The present invention further provides a food product or a cosmetic product or a skin care product or a pharmaceutical product or a personal hygiene product or a hairstyling product comprising a functionalised dietary fibre and denatured enzyme according to the present invention or a Pickering particle according to the present invention.

The functionalised dietary fibre and denatured enzyme according to the present invention or a Pickering particle according to the present invention stabilise the emulsion.

By "stabilise" as used herein we mean that the functionalised dietary fibre and denatured enzyme according to the present invention or a Pickering particle according to the present invention delay the separation of an emulsion into a water and an oil phase, e.g. by coalescence of droplets. In one embodiment, the stability of the emulsions against collapse may be considered.

A food product or a cosmetic product or a skin care product or a pharmaceutical product or a personal hygiene product or a hairstyling product may comprise and be stabilised by the functionalised dietary fibre and denatured enzyme according to the present invention or the Pickering particle according to the present invention.

Food Products

The Pickering particles of the present invention or the functionalised dietary fibre and denatured enzyme according to the present invention may be used in a food emulsion, e.g. a mixture of two or more liquids that are normally immiscible.

Here, the term "food" is used in a broad sense—and covers food for humans as well as food for animals (i.e. a feed). In a preferred aspect, the food is for human consumption.

The emulsion may be an oil in water emulsion or a water in oil emulsion or an oil continuous dispersion or a double-emulsion (e.g. w/o/w). Examples of food emulsions in which the present invention may be used include vinaigrettes, homogenised milk, sauces, e.g. mayonnaise or hollandaise sauce, soups, crema (foam) in espresso, dairy emulsions and plant-based emulsions such as soy drinks.

Skin Care Products

The Pickering particles of the present invention or the functionalised dietary fibre and denatured enzyme according to the present invention may be used in a skin care product.

The skin care product may be any product comprising an emulsion.

The skin care product may be for example cleansing, protective, treatment or care creams; UV protective sun creams; skincare lotions, such as cleansing or disinfecting lotions; or moisturisers.

The skin care product of the present invention may be a composition comprising other ingredients including shea butter, cocoa butter, coconut oil, sunflower oil and nut kernel oils (such as apricot kernel oil).

When the composition of the invention is an emulsion, the proportion of the fatty phase may range from 5% to 80% by weight, and preferably from 10% to 50% by weight, relative to the total weight of the composition.

Pharmaceutical, Hairstyling, Personal Hygiene & Cosmetics Products

In pharmaceuticals, hairstyling, personal hygiene, and cosmetics, emulsions are frequently used. These emulsions may be called creams, ointments, liniments (balms), pastes, films, or liquids, depending mostly on their oil-to-water ratios, other additives, and their intended route of administration.

The emulsions may be topical dosage forms, and may be used on the surface of the skin, transdermally, ophthalmically, rectally, or vaginally.

A highly liquid emulsion may also be used orally, or may be injected in some cases.

Popular medications occurring in emulsion form include cod liver oil, Polysporin, cortisol cream or Canesten for example.

Nucleotide Sequence

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

Preparation of the Nucleotide Sequence

A nucleotide sequence encoding an enzyme of the present invention may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

In an alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

Amino Acid Sequences

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

Sequence Identity or Sequence Homology

The present invention also encompasses the use of sequences having a degree of sequence identity with amino acid sequence(s) of a polypeptide having the specific properties defined herein or of any nucleotide sequence encoding such a polypeptide.

The amino acid sequence and/or nucleotide sequence should provide and/or encode a polypeptide which retains the functional activity.

In some embodiments the amino acid sequence or nucleotide sequence may be at least 75, 85 or 90% identical, preferably at least 95 or 98% identical to the subject sequence. Typically, the sequences with percentage identity will comprise the same active sites etc. as the subject amino acid sequence for instance.

In one embodiment, a sequence which has percentage identity may be taken to include an amino acid sequence or nucleotide sequence which has one or several additions, deletions and/or substitutions compared with the subject sequence.

In one embodiment the present invention relates to a protein whose amino acid sequence (or to a nucleic acid sequence (or gene) encoding a protein whose amino acid sequence) is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

Suitably, the degree of identity with regard to an amino acid sequence or nucleotide sequence is determined over at least 20 contiguous amino acids/nucleotides, preferably over at least 30 contiguous amino acids/nucleotides, preferably over at least 40 contiguous amino acids/nucleotides, preferably over at least 50 contiguous amino acids/nucleotides, preferably over at least 60 contiguous amino acids/nucleotides, preferably over at least 100 contiguous amino acids/nucleotides, preferably over at least 200 contiguous amino acids/nucleotides.

Suitably, the degree of identity with regard to an amino acid sequence or nucleotide sequence is determined over the entire length of the amino acid sequence or nucleotide sequence.

Identity comparisons can be conducted by eye, or more usually, with the aid of readily available sequence comparison programs. These commercially available computer programs can calculate % homology between two or more sequences.

% identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % identity therefore firstly requires the production of an optimal alignment, taking into consideration gap penalties. A suitable computer program for carrying out such an alignment is the the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60), such as for example in the GenomeQuest search tool (www.genomequest.com).

Although the final % identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
|---|---|
| GAP OPEN | 9 |
| GAP EXTENSION | 2 |

| FOR CLUSTAL | DNA | PROTEIN |
|---|---|---|
| Weight Matrix | IUB | Gonnet 250 |
| GAP OPENING | 15 | 10 |
| GAP EXTEND | 6.66 | 0.1 |

In one embodiment, CLUSTAL may be used with the gap penalty and gap extension set as defined above.

In the present context, the term "query sequence" means a homologous sequence or a foreign sequence, which is aligned with a subject sequence in order to see if it falls within the scope of the present invention. Accordingly, such query sequence can for example be a prior art sequence or a third party sequence.

In one preferred embodiment, the sequences are aligned by a global alignment program and the sequence identity is calculated by identifying the number of exact matches identified by the program divided by the length of the subject sequence.

In one embodiment, the degree of sequence identity between a query sequence and a subject sequence is determined by 1) aligning the two sequences by any suitable alignment program using the default scoring matrix and default gapp enalty, 2) identifying the number of exact matches, where an exact match is where the alignment program has identified an identical amino acid or nucleotide in the two aligned sequences on a given position in the alignment and 3) dividing the number of exact matches with the length of the subject sequence.

In yet a further preferred embodiment, the global alignment program is selected from the group consisting of CLUSTAL and BLAST (preferably BLAST) and the sequence identity is calculated by identifying the number of exact matches identified by the program divided by the length of the subject sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by synthetic amino acids (e.g. unnatural amino acids) include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, ß-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline#, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

Expression of Enzymes

The nucleotide sequence for use in the present invention may be incorporated into a recombinant replicable vector. The vector may be used to replicate and express the nucleotide sequence, in protein/enzyme form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes-such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question.

Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence for use according to the present invention is operably linked to at least a promoter.

Other promoters may even be used to direct expression of the polypeptide of the present invention.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

Constructs

The term "construct"—which is synonymous with terms such as "conjugate", "cassette" and "hybrid"—includes a nucleotide sequence for use according to the present invention directly or indirectly attached to a promoter.

The construct may even contain or express a marker, which allows for the selection of the genetic construct.

For some applications, preferably the construct of the present invention comprises at least the nucleotide sequence for use in the present invention operably linked to a promoter.

Host Cells

The term "host cell"—in relation to the present invention includes any cell that comprises either the nucleotide sequence or an expression vector as described above and which is used in the recombinant production of a protein having the specific properties as defined herein.

Thus, a further embodiment of the present invention provides host cells transformed or transfected with a nucleotide sequence that expresses the protein of the present invention. The cells will be chosen to be compatible with the said vector and may for example be prokaryotic (for example bacterial), fungal, yeast or plant cells.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

Culturing and Production

Host cells transformed with the nucleotide sequence of the present invention may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

Often, it is desirable for the protein to be secreted from the expression host into the culture medium from where the protein may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

Advantages

The advantages of the present invention will be apparent from the teachings herein.

One advantage of the present invention is the production of functionalized dietary fibre and denatured enzyme and their use as Pickering particles, e.g. to stabilize emulsions and/or replace the use of surfactants in emulsion production.

One advantage of the present invention is that emulsions stabilised with low amounts (0.4% w/v) of functionalized dietary fibre and denatured enzyme of the present invention effectively protect large, creamed oil droplets against coalescences for four weeks or longer.

One further advantage of the present invention is that emulsions stabilised with low amounts (0.4% w/v) of functionalized dietary fibre and denatured enzyme of the present invention effectively protect large, creamed oil droplets against coalescences over a wide range of pH (e.g. pH 3.0-8.0).

Pickering particles according to the present invention have been found to have superior stability on an emulsion compared with proteins or surfactants alone.

One additional advantage of the present invention is that the functionalised dietary fibre and denatured enzyme or Pickering particle according to the present invention can replace convention emulsion stabilisers thus providing a clean-label, dairy-free, fibre-based emulsion stabiliser.

The functionalised dietary fibre and denatured enzyme or Pickering particle according to the present invention may stabilise relatively large droplets, e.g. up to 500 µm.

The functionalised dietary fibre and denatured enzyme or Pickering particle according to the present invention may provide improved texture and/or flavour and/or colour and/or odour characteristics compared with convention emulsion stabilisers.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure which can be had by reference to the specification as a whole. Accordingly, the terms defined herein are more fully defined by reference to the specification as a whole.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following Figures and Examples.

EXAMPLES

The increasing health-awareness of consumers is causing growing demand for products based on natural ingredients. In this research, dietary fibre particularly fibre (e.g. cellulose) rich fractions from the husk (or hull) of plants, e.g. pea hulls are evaluated as functional food ingredients. Such a use would be a promising way to valorise this raw material and to develop healthier products. Pea hulls for example are rich in dietary fibre (approx. 90% w/w of dm) and consist mainly of cellulose (69% w/w of dm), hemicellulose (7.5% w/w of dm) and pectin (16.8% w/w of dm) (Reichert, 1981 Cereal Chemistry 58(4) pp 266-270 incorporated herein by reference). Epidemiological evidence shows that the intake of fibre has important health implications (Hu, 2003 American J. of Clinical Nutrition (78) pp 544-551 incorporated herein by reference). In addition, pea hulls fibres (PHF) for example have a neutral taste, are light coloured and hence could be incorporated into different food products as an 'invisible' fibre source (Guillon & Champ 2002 The British J. of Nutrition 88 Suppl. 3, pp. S293-S306 incorporated herein by reference). The effect of hydrolysis of dietary fibre, e.g. PHF, with selected enzymes on their functionalities and finding new applications for these modified fibres is taught herein. Two systems were studied, namely oil continuous dispersions and oil-in-water (o/w) emulsions.

Example 1

Methodology

1.1. Materials

Substrate

Powdered Exafine® PHF was purchased from Cosucra (Pecq, Belgium). The material was passed once through the Jet-mill at constant pressure of 10 Bars and a feeding rate 0.5 kg/h to reduce particle size and ensure better dispersibility in solutions. Approximate composition of the PHF is shown in table 1.

TABLE 1

| Approximate composition of Exafine PHF Information was provided by Cosucra. | |
|---|---|
| Component | Percentage (% w/w) |
| Fibre | Min 85% |
| Starch | Max. 5% |
| Protein | Max 6.5% |
| Ash | Max 3% |
| Dry matter | 94 ± 3% |

Enzymes

Cellulolytic and pectinolytic enzymes (table 2 and table 3) were selected for enzymatic treatment based on the most abundant polymer classes in plant hulls, e.g. pea hulls.

Purified Enzymes

TABLE 2

Description of purified enzymes used in this study.
Information was provided by Megazyme.

| Commercial enzyme | Coding[b] | Supplier | Fungal origin | CAZy[a] | EC number | Main activity | Optimum pH | Optimum temperature |
|---|---|---|---|---|---|---|---|---|
| E-CELAN | PHF-E-CELAN | Megazyme | *A. niger* | GH 12 | EC 3.2.1.4 | Endo-1,4-β-D-glucanase | 4.5 | 60° C. |
| E-BCLUC | PHF-E-BCLUC | Megazyme | *A. niger* | GH 3 | EC 3.2.1.21 | β-Glucosidase | 4 | 70° C. |
| E-XYAN4 | PHF-E-XYAN4 | Megazyme | *A. niger* | GH 11 | EC 3.2.1.8 | 4-β-D-xylan xylanohydrolase | 4.5 | 60° C. |

[a]CAZy = Carbohydrate active enzyme database (www.CAZy.org)
[b]Coding for PHF treated with respective enzymes.

Commercial Enzyme Cocktails

TABLE 3

Description of commercial enzyme cocktails used in this study.
Information was provided by Novozymes.

| Commercial enzyme | Coding[a] | Supplier | Fungal origin | Main activity | Optimum pH | Optimum temperature |
|---|---|---|---|---|---|---|
| Celluclast 1.5 L (Cell) | PHF-Cell | Novozymes | *Trichoderma reesei* ATCC 26921 | Endo-glucanase | 5 | 65° C. |
| Pectinex Ultra SP-L (Pec) | PHF-Pec | Novozymes | *Aspergillus aculeatus* | Polygalacturonase | n.a. | n.a. |

[a]Coding for PHF treated with respective enzymes

1.2. Enzymatic Modification of Plant Hull Fibres, e.g. Pea Hull Fibres

1.2.1. Determination of Enzyme Activity

Xylanase, Cellulase and Pectinase Activity Assays

Xylanase (endo-β-1,4 xylanase) cellulase (endo-β-1,4-glucanase) and pectinase (endo-1,4-α-polygalacturonanase) activities were assayed using dinitrosalicylic (DNS) method for reducing sugars. 1% (w/v) substrate solutions of either wheat arabinoxylan (medium viscosity, Megazyme, Ireland) or carboxymethyl cellulose (CMC, Megazyme, Ireland) or polygalacturonic acid (Megazyme, Ireland) were prepared in 100 mM citrate-phosphate buffer at pH 5.0 12.5 µL enzyme dilution (1:10-1:10000) were added to 112.5 µL of respective substrate solution in a 1.5 mL Eppendorf tube. Reactions were performed at 50° C. for 10 min. Reactions were stopped on ice and adding 125 µl of DNS reagent. Control samples involved adding DNS reagent prior to the addition of the enzymes. Blank sample involved adding water instead of enzyme. Respective standard curves of xylose and glucose were prepared (standards from 0.1 to 2 mg/mL in water). Absorbance was determined at 540 nm using a Unicam UV-visible spectrometer (Helios Gamma, Helios Delta, UK).

In this research, one unit of activity (1 U) is defined as the mass (mg) or mL of enzyme preparation releasing 1 µmol of product (glucose, xylose) per minute under the defined conditions. All assays were prepared and analyzed in duplicate.

β-Glucosidase Activity Assay

β-glucosidase activity was determined at pH 5.0 using 1 mM p-nitrophenyl-β-D-glucopyranoside (pNP-β-$_D$-glcP, Sigma, Switzerland) solution was prepared in 100 mM citrate-phosphate buffer. 0.25 mL of the appropriate enzyme dilution (1:10-1:10000) were added to 1.25 mL of pNP-b-D-glcP. Reactions (50° C., 10 min) were stopped on ice by adding 0.25 mL of $Na_2CO_3$ (2% w/v, Merck). Absorbance was determined at 410 nm using a Unicam UV-visible spectrometer (Helios Gamma, Helios Delta, UK). Control samples involved adding $Na_2CO_3$ prior to the addition of the enzyme activities. Blank sample involved adding water instead of enzyme. A standard curve of p-nitrophenol (0.05 mM-0.3 mM) was prepared. In this research, one U of β-glucosidase was defined as the amount of enzyme that released 1 µmol p-nitrophenol per min under the assay conditions.

Protease Activity Assay

Protease activity in commercial enzyme preparations and plant hull fibre, e.g. PHF, was measured with the Megazyme endo-Protease Kit using protazyme AK tablets. A protazyme AK tablet was added to 5 mL 100 mM acetate buffer at pH 5 mL in a 20 mL glass tube and the tablet was allowed to hydrate for 1 hour at 50° C. Enzyme and PHF were diluted in acetate buffer (1:1-1:10000) and stirred for 15 minutes at room temperature. 1 mL of enzyme suspension was added to the stirred tube and the reaction was continued for 10 minutes and 1, 8, 24 hours. The reaction was terminated by adding 10 mL 2% w/v trisodium phosphate buffer, pH 12, with vigorous stirring on a vortex mixer. The tubes were left at room temperature for 5 minutes. If a precipitate was formed, the supernatant was centrifuged at 1000 xg for 10 minutes. Absorbance of filtrate was measured at 590 nm against a reaction blank. Positive control contained Alcalase (20,000×diluted). One Protease Unit was defined as the amount of enzyme/PHF, which produces the equivalent of one micromole of tyrosine per minute from soluble casein at given conditions. Standard curve was provided by Megazyme (milli-Units/assay (i.e. 1 mL))=2029×Abs590-4.5; $R^2$=0.99).

1.2.2. Enzymatic Treatment of Plant Hull Fibres, e.g. Pea Hull Fibres, with Purified Enzymes and Commercial Enzyme Cocktails Incubation A 10% total solids (TS) dispersion of PHF in 100 mM citrate/phosphate buffer pH 5.0 was prepared and stirred for 1 hour at room temperature to allow full hydration. The buffer contained 0.04% w/v $NaN_3$ (Sigma Aldrich, Switzerland) as anti-microbial agent. Enzymatic reactions were performed overnight (16 hours) under continuous stirring at 430 rpm at 50° C. Enzyme doses used are indicated in table 6 in the results section. Samples were boiled for 10 minutes to end the enzymatic reaction. For the standard control, PHF were subjected to the same treatment without enzyme addition. Other controls contained deactivated enzymes or bovine serum albumin (BSA) instead of active enzyme at equivalent protein concentrations, with and without PHF. pH adjustment of BSA dispersions was performed with 1 M HCl and 1 M NaOH. PHF dispersions obtained after enzymatic treatment were either directly used for further analyses or freeze-dried before further use.

Freeze-Drying and Milling

For experiments that required treated PHF in dry state, PHF dispersions were freeze-dried. The dispersion obtained after treatment was centrifuged in a Sorvall SLA-3000 fixed angle rotor (Thermofisher Scientific, Switzerland) at 10,000 xg for 10 minutes at 20° C. The obtained pellet was collected and freeze-dried (−40° C., $10^{-1}$ mbar for 72 h). After freeze-drying, the dry mass was transferred to an IKA M20 batch mill (Milian, Switzerland) and milled at a constant speed of 2000 xg for 10 seconds.

1.3. Physicochemical Properties of Pea Hull Fibres

1.3.1. Moisture Content

The moisture content of freeze-dried treated PHF and controls was measured using Mettler Toledo METLAB moisture analyser (Mettler-Toledo, Switzerland). The method "Puree en flocon" was selected with heating up 1.7-2.5 g of PHF to 115° C.

1.3.2. Density

The density of freeze-dried treated PHF and controls was measured by Gas pycnometry with AccuPyc 1330 Pycnometer (Instrumat AG, Switzerland). A known quantity of gas (at known pressure and temperature) was passed through a calibrated reference volume into a calibrated sample cell which contained approximately 2 g of sample. The density was determined by measuring the pressure change of helium in a calibrated volume (10 $cm^3$), based on the ideal gas law.

1.3.3. Particle Size Distribution

Particle Size distribution of freeze-dried treated PHF and controls was measured by laser diffraction using a Malvern Mastersizer 2000 instrument (Malvern, UK) with a small volume dispersion unit containing medium chain triglycerides (MCT) oil. MCT method was used, which used the Fraunhofer diffraction technique to determine the particle size distribution (Lee Black, McQuay, and Bonin, 1996 *Progress in Energy and Combustion Science*, 22(3), pp. 267-306—incorporated herein by reference).

Particle Size distribution of treated PHF dispersions and controls was measured using the same instrument but with a Hydro 2000 SM wet sample dispersion unit containing water.

Refractive index, absorption index and density used were 1.544, 0.1, and 1.5, respectively, which correspond to the values of pure cellulose (provided by Malvern). The analysis was performed in triplicate, with a laser obscuration between 8 and 12%. The obtained size distribution was provided in volume percentage as a function of particle diameter. Average particle sizes are expressed as the surface area based ($d_{3,2}$) and volume based ($d_{4,3}$) mean particle diameters.

1.3.4. Morphology

Confocal Laser Scanning Microscopy (CLSM)

Microstructure of 50% o/w emulsions stabilized with enzymatically treated PHF and controls was imaged using CLSM. For this analysis emulsions were prepared with milli-Q water instead of citrate-phosphate buffer as the Fluorescein showed reactivity towards the buffer. The water phase of the samples was stained by 0.01 wt % Fluorescein sodium (Merck, Germany). The oil phase was stained diluting 100 times a Nile red stock solution (Sigma, United states) of 0.25 mg/100 mL EtOH. Samples were deposed inside a 1 mm deep plastic chamber closed by a glass slide coverslip to prevent compression and drying artefacts. Imaging was done at room temperature with a LSM 710 confocal microscope upgraded with an Airyscan detector (Zeiss, Germany). Acquisition and image treatments were done using the Zen 2.1 software.

Acquisitions parameters for Fluorescein:

Excitation wavelength: 488 nm; Emission: BP=420-480 nm and BP=495-550 nm

Acquisitions parameters for Nile red:

Excitation wavelength: 561 nm, Emission: BP=570-620 nm and LP=645 nm

Scanning Electron Microscopy (SEM)

Treated PHF after freeze-drying and commercial reference PHF fibres were analysed with SEM. Powders were glued onto a metallic specimen stub equipped with a double-sided conductive tape. The stub was shaken to allow a good spreading of the powder. The samples were coated with a 10 nm gold layer using a Leica SCD500 sputter coater and were subsequently imaged in a low vacuum mode at 6 kV using a Quanta F200 Scanning Electron Microscope (FEI, The Netherlands).

Wet samples were installed onto a metallic specimen stub equipped with a double-sided conductive tape. The stub was placed on a Pelletier stage maintained at 4° C. Images were recorded using a Gaseous Secondary Electron Detector in a Quanta F200 Scanning Electron Microscope operated at 10 kV. Microscope pressure was set at 4.60 Torr which corresponds to a relative humidity of 75% in order to visualize the sample in a hydrated state.

Light Microscopy

Microstructures of 50% o/w emulsions and of 10% w/w PHF dispersions and controls were imaged using light microscopy. A drop of sample was placed on a glass plate and imaged with an Olympus SZX16 light microscope (Olympus, Germany) equipped with a digital camera and imaging software (cellSens), using dark field illumination and appropriate magnification.

1.3.5. Surface Charge

A Zetasizer nano series instrument (Malvern, UK) was used to determine electrophoretic mobility of enzymatically treated PHF and controls in water (1% w/v), which was subsequently translated into the zeta potential. The optimum size range of particles in solution for the zeta potential measurement was from 5 nm to 10 μm, therefore the PHF (size >10 μm) were not suited for this analysis, as they sedimented out in the cuvette during the measurement. This method could be potentially improved by filtering the particles to size ranges of at least 1-10 μm.

1.3.6. Wetting Properties

A KSV CAM200 goniometer (Biolin Scientific, Finland) was used to study the wettability of the dry PHF. A drop of water or oil (3-5 μl) was deposited on a flattened fibre surface with a syringe mounted to the goniometer set up. The change in contact angle over time was recorded under high contrast, and the contact angle was calculated with an image analysis programme that approximates a circle from the droplet shape, and obtains the contact angle from the slope of this curve where this circle intersects the baseline (Mitchell et al., 2017 *Chemical Engineering Science*, 167, pp. 29-41—incorporated herein by reference).

Three different techniques were used to create a flattened surface of the pea hull fibres:

Tableting: 2 g of powder were compressed between two punches at 20 t pressure in a tablet mold made of stainless steel with a diameter of 24 mm.

Spin-coating: A 10-20% TS fibre solution was prepared and stirred for one hour. A small drop was deposited on a glass plate in the center of the spin-coater and was rotated at different speeds by centrifugal force such that a thin layer could be produced.

Fixing fibre powder on tape: 20 mg of fibre were spread over a tape with a spatule that was fixed to a microscopic glass plate.

1.4. Oil-in-Water-Emulsion Stabilization Properties

1.4.1. Preparation of Emulsions

Unless stated otherwise, 50% w/w o/w emulsions were prepared as follows: First 10 mL 100 mM citrate-phosphate buffer pH 5 (with 0.04% w/w $NaN_3$ as antimicrobial agent) was added to a Pyrex tube and mixed with 1 mL of treated or control dispersions. 10 mL of high oleic sunflower oil (Nestrade, Switzerland) were added to the water phase and the emulsion was manually shaken for 10 seconds. Samples were kept at room temperature for a period of 4 weeks, unless stated otherwise.

In order to assess the emulsion stabilizing effect of the soluble phase, 2 mL of PHF dispersion were centrifuged in a 2 mL Eppendorf cuvette at 16,000×g for ten minutes. 1 mL of the supernatant instead of the PHF dispersion was added to the water phase of the 50% o/w emulsions. To assess the emulsion stabilizing effect of the insoluble phase, the pellet obtained after centrifugation was washed 3 times with the citrate-phosphate buffer to remove any remaining soluble components and the PHF dispersion was then reconstituted with the washed PHF to the same concentration by filling up the Eppendorf cuvette with citrate-phosphate buffer until the 2 mL mark again, assuming that the amount of PHF lost during washing is negligible. 1 mL of the washed pellet in citrate-phosphate-buffer was added to the water phase of the 50% o/w emulsions as described above.

1.4.2. Stability of Emulsions

The stability of the emulsions against collapse was assessed visually for at least 4 weeks, unless stated otherwise. Different microscopy techniques (1.3.4.) were used to elucidate the stabilization mechanism of enzymatically treated (functionalised) PHF.

1.4.3. Kitchen Prototypes

Emulsion stabilizing properties of functionlised (enzymatically treated) PHF were tested in liquid creamer prototypes. 250 mL of a 10% w/v dispersion of PHF in PANNA water was prepared and stirred for 1 hour at room temperature to allow full hydration. 240 μL Cell/g PHF and 120 μL Pec/g PHF were added to the dispersion. The dispersion was incubated overnight (16 hours) at 50° C. under continuous stirring, without adjustment of pH (pH measured at 21° C. before reaction: 5.98).

Formulations of the creamer prototypes and results are shown in Example 2.

First, all water-soluble ingredients were dissolved in PANNA water by stirring the mixture in a 200 mL plastic beaker covered with paraffin for two hours at room temperature. Afterwards, the water phase was added a 500 mL plastic beaker containing pre-weighted high oleic sunflower oil. The mixture was homogenized with an IKA Ultra-turax (IKA, Germany) at 16,000 1/min for 2 minutes.

Soluble coffee (2.5 g Nescafé Gold coffee/150 g water) was dissolved in PANNA water at 80° C. 5 g of liquid creamer was added 30 mL of coffee and kept in an oven at 70° C. until tasting for maximum one hour. Samples were mildly stirred with a plastic spatula before tasting and served under red light for colour masking. A control (same as the reference) was served in order to test reproducibility of the sensory evaluation.

1.5. Analytical Methods

1.5.1. Determination of Enzyme Protein Content

Protein content of purified enzymes and commercial enzyme cocktails was determined with the Bradford and Lowry assay according to Sigma's protocol (Sigma Aldrich, Switzerland).

Bradford

100 µl of Bradford reagent (Sigma Aldrich, Switzerland) was added to 100 µl of samples in a Nunc MicroWell 96-Well Microplate (Thermo Scientific, Switzerland). Appropriate dilutions of samples were prepared in milli-Q to obtain concentration within the linear part of the calibration curve. The solutions were left to react for 5 minutes at room temperature after which the absorbance of the standards and samples were determined at a wavelength of 595 nm using a Varioskan Flash (Thermo Scientific, Switzerland). A calibration curve with bovine serum albumin (BSA, Sigma, Switzerland) was prepared with concentrations ranging from 0 to 25 µg/mL.

Lowry

100 µl of Lowry reagent solution was added to 100 µl of samples in a Nunc MicroWell 96-Well Microplate (Thermo Scientific, Switzerland). The solutions were left to react for 20 minutes at room temperature, after which 50 µl of Folin & Ciocalteu's phenol reagent was added to each well and allowed to develop color for 30 minutes at room temperature. The absorbance of the samples was determined at a wavelength of 600 nm using a Thermo Scientific Varioskan Flash (Thermo Scientific, Switzerland). A calibration curve with bovine serum albumin (BSA) was prepared with concentrations ranging from 0 to 400 µg/mL.

1.5.2. SDS-PAGE

SDS electrophoresis was performed on the soluble and unsoluble phase of PHF dispersions after incubation. Samples for SDS analysis were prepared as follows. PHF dispersions were centrifuged in a 2 mL Eppendorf cuvette at 16,000 xg for 10 minutes after which the supernatant was separated from the pellet (supernatant 1). The pellet was dissolved in Tris-SDS-Urea buffer pH 8.5 in the same Eppendorf cuvette for at least 10 minutes, after which the mixture was centrifuged, and the supernatant was separated from the pellet (supernatant 2). Supernatant 1 and supernatant 2 were used to analyse the proteins present in the soluble and in the unsoluble phase respectively. Controls were prepared with PHF dispersions that were incubated with deactivated enzymes and no enzymes.

25 µL NuPAGE LDS sample buffer (Invitrogen, Switzerland) and 10 µl NuPAGE Sample Reducing Agent (Invitrogen) were added to 65 µL of sample and then heated at 70° C. for 10 minutes in a Thermomixer (Thermo Scientific, Switzerland, Switzerland).

Gels were rinsed three times with NuPAGE MOPS SDS running buffer and placed into X-CELL II Mini Cell (LifeTechnologies, Switzerland). The samples were then loaded into wells on the NuPAGE Novex 12% Bis-Tris Gel (Invitrogen, Switzerland), and a molecular weight marker (Sigma Aldrich, Switzerland) was loaded into well 1 and 12. NuPAGE LDS sample buffer was loaded into empty wells. Both chambers of the electrophoresis cell were filled with NuPAGE MOPS SDS Running Buffer (Invitrogen, Switzerland) and 500 µl of NuPAGE Antioxidant (Invitrogen, Switzerland) was added to the buffer in the upper chamber. The electrophoresis was carried out in an X-CELL II Mini Cell at 200 V for 50 minutes. The gel was then incubated in 100 mL fixing solution (50% methanol, 10% acetic acid and 40% milli-Q water) in a plastic container for 10 minutes at room temperature with gentle shaking. After 10 minutes the container was emptied and filled with the staining solution (55% mL milli-Q water, 20 mL methanol, 20 mL stainer A from colloidal blue staining Kit (Invitrogen, Switzerland)). The gel was incubated for another 10 minutes, after which 5 mL of Stainer B from the colloidal blue staining Kit were added (Invitrogen, Switzerland). The gels were stained for 3-4 hours. Staining solution was removed and 200 mL milli-Q water were added and gently shaken for at least 7 hours to allow decolorization. The gels were scanned with a Image Scanner III (GE Healthcare, Life Sciences, Switzerland) using white background screen.

1.5.3. Reducing Sugar Analysis

Reducing sugars in reaction supernatants and controls were measured with DNS method. DNS reagent was prepared by mixing 200 mL of 8% w/v NaOH (Merck, Switzerland) with 500 mL milli-Q water, followed by the addition of 10 g of 3,5-dinitrosalicylic acid (DNS). 402.7 g of $C_4H_4KNaO_6 \times 4H_2O$ were slowly added under continuous stirring.

125 µl of DNS solution was added to 125 µl of the sample and the mixture was boiled for 5 minutes. 1 mL of milli-Q water was added and absorbance was read at 540 nm using a Unicam UV-visible spectrometer (Helios Gamma, Helios Delta, UK). Standard curves were prepared using glucose, xylose, and D-galacturonic acid at concentrations varying between 0 and 2 mg/mL.

1.5.4. Qualitative Analysis of Oligosaccharides Using Hydrophilic Interaction Chromatography (HILIC)

Reaction supernatants of PHF treated with commercial enzyme cocktails were analysed using HILIC.

Maltotriose standards (2 µmol/mL, 0.5 µmol/ml and 0.1 µmol/mL) and a laminaritriose internal standard working solution (0.4 µmol/mL) were prepared. 2AB labeling reagent was prepared by adding 524.2 mg of anthranilamide (Sigma-Aldrich, Switzerland) and 691.2 mg of sodium cyanoborohydride (Sigma-Aldrich, Switzerland) in a solution of 3.6 ml of anhydrous acetic acid (Merck, Switzerland) and 8.4 ml of dimethyl sulfoxide (Sigma-Aldrich, Switzerland). The 2AB labeling reagent was then mixed on a vortex and put in an ultrasonic bath for 10 minutes for complete dissolution. Eluent A, water—acetonitrile 25:75 solution, was prepared by mixing 250 ml of Milli-Q water and 750 ml of acetonitrile (Merck, Switzerland). Eluent B, ammonium formate 50 mM, was prepared by adding 1.89 ml of formic acid 100% (Merck, Switzerland) in 800 ml of Milli-Q water, and by then adjusting the pH to 4.4 with ammonium hydroxide 25% (Merck, Switzerland).

Samples of interest were diluted 20 to 100 times in Milli-Q water. 50 µL of aminartriose internal standard working solution (0.4 µmol/mL) was added to 50 µL of the diluted samples and maltotriose standards. 20 µL of each mixture was transferred into a 2 mL microtube and to which 200 µl of the 2AB labelling reagent was added. After mixing with a vortex mixer, the tubes were incubated at 65° C. for 2 h in a water bath. After this labeling reaction, the tubes were kept at 4° C. for 10 min. Each of the mixtures was then diluted with 0.6 mL of eluent A, vortexed and then transferred quantitatively into 2 ml chromatography vials (Agilent, Switzerland) and screwed shut with preslit caps (Agilent, Switzerland).

The analyses were carried out on a Thermo Scientific Vanquish UHPLC system (Thermo Scientific, Switzerland). Using an injection volume of 2 µL, the oligosaccharides were separated on a ACQUITY UPLC BEH Amide Column (130 Å, 1.7 µm, 2.1 mm×150 mm, Waters, Switzerland) with an ACQUITY UPLC BEH Amide VanGuard Pre-column (130 Å, 1.7 µm, 2.1 mm×5 mm, Waters, Switzerland). Eluents A and B were used with a mobile phase flow rate of 0.5 ml/min with a gradient profile consisting of eluent A with the following proportions (v/v) of eluent B: 0-2.3 min, 5% B; 2.3-2.5 min, 5%-10% B; 2.5-4.9 min, 10% B; 4.9-65 min, 10%-22% B; 65-65.5 min, 22%-70% B; 65.5-68 min, 70% B; 68-69 min, 70%-10% B; 69-74 min, 10% B; 74-75.5 min, 10%-5% B. The column chamber was heated and maintained at 60° C. for the duration of the analyses. A Vanquish Fluorescence Detector F (Thermo Scientific, Switzerland) was used with an excitation wavelength of 330 nm and an emission wavelength of 420 nm, with a sensitivity of 3, and a High Power lamp mode. Chromatograms were plotted and peak areas were analyzed using Chromeleon 7.2 Chromatography Data System software (Dionex, Switzerland).

1.5.5. Quantitative Analysis of Mono- and Oligosaccharides Using High Performance Anion Exchange Chromatography (HPAEC)

Reaction supernatants of PHF treated with commercial enzyme cocktails were analysed using HPAEC.

Mono- and Oligosaccharides

Mono- and oligosaccharides were analyzed using a Dionex ICS-3000 DC apparatus equipped with a CarboPac PA1 column (Dionex Corporation, 2010) with a temperature set at 30° C. and gold triple potential pulsed amperometric detection (PAD). Eluent A (100 mM aqueous NaOH) and eluent B (600 mM sodium acetate in 100 mM aqueous NaOH) were used as the mobile phase with a sodium acetate gradient as follows: 0-5 min, 0 mM; 5-50 min, 0-48 mM; 50-55 min, 48-600 mM; 55-65 min, 600 mM; 65-68 min, 600-0 mM; 68-75 min, 0 mM at a flow rate of 1.0 mL/min. The applied PAD potentials for E1 (400 ms), E2 (200 ms), and E3 (400 ms) were 50, 750 and −150 mV respectively and the output range was 1 µC. The injection volume of each sample was 20 µL injected by Dionex AS autosampler (temperature set at 10° C.). Samples were diluted 100× and filtered (0.2 µm). Standards with cellobiose, -triose, -tetraose and -pentaose were prepared in three different concentrations (25 µg/mL, 75 µg/mL and 150 µg/mL, linearity confirmed). Chromeleon™ 7.1 version chromatography software was used to acquire and process chromatographic data.

Monosaccharide Analysis

A carbohydrate standard stock solution was prepared by dissolving 100 mg of glucose (Sigma-Aldrich, Switzerland), mannose (Merck, Switzerland), arabinose (Sigma-Aldrich, Switzerland), xylose (Sigma Aldrich, Switzerland), galactose (Sigma Aldrich, Switzerland) in 100 ml of Milli-Q water, in a 100 ml volumetric flask, resulting in a solution with a concentration of 1000 µg/mL for each monosaccharide. From this stock solution, a series of standards, of 500 µg/mL 250 µg/ml, 100 µg/mL, 25 µg/mL, 5 µg/mL, 2.5 µg/mL and 0.5 µg/LI, were prepared. 1.5 mL of standards and 100× diluted samples were filled into 2 mL chromatography vials (Agilent, Switzerland) and screwed shut with preslit caps (Agilent, Switzerland).

The analyses were carried out on a Thermo Scientific Dionex ICS-5000+ Reagent-Free HPIC system (Dionex, Switzerland). Using an injection volume of 25 µL, the monosaccharides were separated on a CarboPac PA1 column (4×250 mm, Dionex, Switzerland). Eluent A was 300 mM sodium hydroxide (J. T. Baker Chemicals, Switzerland) and eluent B was Milli-Q water with a mobile phase flow rate of 1 mL/min with a gradient profile consisting of eluent A with the following proportions (v/v) of eluent B: 0-60 min, 100% B; 60-75 min, 0% B; 75-90 min, 100% B. A post column eluent of 300 mM sodium hydroxide was added at a flow rate of 0.6 mL/min to increase the signal strength and reduce the signal to noise ratio. A Dionex ICS-5000+ ED40 Electrochemical Detector (Dionex, Switzerland) equipped with a gold working electrode was used with pulsed amperometry detection using pulse parameters of a Carbo Quad waveform. Chromatograms were plotted and peak areas were analyzed using Chromeleon 7.2 Chromatography Data System software (Dionex, Switzerland).

Results 2.1. Characterisation of Purified Enzymes and Commercial Fibre-Degrading Enzyme Cocktails The protein contents of purified enzymes and commercial enzyme cocktails measured with Lowry and Bradford standard assays is shown in FIG. 1. Regardless the assay chosen, commercial enzyme preparations had significantly higher protein contents (19.1-182 mg/mL enzyme solution) compared to the purified enzymes (0.2-1.0 mg/mL enzyme solution). Protein contents measured by Lowry were consistently higher than those measured with Bradford. The differences can be explained with differences in assay sensitivity towards certain peptides or other compounds present in the enzyme solution (Berges, Fisher and Harrison, 1993). Although Lowry is generally accepted as the more accurate method for protein quantification (Redmile-Gordon et al., 2013 *Soil Biology and Biochemistry*, 67, pp. 166-173), it showed high reactivity towards purified ß-glucosidase (E-BGLUC). Therefore, Bradford method was employed to normalize enzymes by protein content.

Endo-Glucanase, Endo-Xylanase, β-Glucosidase and Pectinase Activity

Activity of purified enzymes and commercial enzyme cocktails is shown in table 4. Commercial enzyme preparations had much higher activities (9748-10467 U/mL) than the purified enzymes (182-3844 U/mL). However, the specific activity of the purified enzymes showed significantly higher activities compared to commercial enzyme cocktails. It is important to mention that these values are only valid under given assay conditions.

TABLE 4

Enzyme activities (cellulase, xylanase, pectinase and β-glucosidase) of purified enzymes and commercial enzyme cocktails.

| Enzyme | Measured activity | Enzyme activity (U/mL enzyme solution) | Specific activity[b] (U/mg protein) |
| --- | --- | --- | --- |
| E-CELAN | Endo-glucanase | 2192.02 | 12,177.9 |
| E-XYAN4 | Endo-xylanase | 3843.93 | 20,890.9 |
| E-BGLUC | β-glucosidase | 182.93 | 223.1 |
| Celluclast 1.5 L | Endo-glucanase | 10,467.92 | 104.4 |
| Pectinex SP-L | Endo-polygalacturonanase | 9748.75 | 510.4 |

[b]Based on Bradford data (FIG. 1)

Proteolytic activity in commercial enzyme cocktails and in PHF is shown in table 5. The purpose of this measurement was to confirm or disprove the presence of proteolytic activity that could act against pea proteins or enzymes present in the reaction solution. Pectinex Ultra SP-L had proteolytic activity while this activity was absent for Celluclast 1.5 L. Exafine PHF also had significant proteolytic activity. This can be explained by the presence of endogenous enzymes that form typically part of primary cell walls (O'Neill & York, 2003 The composition and structure of plant primary cell wall. In Annual Plant Reviews 8: The plant cell wall, Rose, J K C Ed. Oxford: Blackwall, which is incorporated herein by reference) and have not been deactivated during industrial processing. It must be highlighted that the units were calculated with a standard calibration curve provided by Megazyme (see 1.5.1.) and do not represent total units as our assay conditions were adapted to the usual reaction conditions (pH 5, temperature 50° C.), which differ from conditions used by Megazyme for calibration.

TABLE 5

Endo-protease activity in commercial enzyme cocktails and in PHF.

| Enzyme | Dilution | Time | Activity (U/mLorg) |
|---|---|---|---|
| Alcalase | 40000 | 10 min | 19,199.0 |
| Celluclast 1.5 L | 1 | 10 min | 0.09 |
| Pectinex SP-L | 25 | 10 min | 18.8 |
| Endogenous enzymes in Exafine PHF | 5000 | 24 hours | 1629.1 |

Effect of Enzyme Treatment with Purified Enzymes and Commercial Enzyme Cocktails on the Degree of Hydrolysis of PHF Reducing sugar equivalent concentrations in the control could be explained by soluble oligosaccharides or starch contaminants from the cotyledons that go into solution during incubation.

Next, enzymatic treatments with commercial cellulolytic and pectinolytic enzyme preparations at high doses were performed to ensure more effective hydrolysis. As expected, this treatment markedly increased the degree of hydrolysis compared to purified enzymes, as shown by the increased number of released reducing ends (46.3-75.4 g/L, table 6). The increased fibre hydrolysis can be attributed to both the higher enzyme concentration used and the synergistic effect of several enzymes present in commercial enzyme preparations.

Supernatant Analysis Using HILIC

To gain a better understanding of how the chemical composition of PHF was affected by the enzymatic treatment, the hydrolysates were analysed further using HILIC and HPAEC. This information would allow changes in PHF functional properties to be related to extracted carbohydrates and hence enzymatic activity.

Figure 2:
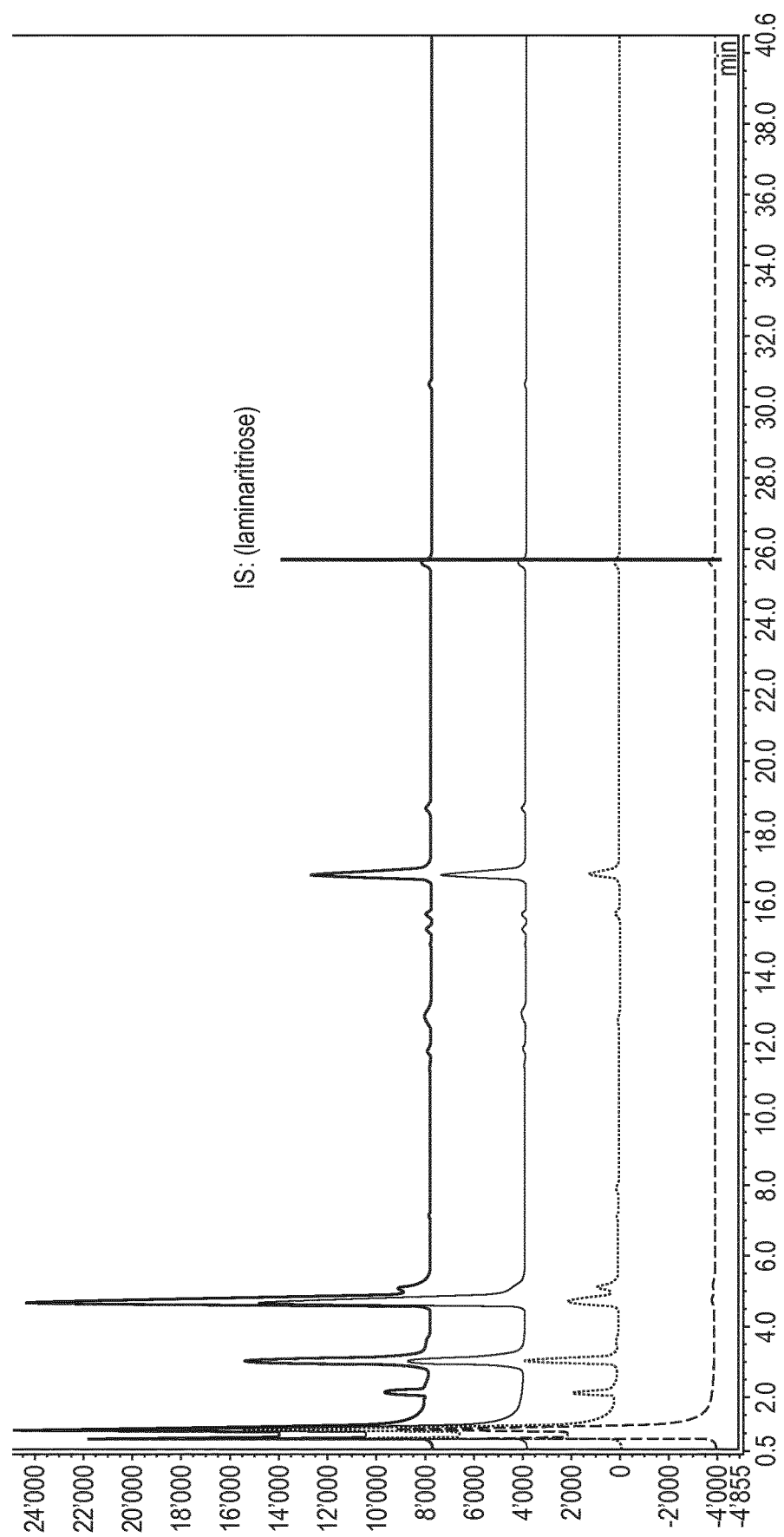
FIG. 2 shows HILIC chromatograms of supernatants from Pea Hull Fibre (PHF) treated with commercial enzyme cocktails. From top to bottom: PHF-Pec+Cell, PHF-Cell, PHF-Pec and Control (dilution 1:100, control 1:10). IS: Internal standard (laminaritriose).

The patterns of enzymatically treated PHF and control are presented in FIG. 2. Results revealed an unexpected presence of low molecular weight material in the supernatant, measured by an early (2-15 min) elution of all components. Although long and later short runs were performed with HILIC at different dilutions, either no or low amounts oligosaccharides (minute 17) were identified in PHF. All spectra, except the control, were composed of the same peaks with differing heights, with the exception of two different peaks at minute 2 and 5 for samples treated with Pec. It can be concluded that low molecular weight fragments were generated as a result of enzymatic action which was mainly driven by cell activity.

TABLE 6

Enzyme doses used for the enzymatic treatment of PHF (10% TS, 16 h, 50° C., pH 5) with purified enzymes and commercial enzyme cocktails including reducing sugars yields for each reaction.

| Sample code | Sample description | Enzyme dose (μL/g PHF) | Units added (U/g PHF) | Reducing sugar (RS) equivalent (g/L)[a] |
|---|---|---|---|---|
| Control | PHF were incubated at the same conditions without the addition of enzymes | — | — | 1.1 |
| PHF-E-CELAN | PHF treated with E-CELAN | 16.6 | 36.4 | 1.6 |
| PHF-E-XYAN4 | PHF treated with E-XYAN4 | 40 | 153.8 | 2.9 |
| PHF-E-BGLUC | PHF treated with E-B-GLUC | 10 | 1.8 | 1.6 |
| PHF-Pec | PHF treated with Pectinex Ultra SP-L | 120 | 1169.9 | 29.3 |
| PHF-Cell | PHF treated with Celluclast 1.5 L | 240 | 2512.3 | 46.3 |
| PHF-Pec + Cell | PHF treated with Pectinex and Cellucast | 120 and 240 respectively | 1169.9 and 2512.3 respectively | 75.4 |

[a]Standard deviation of reducing sugars was below 6% for every sample

Reducing sugar analysis after treatment with purified enzymes indicated that only minor or no new reducing ends were released (1.6-2.9 g/L, table 6). This was expected, as the single action of purified enzymes was not meant to substantially hydrolyse the recalcitrant fibres. However, the low values could also indicate that the inherently heterogenous polysaccharide network was too complex and dense to be degraded by purified enzymes (Huisman, Schols and Voragen, 1999 Carbohydrate Polymers, 38(4), pp 299-307).

Supernatant Analysis Using HPAEC

Compositional analysis of the hydrolysates with HPAEC at different dilution (1:1-1:100) was carried out in order to identify of cello-oligo, di- and monosaccharides. Cello-oligosaccharide analysis did not allow accurate integration, due to co-eluting compounds and poor resolution of peaks. Finally, the monosaccharide analysis of enzymatically treated PHF with the same system allowed a separation of the peaks at 1:100 dilutions, showing that the molecules that eluted early were glucose (26.5-31.4 g/100 PHF dm), arabinose (0.2-3.3 g/100 PHF dm), and xylose (7.6-8.0 g/100 PHF dm). The peak at minute 45 was not identified but could correspond to cellobiose. These molecules are in accordance with the general composition of PHF. Assuming that the glucose mainly originated from the cellulose fraction in PHF (69% w/w dm), it was calculated that approximately 40-48% of the cellulose was degraded to monosaccharides in PHF-Cell and PHF-Pec+Cell.

Results show that the long incubation time coupled with the presence of exo-activities in commercial enzyme cocktails promoted the breakdown of fibres present in PHF to monosaccharides. Presence of exo-activities in Pec and Cell enzyme cocktails were previously reported by Combo et al. (2012) Food and Bioproducts Processing 90(3) p 588-596 (hereby incorporated by reference) and Rosales-Calderon, Trajano and Duff (2014) Peer J. 2 pe402 (hereby incorporated by reference).

Figure 4:
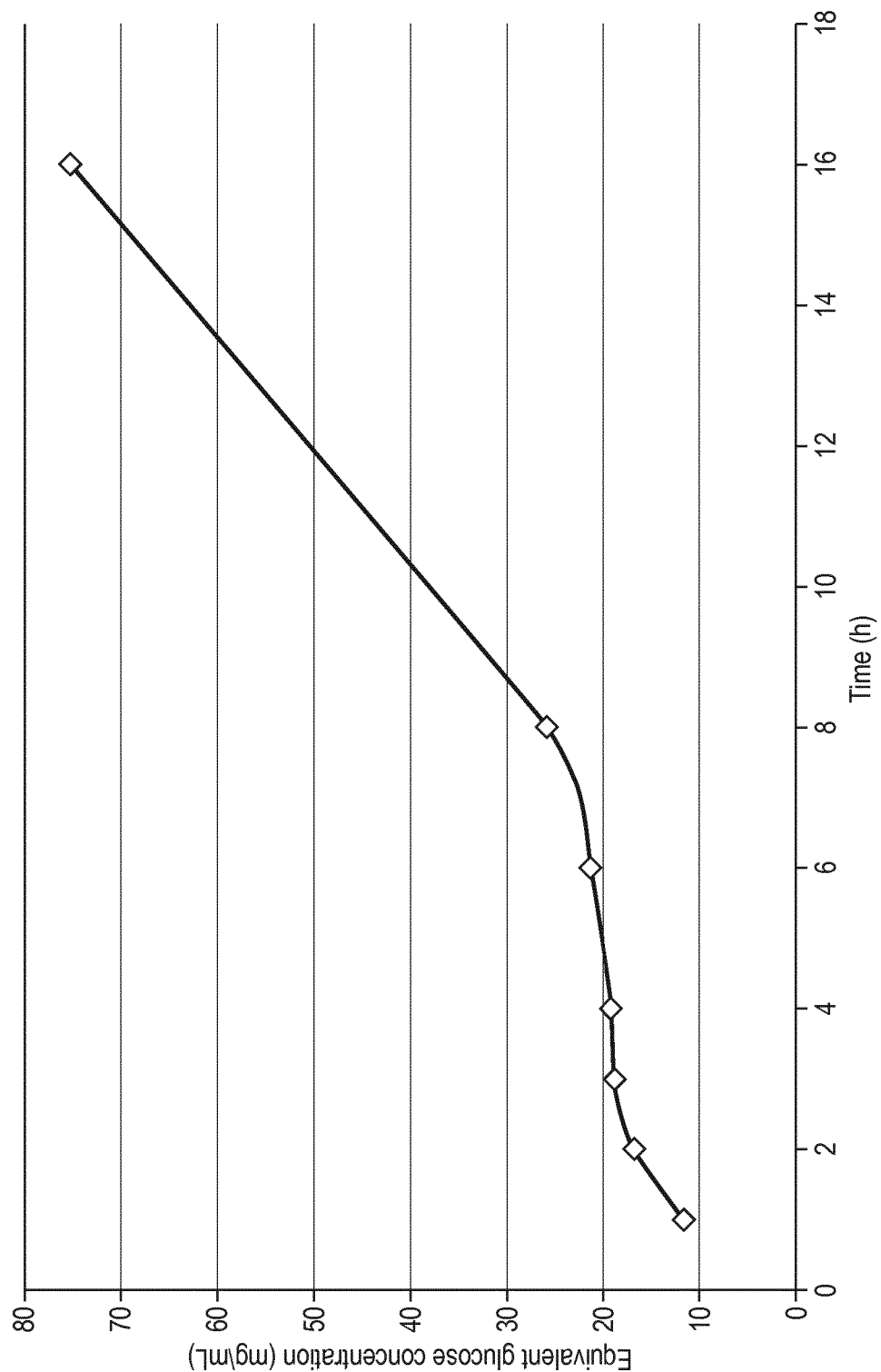
FIG. 4 shows reducing sugar yields in supernatants of PHF-Pec+Cell as a function of reaction time.

When reducing sugars of PHF-Pec+Cell were monitored as a function of reaction time (FIG. 4), primary and secondary hydrolysis processes could be observed. After the first 4-6 hours released reducing sugars reached a plateau. In this step, soluble intermediates from the fibre particles' surface were likely released into the soluble phase (primary hydrolysis) (Sievers et al., 2009 Industrial & Engineering Chemistry Research 48(3) p 1277-1286—incorporated herein by reference). After 8 hours, these long and short chain intermediates were subsequently cut down to monosaccharides by enzymes with exo-activity. This step was much faster than the primary hydrolysis, as shown by the steep increase in slope of reducing sugars from 8 to 16 hours.

Figure 5:
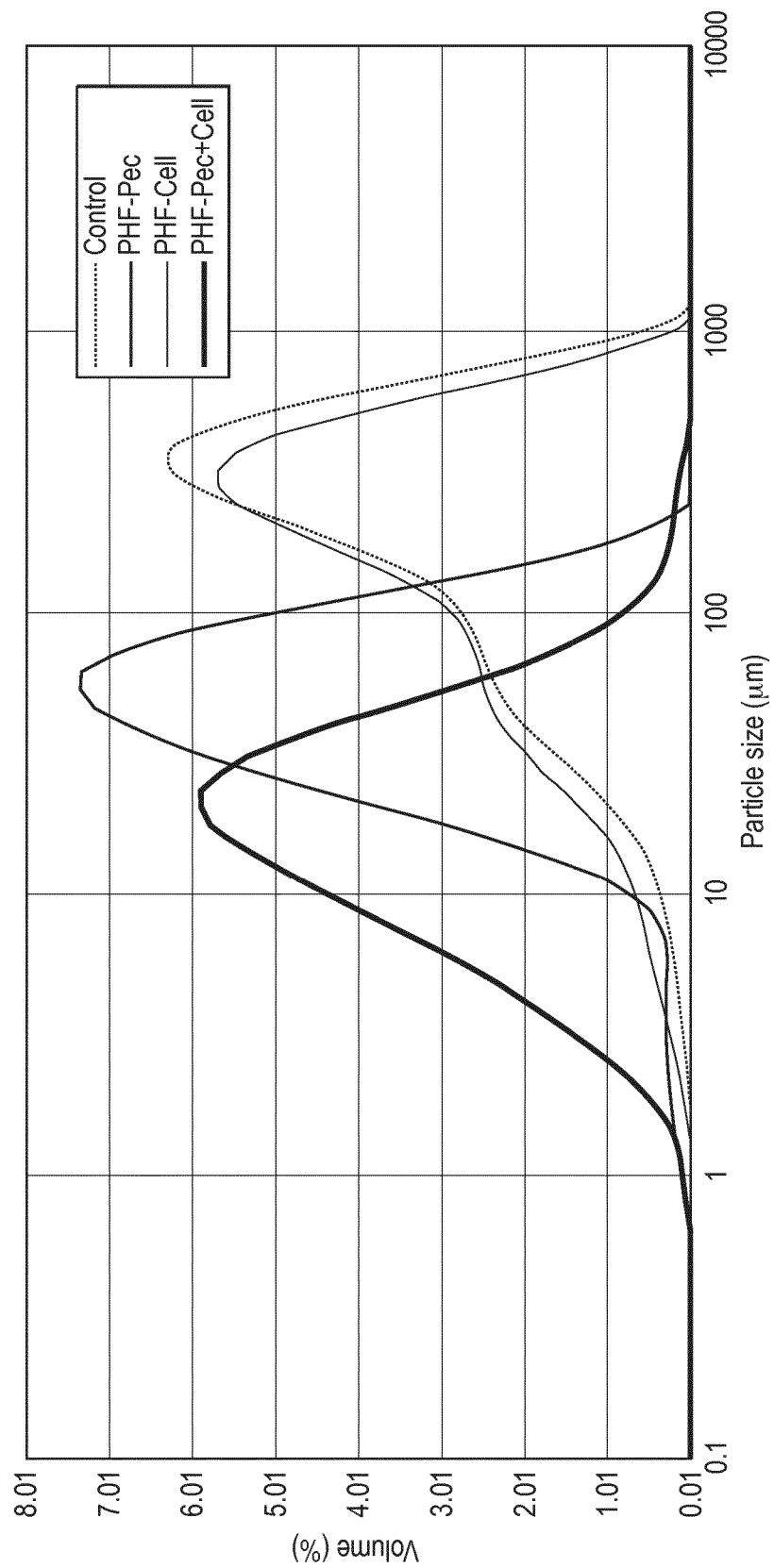
FIG. 5 shows the volumetric particle size distribution of PHF water dispersions treated with commercial enzyme cocktails.

2.2. Functional Properties of Enzymatically Treated Pea Hull Fibres 2.2.1. Enzymatically Treated Pea Hull Fibres as Oil-in-Water Pickering Emulsion Stabilizers Effect of Enzymatic Treatment with Commercial Enzyme Cocktails on Particle Size and Morphology of PHF The volumetric particle size distribution (PSD) for all enzymatically treated samples and the control are depicted in FIG. 5.

The table below corresponds to FIG. 5. The control corresponds to the jet-milled pea hull fibres, where no enzymatic treatment was applied.

|  | D [3, 2]-Surface weighted mean [μm] | D [4, 3]-Volume weighted mean [μm] | d (0.1) [μm] | d (0.5) [μm] | d (0.9) [μm] |
| --- | --- | --- | --- | --- | --- |
| Control (no enzyme) | 65 | 243 | 30 | 202 | 523 |
| PHF-Cell | 42 | 203 | 20 | 160 | 459 |
| PHF-Pec | 22 | 51 | 15 | 43 | 99 |
| PHF-Pec + Cell | 10 | 25 | 4 | 17 | 51 |

One of the effects of enzymatic action on the physical structure of jet-milled PHF was a reduction in particle size leading to particles in a size range of 1 to 300 μm. Smallest particle sizes were obtained when PHF were simultaneously treated with Pectinex SP-L and Celluclast 1.5 L. By applying this treatment, the mean volume diameter was reduced by a factor of ten.

Figure 6:
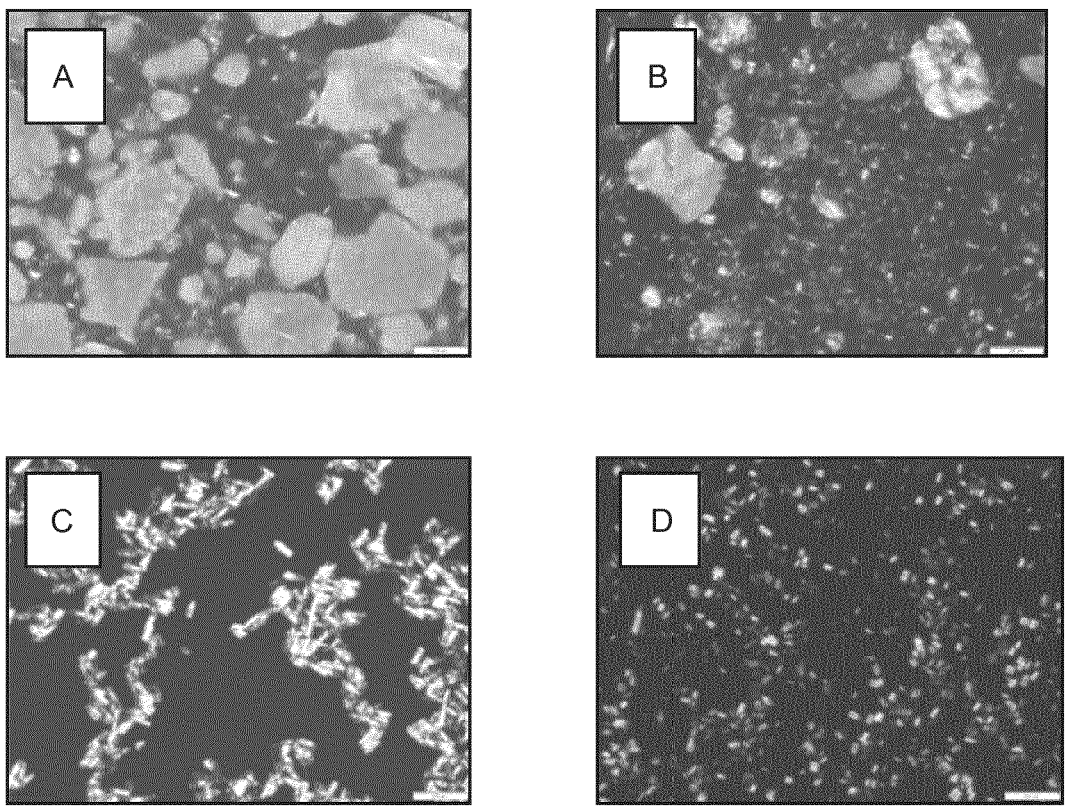
FIG. 6 shows optical micrographs of treated PHF and control after 16 h incubation. A: Control, B: PHF-Cell, C: PHF-Pec, D: PHF-Pec+Cell.

The effects of enzymatic treatment on PHF physical structure were also assessed using optical microscopy. Qualitative analysis of the results indicated changes in particle morphology and size polydispersity as a result of varying the type of enzymatic treatment. Compared to treated PHF, untreated modified PHF particles showed higher polydispersity and increased surface roughness which is not clearly seen from images due to low picture resolution. Treatment of PHF with only pectinolytic enzymes (FIG. 6C) yielded rod-like particles compared to treatment using cellulolytic enzymes (FIG. 6 B, D).

It is important to stress that PSD in FIG. 5 is expressed as a volumetric size distribution. As most of the volume in samples with a polydisperse size distribution is taken up by the larger particles, the relative contribution of smaller particles to the volume distribution decreases, and therefore these small particles are not well-represented by the Malvern measurement. The presence of some large particle in PHF-Cell (FIG. 6, B) could explain why PSD measurement with Malvern Mastersizer 2000 does not show significant changes in particle size for PHF-Cell (FIG. 5), whereas optical micrographs show significant generation of smaller particles (FIG. 6, B).

Figure 7:
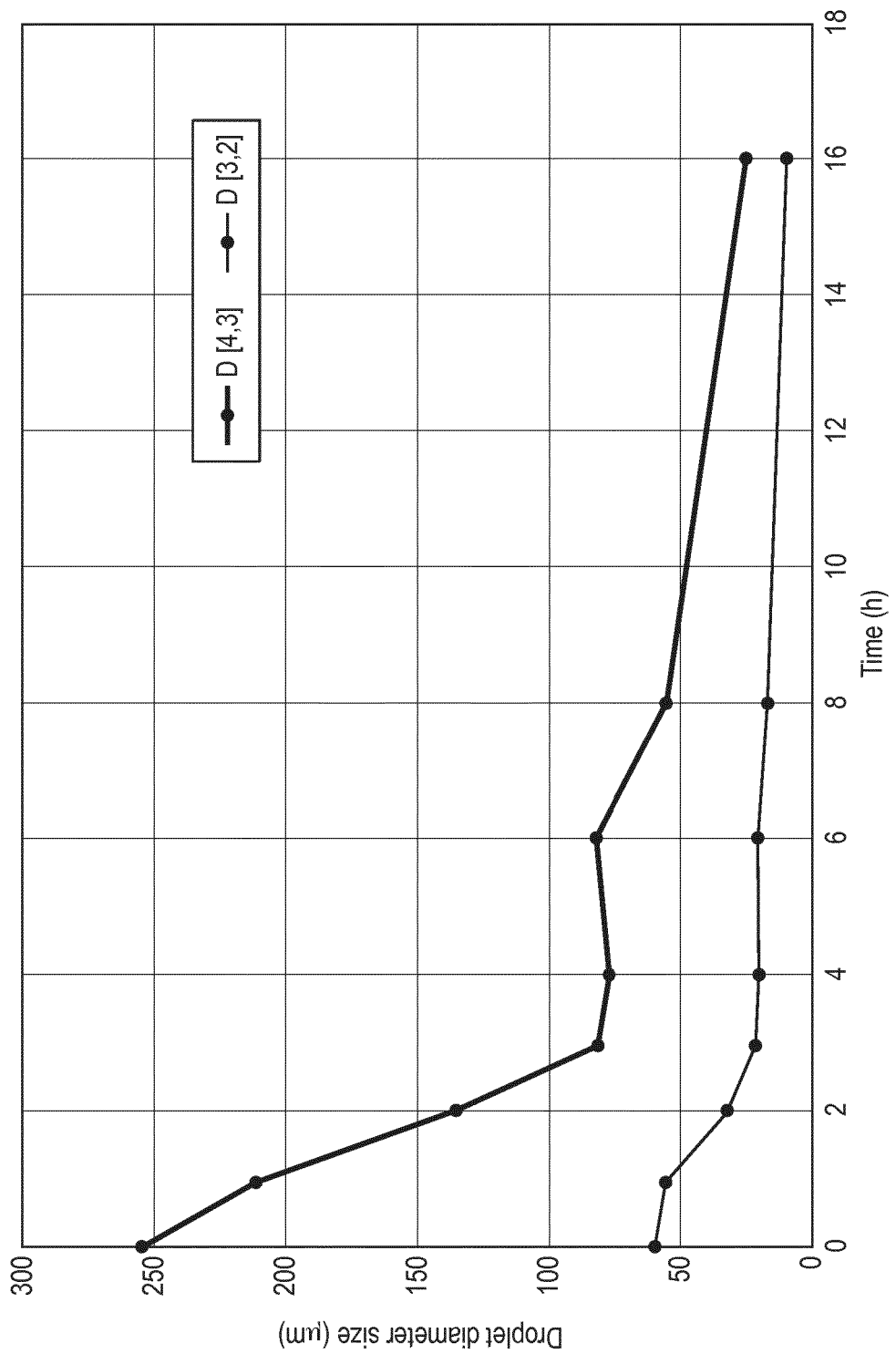
FIG. 7 shows volume based $(d_{4,3})$ and surface area based mean diameter $(d_{3,2})$ as a function of reaction time for PHF-Pec+Cell.

In the graph in FIG. 7 the average particle size of PHF-Pec+Cell as a function of reaction time is presented. The reduction in particle size gradually levelled off after 8 hours. Hence, for future process optimization, reaction time could be reduced to approximately 8 hours without affecting final particle size. This would also limit secondary hydrolysis occur at approx. 6-8 hours, as reported earlier in the discussion (FIG. 4), hence reducing undesired monosaccharide generation.

Effect of Enzymatic Treatment on Shear Flow of PHF Water Suspensions

Figure 8:
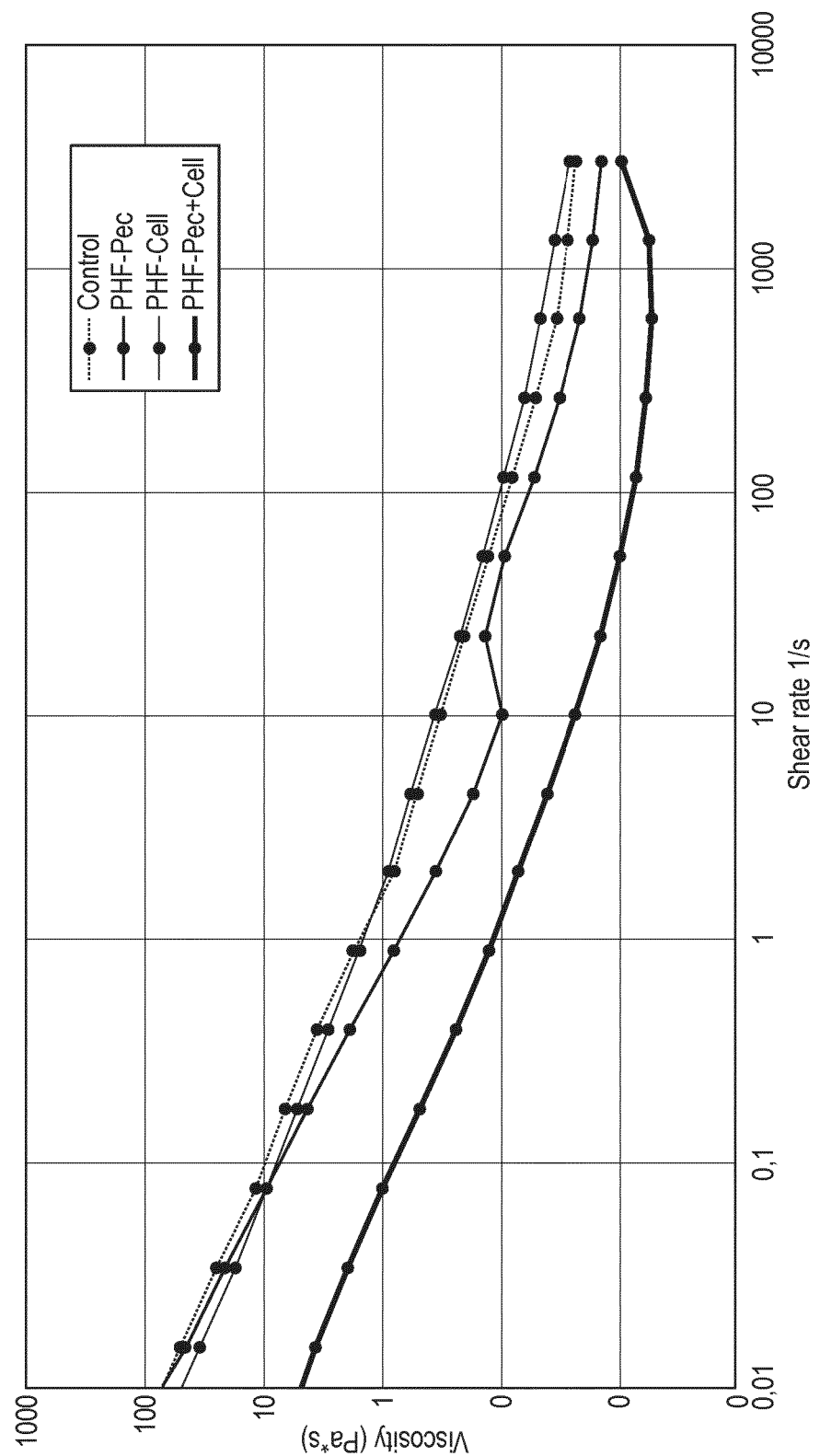
FIG. 8 shows apparent viscosity as a function of shear rate of treated PHF dispersions (10% w/w) and control after 16 h incubation. Measurements were taken at 20° C.

Viscometry measurements were carried out on enzymatically treated PHF water dispersions at 10% w/w after incubation. PHF-Pec+Cell exhibited the lowest viscosity (FIG. 8) values which corresponded to the system with the lowest particle size (FIG. 5). Thus, apparent viscosity seems to be dominated by particulate dispersed phase over the monosaccharide containing water-continuous phase.

For PHF-Cell, no changes in apparent viscosity values were measured, in agreement with the particle size distribution results which show no significant differences. Finally, the measured particle size reduction of the PHF-Pec was not sufficient to significanlty vary the flow response compared to the control.

Effect of Enzymatic Treatment on Wetting Properties of PHF

Assessing the wetting properties of the PHF was a central part of this study, as changing surface hydrophobicity of the otherwise hydrophilic particles was critical to obtain functional particles for emulsion stabilization. Wetting properties are related to the three-phase contact angle θ, which determines the partition of the particles between the two fluid phases.

Figure 9:
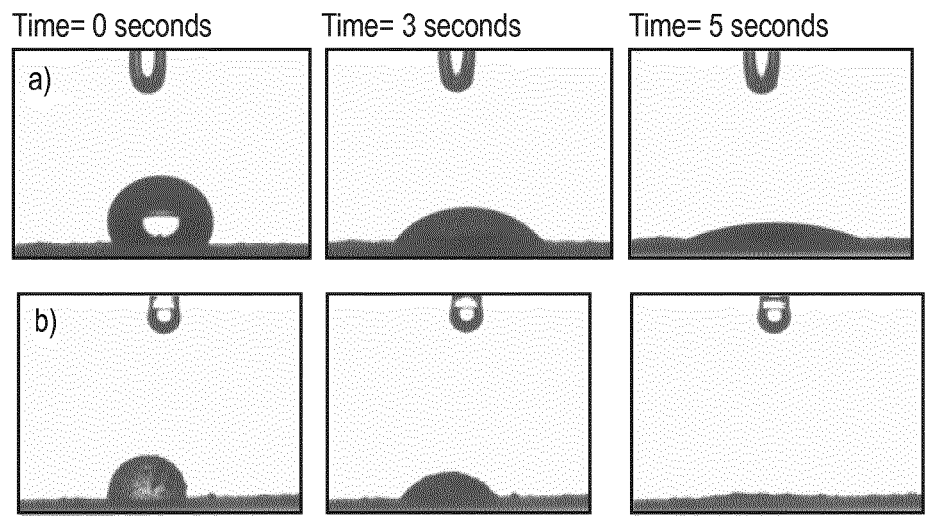
FIG. 9 shows an illustration of contact angle goniometry with a) an oil droplet and b) a water droplet and a PHF surface within the time frame of 5 seconds. In this example, the solid surface was prepared by pressing 20 mg of jet-milled Exafine-PHF on a sticky tape.

Results are shown in FIG. 9.

Accurate determination of the contact angle that a drop of oil or water makes with the PHF was impeded by the porosity of the PHF leading to quick absorption of the fluid in the first 3-5 seconds, a decrease in droplet volume over time, particle swelling upon contact with water and particle uptake by the droplet.

Figure 10:
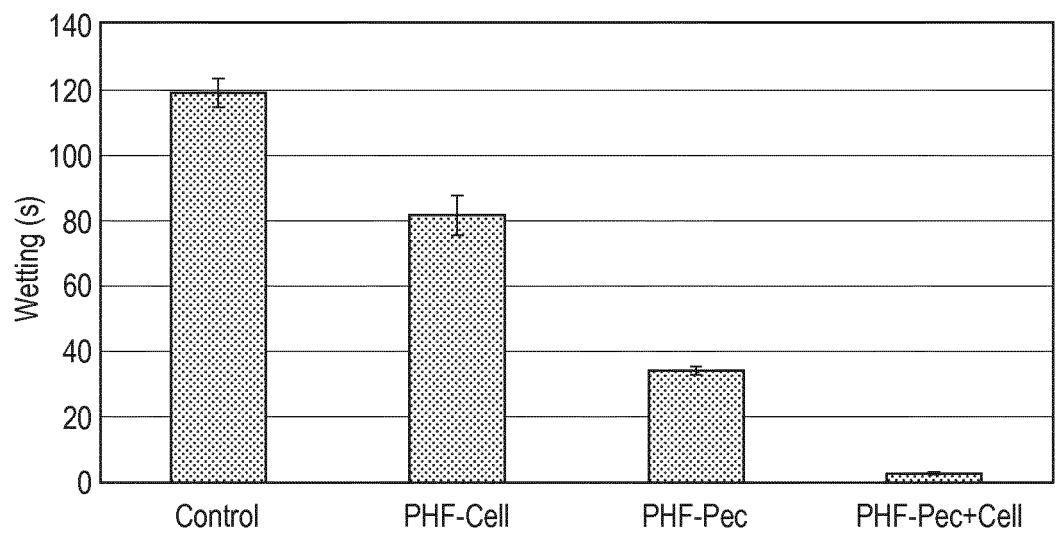
FIG. 10 shows wetting, defined as the time (s) needed for 1 g of powdered enzymatically treated PHF and control to fully immerse into 10 mL of milli-Q water.
Figure 11:
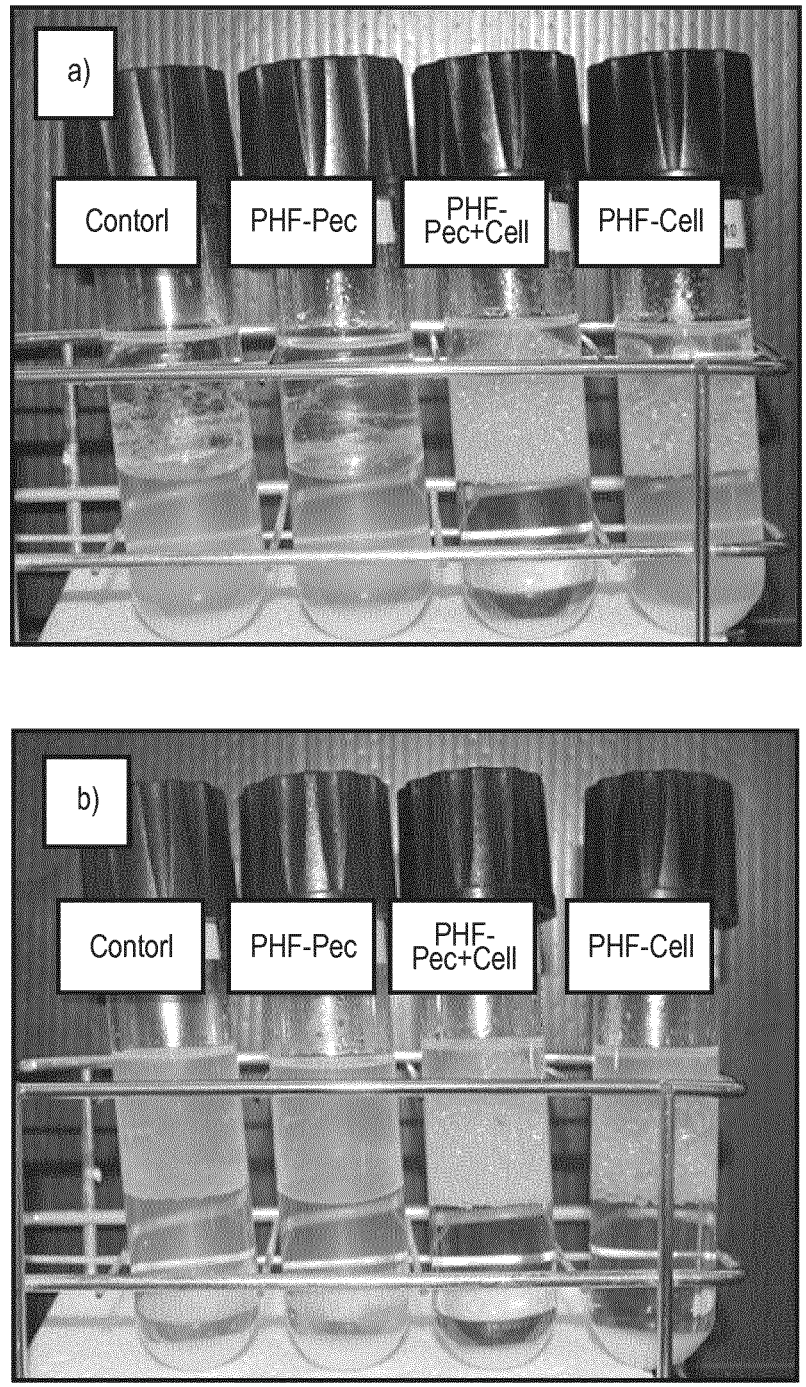
FIG. 11 shows 50% o/w emulsions prepared with 0.4% w/v enzymatically treated PHF (pH 5). Control contained PHF that were treated at the same conditions without enzyme addition a) After one day b) After 4 weeks.

Another method was employed which expressed wettability as the amount of time (s) needed for 1 g of sample to fully immerse into a fixed volume (10 mL) of mili-Q water. For this, the PHF dispersions had to be freeze-dried and powdered. This method showed significant differences between samples and good repeatability (see FIG. 10).

PHF-Pec+Cell showed best wettability, with only 3 seconds needed for full immersion, followed by PHF-Pec and PHF-Cell. Control PHF needed almost 120 seconds to disappear from the surface, and hence were considered the least hydrophilic. However, improved wettability could also be the result of particle size reduction (FIG. 5), leading to more functional groups exposed at the particle surface that were available to bind with water molecules (Einhorn-Stoll, Hatakeyama and Hatakeyama, 2012 Food Hydrocolloids 27(2) pp 494-502, incorporated herein by reference).

Emulsion Stabilizing Properties of Enzymatically Treated PHF

Figure 21:
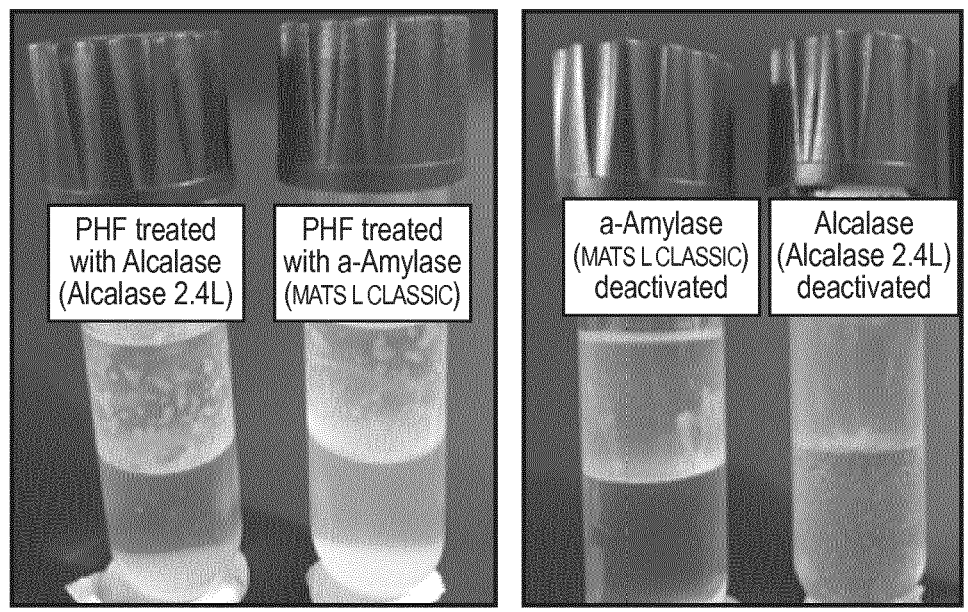
FIG. 21 shows 50% v/v o/w emulsions stabilized with 0.4% w/v PHF treated with Alcalase® and alpha-amylase (left picture) and controls with deactivated alpha-amylase and Alcalase® only (right picture).

Initial emulsions were prepared in a way that would accelerate destabilization, therefore allowing faster comparison between samples. Briefly, 1 mL of treated PHF were first dispersed in the aqueous phase, after which the high oleic sunflower oil was added. The mixture was manually shaken for 10 seconds and the stability of the emulsions prepared with treated fibres was compared to the ones of their non-treated counterpart for a period of four weeks, unless stated otherwise. A picture of the obtained emulsions after 1 day and 4 weeks is shown in FIG. 21.

The low energy input provided by manual shaking contributed to the formation of larger oil droplets and therefore to an increased rate of creaming leading to the formation of a thick creaming layer. After 30-180 seconds the creamed layer of the emulsions prepared with PHF-Pec and the control separated into an oil and a water phase, whereas the droplets (size range between 10-500 μm) in the creamed layer of the emulsion prepared with PHF-Pec+Cell and PHF-Cell remained stable for at least 4 weeks. The same results were observed when emulsions were prepared at pH 3.0, 5.0 and 8.0.

The stability of an emulsion is usually evaluated based on its ability to resist physicochemical changes over storage time (McClements, 2005 Food Emulsions: Principles, Practice, and Techniques. Boca Raton: CRC Press, incorporated herein by reference). Emulsions are considered stable when exhibiting a homogenous appearance with no phase separation. The way in which our emulsions were prepared favoured rapid creaming, hence we based our definition of stability on whether the creamed oil droplets would remain stable over time, irrespective of droplet size or cream layer height. This comparative analysis would only allow two response options, where "stable" refers to the case where creamed oil droplets are resistant to coalescence for at least 4 weeks and "unstable" to the case where no droplets are present.

Figure 3:
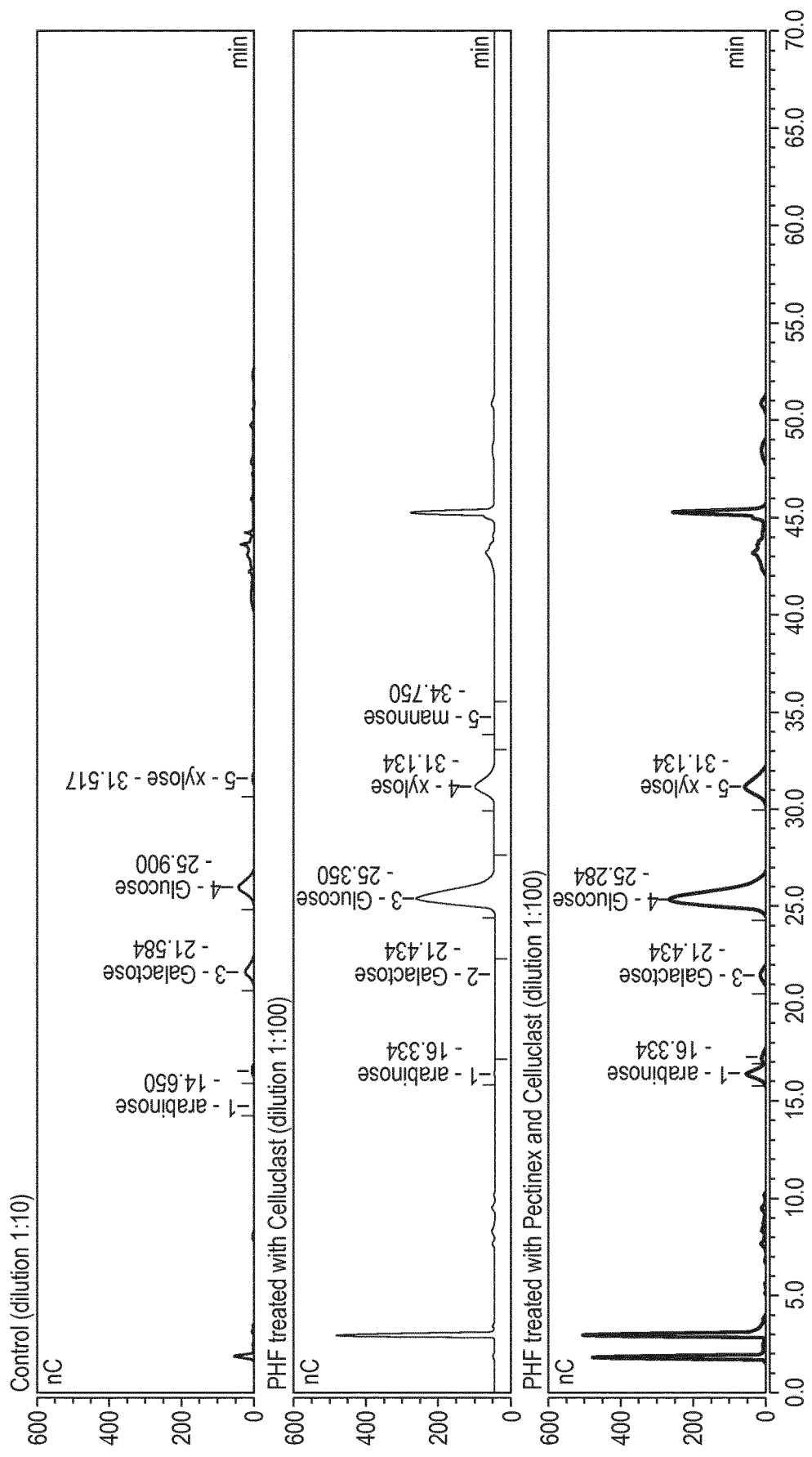
FIG. 3 shows HPAEC chromatograms of supernatants from PHF dispersions treated with commercial enzyme cocktails.
Figure 12:
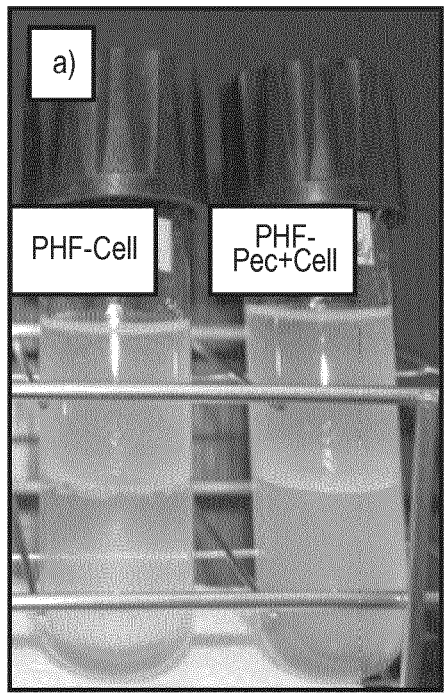
FIG. 12 shows emulsions stabilized with the soluble phase (a), and insoluble phase (b) of PHF-Cell and PHF-Pec+Cell 24 hours after preparation. Emulsions remained visually unchanged for four weeks.
Figure 12:
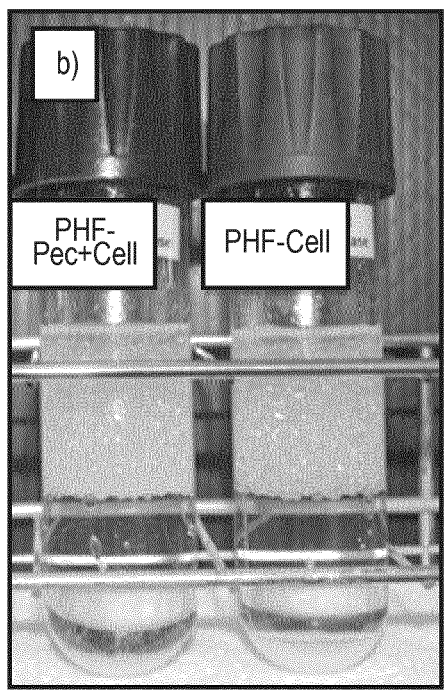

Decoupling the Effect of Soluble and Insoluble Fraction on the Emulsion Stabilizing Properties Further experiments were performed to decouple effects from particles and other potential surface-active compounds in solution. The PHF dispersions (PHF-Cell and PHF-Pec+Cell) were centrifuged and the supernatant and pellet were used separately to prepare emulsions. As shown in FIG. 12, emulsions prepared with the insoluble phase (b) remained stable for at least 4 weeks. Emulsions that were prepared with the soluble phase (a) quickly phase separated (approx. 10 minutes), but slower compared to the control. These results indicated that the emulsion stability was driven by the insoluble particulate phase. This is consistent with the previously reported chemical analysis results (FIG. 3) showing that enzymatic treatment yielded mainly monosaccharides, which do not have surface-activity. Having established which phase was driving the stability, experiments were nevertheless continued using the mixture of both phases.

Microstructure of Emulsions Stabilized with Enzymatically Treated PHF

Figure 13:
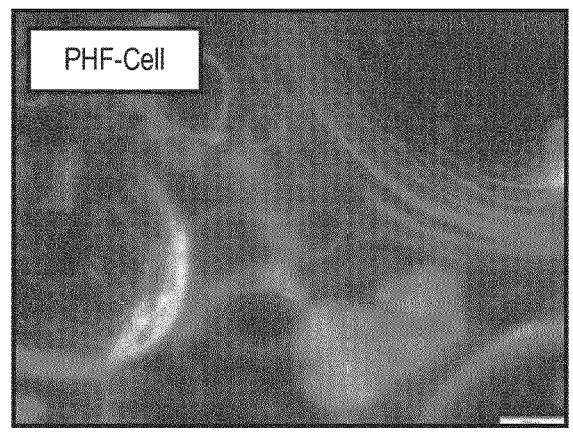
FIG. 13 shows optical micrographs of oil droplets of 50% emulsions prepared with PHF-Cell and PHF-Pec+Cell pH 5 24 hours after preparation. Scale bar: 100 μm.
Figure 13:
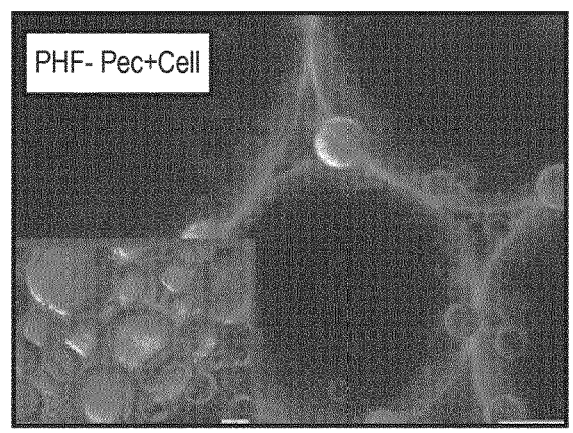

The emulsions were imaged with a light microscope to observe the microstructure of the stable droplets. The micrographs in FIG. 13 show a texturized, rough surface of the droplets, which are a typical feature of liquid surfaces stabilized with particles. Droplets of the control and PHF-Pec were not imaged as they destabilized rapidly after the emulsion was prepared.

Figure 14:
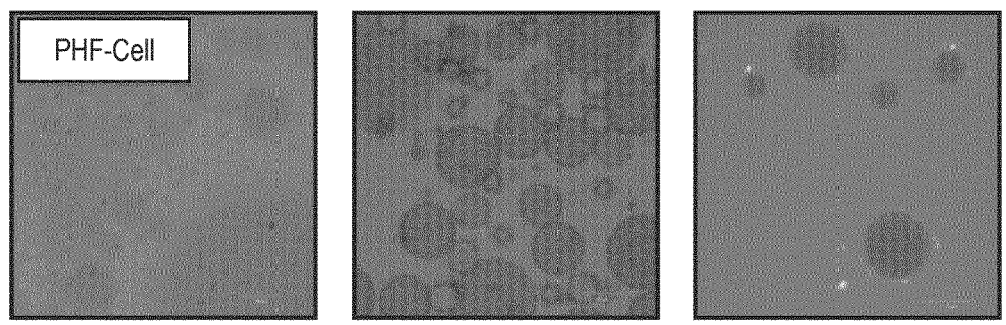
FIG. 14 shows CLSM images of a 50% o/w emulsion stabilized by PHF-Pec+Cell and PHF-Cell (PHF particles appear in yellow). Red and green signal correspond to the oil and water phase, respectively. Emulsions have been prepared before imaging and were aged for at least 24 hours.
Figure 14:
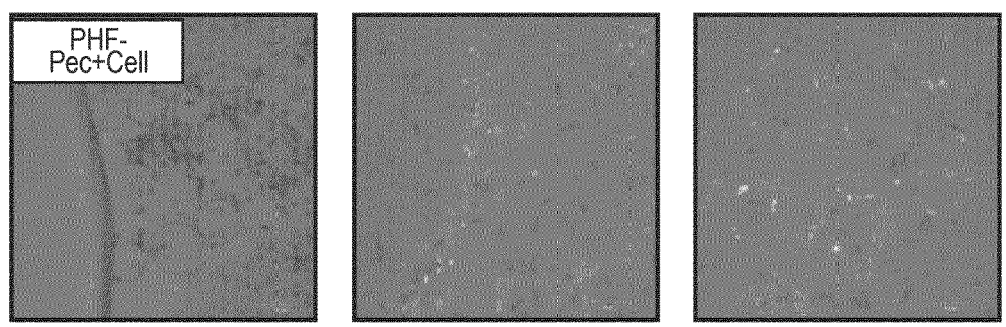

CLSM images of the same emulsions (FIG. 14) showed that small particles (<30 μm) preferred presence at the interface rather than in the bulk of the emulsion, hence had a high affinity for the o/w interface. The obtained emulsions conform to the definition of a Pickering emulsion, where an emulsion is stabilized by the adsorption of solid particles at the o/w interface (Murray et al., 2011 Food Hydrocolloids 25(4) p 627-638, incorporated herein by reference).

Both oil droplets and PHF particles showed dispersity in particle shape and size, but the overall particle to oil size ratio was in the range of 1:10, which is in agreement with the commonly held belief that Pickering particles should be at least one order of magnitude smaller than the oil droplets they stabilize (Berton-Carabin and Schroën, 2015 Annual review of Food Science and Technology 6(1) pp 263-297— incorporated herein by reference). Larger particles (>30 μm) were not able to adsorb at the o/w interface and tended to sediment out of the emulsion. These non-adsorbed particles could play a role in providing additional stability by structuring the continuous phase between the droplets (Gould, Vieira and Wolf, 2013 Food & Function 4(9), p 1369; Tamayo Tenorio et al., 2017 Food Hydrocolloids 71 pp 8-16).

The Pickering effect appeared to be more pronounced for PHF-Pec+Cell than for PHF-Cell. The reason for this is that enzymatic treatment with Pec+Cell generated more small sized particles compared to a treatment with only Cell (FIG. 5), leading to a greater number of particles covering the oil interface. Findings by Gould, Vieira and Wolf, (2013) (supra) also showed that only the small sized particle fraction (<2 μm) from cocoa would adsorb at the surface of oil droplets (with $d_{3,2}$ around 10 μm).

Despite less Pickering particles being present at the o/w interface in emulsions stabilized with PHF-Cell, the same levels of stability were obtained, indicating that other surface-active compounds could be involved in providing additional stability to droplets. It was reported that only a 20% surface coverage of oil droplets by particles is needed to provide effective protection against coalescence for several months (Binks et al., 2005 Naturally Occurring Spore Particles at Planar Fluid Interfaces and in Emulsions. Langmuir 21(18), pp. 8161-8167). However, in the case of PHF-Cell (FIG. 14) some droplets were completely free from particles.

In a first attempt to measure the presence of proteins at the interface, the emulsion was dyed with Fast Green, a colorant that is fluorescent when in contact with proteins, but no signal was obtained. The absence of signal however was not enough evidence to conclude that proteins were not present at interface due to the detection limits at such low concentrations.

Presence of Proteins in the Soluble and in the Insoluble Phase

TABLE 7

Composition of o/w emulsions prepared with enzymatically treated PHF and control. Control was prepared with PHF that were treated at the same conditions without enzyme addition.

| Sample | PHF-Pec + Cell | PHF-Cell | PHF-Pec | Control |
|---|---|---|---|---|
| Emulsion | g | g | g | G |
| Oil | 10 | 10 | 10 | 10 |
| Water | 10.9 | 10.9 | 10.9 | 10.9 |
| Enzyme protein[a] | 0.003 | 0.002 | 0.001 | — |
| Pea protein[b] | 0.005 | 0.005 | 0.005 | 0.005 |
| PHF | 0.09 | 0.09 | 0.09 | 0.09 |
| Other | 0.001 | 0.001 | 0.001 | 0.001 |
| Total | 21 | 21 | 21 | 21 |

[a]Based on Bradford data
[b]Based on Kjeldahl data, taken from RDLS-RD170010-00

Although no proteins were identified with CLSM and the stability of the oil droplets was pH independent, the contribution of proteins could not be ruled out, as they were present in significant amounts (0.8 and 0.7 mg per 1 g oil for PHF-Pec+Cell and PHF-Cell, Table 7). Moreover, only the emulsions with the highest protein contents were stable (Table 7).

Figure 15:
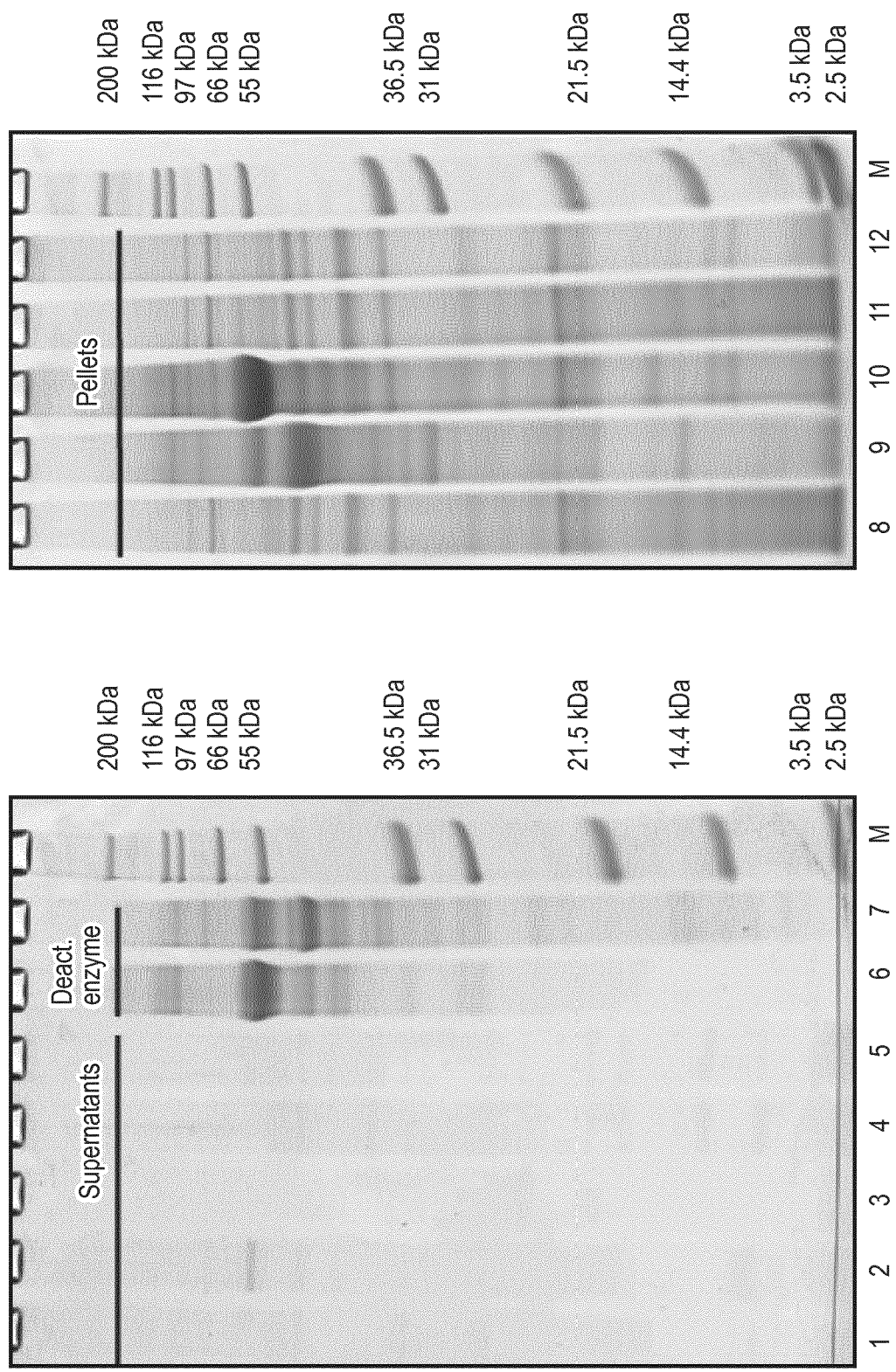
FIG. 15 shows SDS gels of supernatants and pellets from PHF treated with commercial enzyme cocktails.

The soluble (supernatant) and insoluble phase (pellet) of the PHF dispersions (PHF-Cell and PHF-Pec+Cell) were further analysed with SDS-PAGE to determine whether the proteins remained in the soluble or the insoluble fraction (FIG. 15). SDS gels showed that no or only traces of proteins were present in the soluble phase (bands 1-5). SDS analysis of the pellets revealed that almost all available protein remained with the insoluble phase (FIG. 15 band 8-12). Deactivated enzymes that were added to the control before incubation for 16 h were shown as a low molecular weight material in band 8 and 11, probably due to degradation by endogenous enzymes present in PHF. The proteolytic activity by endogenous enzymes in the PHF was previously confirmed by assaying protease activity (Table 7). The active enzymes in their folded form were, apparently, resistant to the proteolytic activity.

To conclude from this experiment, it was shown that the proteins remain with the insoluble phase, hence with the PHF particles, but it is not clear whether both components were associated or present as single components.

TABLE 8

Description of bands from FIG. 15.

| | Sample description |
|---|---|
| 1 | Supernatant, control (no enzymes) |
| 2 | Supernatant, PHF-Cell |
| 3 | Supernatant, PHF-Pec + Cell |
| 4 | Supernatant, PHF-Pec + Cell (control with deact. enzymes) |
| 5 | Supernatant PHF-Cell (control with deact. enzymes) |
| 6 | Deactivated enzyme (Cell) |
| 7 | Deactivated enzyme (Pec + Cell) |
| 8 | Pellet, PHF-Cell (control with deact. enzymes) |
| 9 | Pellet, PHF-Pec + Cell |
| 10 | Pellet, PHF-Cell |
| 11 | Pellet, PHF-Pec + Cell (control with deact. enzymes) |
| 12 | Pellet, control (no enzymes) |
| M | Molecular weight standard |

Elucidating the Role of Enzyme in Stabilization of o/w Emulsion

The clear correlation between enzyme content in the emulsion and stability motivated us to investigate the emulsion stabilizing properties of the enzymes. Enzymes are proteins and could contribute to the emulsifying effect due to their natural amphiphilicity. This hypothesis was tested by preparing control PHF dispersions containing active and deactivated enzymes with and without PHF. For the following experiments we continued using only PHF-Pec+Cell, as this treatment generated more Pickering particles that were of particular interest in this study.

TABLE 9

Overview of experimental conditions for emulsions prepared with active and deactivated enzymes (Pec + Cell).

| Control | pH | Incubation | Heat treatment | Protein concentration from enzyme mg/mL water[a] | Stability |
|---|---|---|---|---|---|
| PHF-Pec + Cell | 5 | 16 h | No heat treatment | 0.51 | Not stable |
| Pec + Cell | 5 | — | No heat treatment | 0.51 | Not stable |
| PHF-Pec + Cell | 5 | — | 100° C. 10 minutes | 0.51 | Stable |
| PHF-Pec + Cell | 5 | 16 h | 100° C. 10 minutes | 0.51 | Stable |
| Pec + Cell | 5 | — | 100° C. 10 minutes | 0.51 | Stable |

[a]Here, protein concentration per mL water phase was estimated from protein content of enzymes provided by the supplier (14% w/w and 7.5% w/w for Cell and Pec, respectively.)

Interestingly, in their active and soluble form the enzymes did not show any emulsifying properties, but when they were subjected to a heat treatment (100° C. 10 minutes) for deactivation, they turned into surface-active agents, and stabilized the emulsion in both the presence and absence of PHF for at least 4 weeks. The outcome of this experiment generated the second main hypothesis of this research, namely that the denatured enzymes drive the emulsion-stabilizing properties.

In this respect, it was also speculated whether direct interactions of enzyme with the PHF particles could be the reason for enhanced functionality of the PHF particles at the o/w interface. Enzymes are catalysts of biochemical reactions and must be in physical contact with their substrate to initiate hydrolysis. The attachment of the enzyme to the substrate is usually mediated through a carbohydrate-binding domain, which consists of several aromatic amino acid sequences (Levy, Shani, and Shoseyov, 2002 *Biomolecular Engineering*, 19(1), pp. 17-30, incorporated herein by reference; Shoseyov, Shani and Levy, 2006 *Microbiology and Molecular Biology Reviews*, 70(2), pp. 283-295 incorporated herein by reference). The association of the CBM to the substrate is established through hydrogen bonding, hydrophobic- as well as weak electrostatic interactions with the carbohydrate and greatly depends on the protein fold (Boraston et al., 2004 *Biochemical Journal*, 382(3), pp. 769-781, incorporated herein by reference). Upon denaturation the enzyme unfolds and loses its tertiary (and often secondary) structure. This phenomenon leads to the exposure of hydrophobic groups at the surface of the protein (Daniel, Dines and Petach, 1996 *Biochemical Journal*, 317 (1), pp. 1-11, incorporated herein by reference). Although the nature of the PHF-enzyme interaction remains unclear, the heat treatment could have potentially imparted conformational changes of the enzyme at the particle surface hence providing particle surface amphiphilicity. This might explain the higher affinity of PHF particles to the o/w interface.

Emulsifying Properties of "Protein-Free" PHF Particles

In order to verify if droplet stability originated mainly from the deactivated enzyme it was necessary to confirm that the modified PHF particles on their own did not exhibit any effect. The main difficulty to proof this lied in providing enzymatically treated particles with no remaining enzyme residues.

TABLE 10

Overview Overview of experimental conditions for emulsions prepared with heat-treated BSA.

| Sample | pH | Incubation time (h) | Heat treatment | Protein concentration in water phase mg/mL | Stable? |
|---|---|---|---|---|---|
| PHF-Pec + Cell, washed | 5 | 16 | No heat treatment | traces | Not stable |
| PHF-Pec + Cell, not washed | 5 | 16 | No heat treatment | 0.51 | Not stable |

Removing the active, soluble enzyme after incubation by washing it with citrate-phosphate buffer at the temperature of incubation (50° C.) represented a good approach to avoid enzyme deactivation after the treatment and obtain particles with similar properties. Furthermore, we showed that the enzymes in their active form did not have emulsifying properties (Table 9). The emulsion was not stable in either of the cases (Table 10). This confirmed that the adsorption of small PHF-particles at the o/w interface is dependent on the presence of deactivated enzymes.

Alternative Protein Sources to Functionalize Particles

TABLE 11

Overview of experimental conditions for emulsions prepared with heat-treated BSA, with and without PHF.

| Sample used to stabilize emulsion | pH | Incubation time (h) | Heat treatment | Protein concentration in water phase mg/mL | Stable |
|---|---|---|---|---|---|
| PHF-BSA | 5 | 16 | 100° C. 10 minutes | 0.51 | Not stable |
| PHF-BSA | 7 | 16 | 100° C. 10 minutes | 0.51 | Not stable |
| BSA | 3 | — | 100° C. 10 minutes | 5.14 | Stable |
| BSA | 5 | — | 100° C. 10 minutes | 5.14 | Stable |
| PHF-BSA | 5 | — | 100° C. 10 minutes | 5.14 | Not stable |
| BSA | 7 | — | 100° C. 10 minutes | 5.14 | Stable |

Proteins, even those without catalytic activity, have a general tendency to adsorb at surfaces that are present in the same system (Murray et al., 2011 (supra)). Controls containing bovine serum albumin (BSA) at equivalent protein concentrations as the enzymes were prepared at different pH in an attempt to evaluate whether deactivated Cell and Pec offer any advantage over other proteins in functionalizing PHF particles into surface-active emulsion stabilizers.

Figure 16:
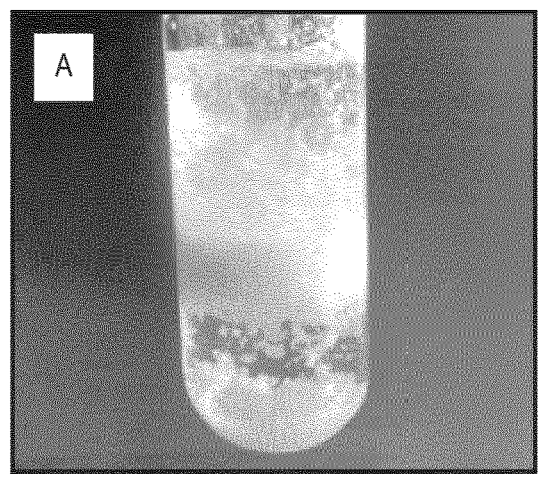
FIG. 16 shows 50% o/w emulsion stabilized with (A) heat-treated PHF-BSA and (B) heat-treated BSA alone at pH 5 after 4 weeks.

The controls containing BSA were not stable at protein concentrations equivalent to enzymatically treated samples (Table 11). Stabilization was only observed for BSA concentrations 10 times higher (5.14 mg/mL) than the enzymatically treated samples. In addition, the samples prepared with BSA were sensitive to changes in temperature and pH, which was manifested in visible precipitation after heat-treatment at pH 5 (FIG. 16A). The precipitation in BSA-stabilized emulsions at pH 5 relates to a reduced electrostatic repulsion between the proteins close to their isoelectric point (IEP, pH 5 for BSA), in combination with the increased hydrophobic interactions due to heat-treatment (Evans, Ratcliffe, Williams, 2013 *Current Opinion in Colloid & Interface Science*, 18(4), pp. 272-282 (incorporated herein by reference); McClements, 2004 *Current Opinion in Colloid & Interface Science*, 9(5), pp. 305-313 (incorporated herein by reference), Medda, Monduzzi and Salis, 2015 *Chemical Commuications.*, 51(30), pp. 6663-6666—incorporated herein by reference). The heat-treated BSA alone was able to stabilize the droplets despite becoming insoluble (FIG. 16B), but for emulsions stabilized with mixtures of PHF and BSA at pH 5, the precipitation ultimately led to emulsion destabilization after one week (FIG. 16A).

The Pickering mechanism observed for enzymatically treated PHF may be preconditioned by a particle size reduction through the catalytic action of enzymes, which produces particles small enough (<30 μm) to adsorb at the interface. Surface-active Pickering particles were not produced when PHF were incubated together with BSA, mainly due to the lack of particle reduction and maybe also due to the lower affinity of BSA to PHF, compared to enzymes. Results from this study indicate the potential use of enzyme's affinity to substrate as a new strategy to create food-grade functional protein-carbohydrate complexes.

Conclusions 3.1 Conclusion

Enzymatically Treated PHF as o/w Pickering Emulsion Stabilizers

The effects of commercial pectinases and cellulases at 1169-3682.2 U/g PHF were a significant particle size reduction (from 87.2 to <30 μm) and generation of surface active sites such that particles were able to adsorb at the o/w interface, thereby acting as o/w Pickering emulsion stabilizers. O/w emulsions (50% v/v oil) prepared with low concentrations of both treated PHF (0.4% w/v) and enzyme (0.01% w/v) creamed, yet the creamed oil droplets (10-500 μm) were stable against coalescence over a wide range of pH (3.0-8.0) for at least four weeks.

Without wishing to be bound by theory the functional properties of these modified PHF accrued mainly from altering the native form of the enzymes added and their interactions with small PHF-particles, and not from the exposure of hydrophobic polymer moieties at the PHF-particle surface, as was initially the hypothesis of this study. Two interesting observations were made with regard to the stabilization properties of enzymatically treated PHF:

1. Fibre-active enzymes present in the dispersion became excellent emulsifiers upon denaturation, which can be attributed to the exposure of hydrophobic groups at the surface due to protein unfolding.
2. Interactions between these enzymes and small degraded PHF result in the formation of food-compatible Pickering-stabilizers.

In general, it is shown that the PHF particles on their own do not exhibit surface-activity, but functionalised PHF particles in combination with the denatured enzymes do exhibit surface-activity and act as Pickering particles. The functionalised PHF particles may form PHF-enzyme-complexes that act as Pickering particles. The enzymes may remain attached to the PHF surface serving as a proteinaceous structural component that anchors the particle to the o/w interface.

The fabrication pathway of surface-active particles through protein-particle interaction could not be generalized to other proteins like BSA at the given conditions.

Example 2—Low-Cellulosic Plant Fibres

Different plant fibres were tested, namely pea hull fibres (PHF), pectin-rich apple fibre non-cellulosic wheat fibre, were tested.

The same enzymes (Pectinex and Cellculast) an different enzymes (a protease [Alcalase® available from Sigma-Aldrich—now Merck], an α-amylase [Mats L Classic available from DSM], & a xylanase) were tested for their ability to functionalize these fibre particles and for the ability of enzyme treated fibre particles to stabilize emulsion oil droplets.

Incubation conditions: 10% TS, pH 5, 50° C., 16 h, enzyme dose: 51.4 mg protein/g fibre. Temperature and pH correspond to optimum conditions for all enzymes. Enzyme inactivation: Boiling for 10 mins.

"Emulsion stability": 1 mL enzymatically treated fibres (10% w/w, in buffer pH 5, unless stated otherwise) is added to 10 mL water phase pH 5 of 50% o/w emulsions. Emulsion is manually shaken for 10 seconds. Stability is assessed on the resistance of large, creamed oil droplets to coalesce for 9 weeks.

Results

Reference: 50% v/v o/w emulsions with 0.4% w/v pea hull fibres (PHF) treated with Pectinex and Celluclast (Pec+Cell)

PHF Treated with Non-Fibre Degrading Enzymes:

Emulsions with 0.4% w/v PHF treated with non-fibre degrading enzymes (Alcalase® 2.4 L, MATS L CLASSIC (DSM)) or deactivated enzymes alone were unstable (FIG. 21). Surface activity of enzymes alone after heat treatment however is a key requirement to enable functionalization, whatever the main activity of the enzyme is.

Figure 22:
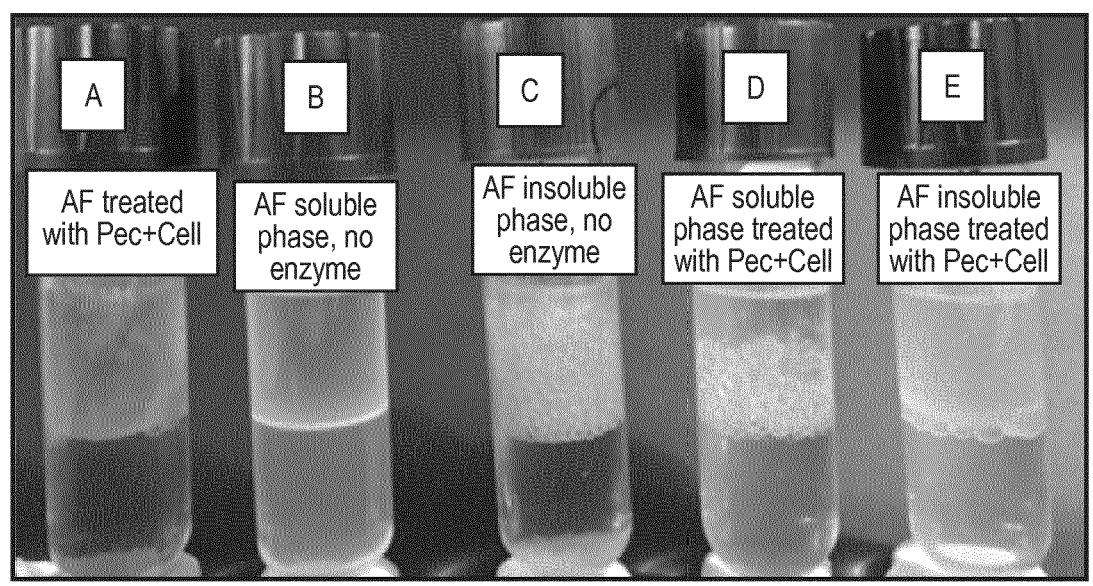
FIG. 22 shows 50% v/v o/w emulsions stabilized with 0.4% w/v AF-Pec+Cell and controls.
Figure 23:
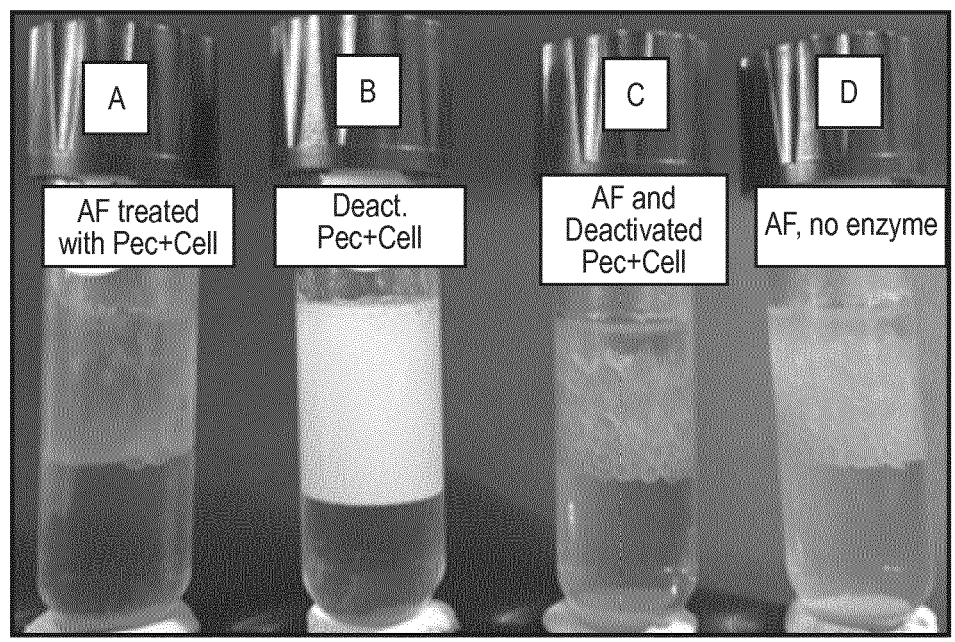
FIG. 23 shows 50% v/v o/w emulsions stabilized with 0.4% w/v AF and controls.

Apple Fibres Treated with Pectinex and Celluclast:

Emulsions with 0.4% w/v apple fibres treated with Pectinex and Celluclast (AF-Pec+Cell) were unstable (FIG. 22A and FIG. 23A). However, all controls [only deactivated enzyme (FIG. 23B), Apple Fibre (AF) with deactivated enzymes (FIG. 23C) or only AF (FIG. 3D)] were stable, suggesting that certain compounds present in AF interfere with the active enzymes and change their functionality during incubation.

The stabilizing effect in samples with AF alone was believed to originate from the soluble pectin fraction in AF. The fact that the stabilizing effect was absent for treated samples was attributed to the fact that the pectins were degraded by pectinases.

Further analyses showed that the stabilizing agent is located in the insoluble phase (FIG. 22C) of hydrated AF, and that it is also the insoluble phase that contains the functionality-compromising compounds (FIG. 22E). Heat treating (boiling, 15 minutes) the AF before enzymatic reaction to deactivate potential native proteases in AF did not change the outcome. The soluble phase of AF dispersions did not stabilize emulsions (FIG. 22B), but when treated with Pec+Cell, some stable droplets were observed (FIG. 22D), which can be attributed to the presence of denatured, surface-active Pec+Cell.

Figure 24:
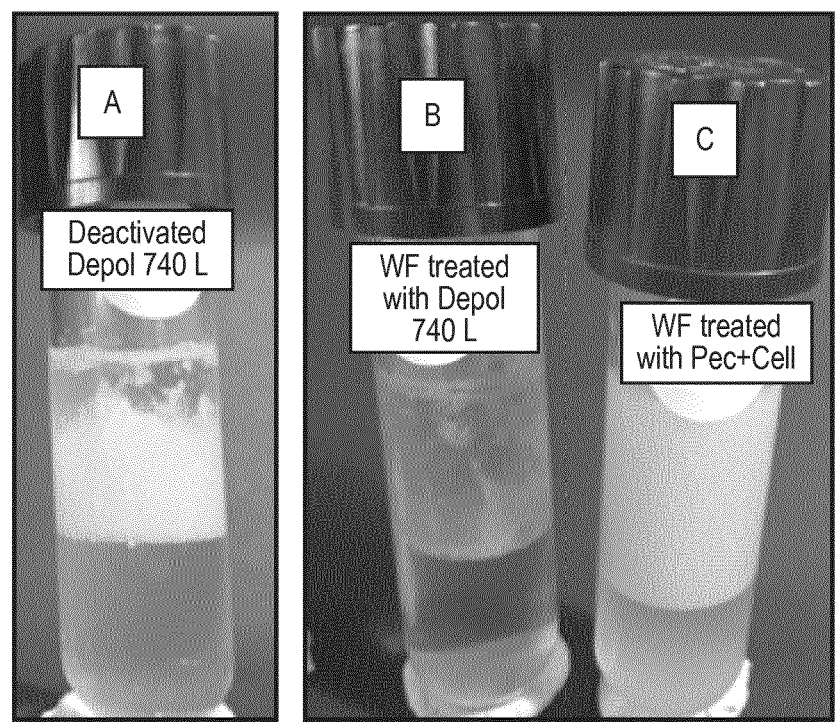
FIG. 24 shows 50% v/v o/w emulsions stabilized with 0.4% w/v WF treated with D740 L and controls
Figure 25:
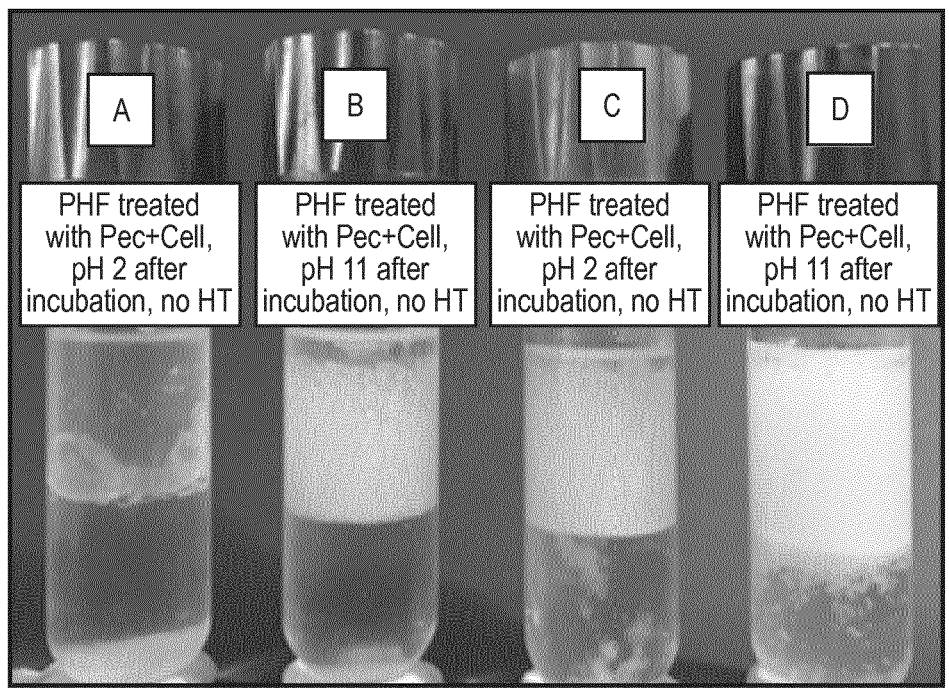
FIG. 25 shows 50% v/v o/w emulsions stabilized with 0.4% w/v PHF adjusted to different pH before enzyme inactivation. HT: heat treatment

Wheat Fibres Treated with Depol 740 L:

Emulsions with 0.4% w/v wheat fibres (WF) treated with a Feruloyl esterase, namely Depol 740 L (D740 L) (a beta-glucanase with feruloyl esterase and xylanase side activities sold by Biocatalysts UK). were unstable (FIG. 24B), whereas controls with deactivated D740 L were stable (FIG. 24A). As previously observed for AF-Pec+Cell, certain compounds in WF seem to inhibit surface-activity of D740 L. However, when D740 L was replaced by Pec+Cell, this inhibitory effect was absent (FIG. 24C), indicating that the inhibition is enzyme/substrate specific.

Pea Hull Fibres Treated with Pec+Cell, pH Adjustment Before Heat Treatment

An additional experiment was performed with PHF and Pec+Cell, where pH was adjusted to 2.0 or 11.0 before heat treatment (HT), to see whether this changes enzyme-particle interaction and whether such particles are still able to stabilize oil droplets.

Regardless the pH before HT, stable oil droplets were obtained. For PHF dispersions adjusted to pH 11.0, surface activity was achieved without heat treatment, most likely due to pH induced denaturation. This was not the case for samples adjusted to pH 2.0 before HT.

Conclusions

Functionalization pathway of PHF-Pec+Cell was not observed with apple fibres (high pectin fibres) or wheat fibres (low or no cellulose containing fibres) or with enzymes that were not capable of degrading the dietary fibre.

Example 3—Kitchen Prototypes: Liquid Coffee Creamers & Sensory

Preliminary sensory trials showed good acceptance of liquid coffee creamers prepared with enzymatically treated PHF as an alternative emulsifiers to Na-Caseinate.

The enzymatically treated PHF (PHF-Pec+Cell) were tested in a selected food prototype. Liquid coffee creamers were chosen as a model system to assess the potential of enzymatically treated (functionalised) pea hull fibres (and denatured enzyme) as emulsion stabilizers and benchmark their stabilizing performance against conventional emulsifier sodium caseinate. A simplified recipe for a model liquid creamer is shown in Table 12.

Figure 17:
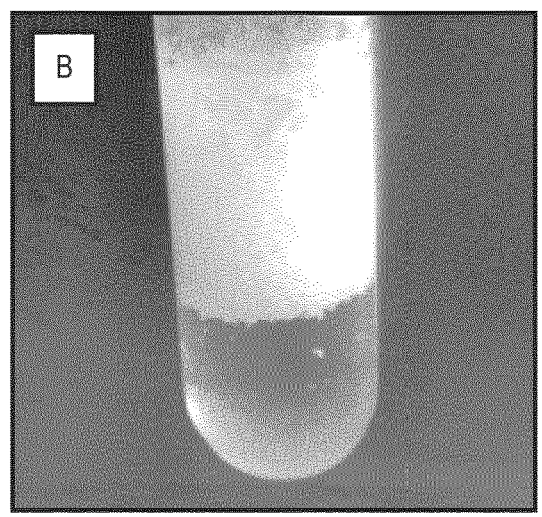
FIG. 17 shows samples of o/w emulsions prepared with varying oil:water ratios.
Figure 17:
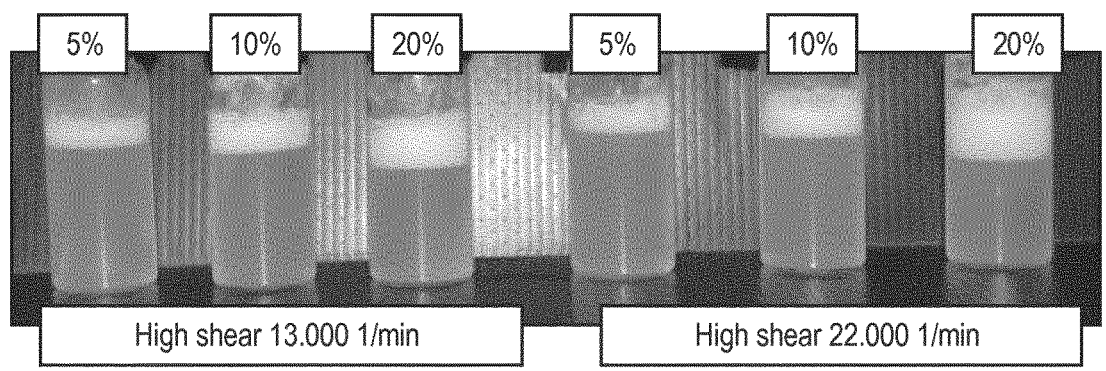
Figure 18:
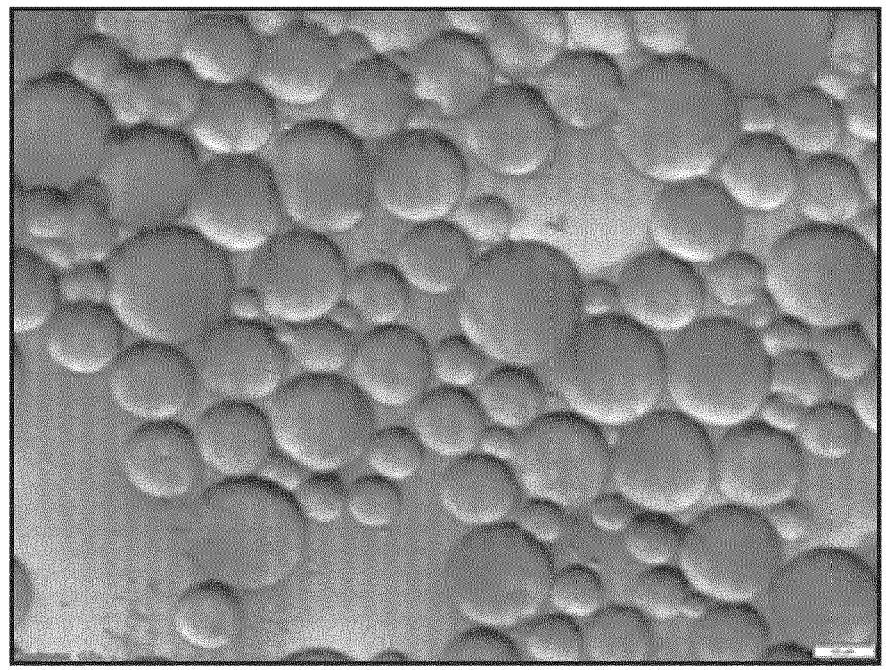
FIG. 18 shows an optical micrograph of 20% w/o emulsion high-sheared at 22,000 1/min. Scale bar: 50 μm.

Preliminary trials were performed by preparing emulsions with constant amount of treated PHF (0.5 mL per 10 mL emulsion) and varying oil:water ratio. Emulsions were mixed with an Ultra-turax at two different shear rates (13,000 and 22,000 1/min). The emulsion destabilized in a two-layer system, the height of the creaming layer being in proportion to the volume fraction of oil. Because of the homogenization step at higher shear rates, the droplet size decreased significantly compared to formerly prepared 50% o/w emulsions obtained by manual shaking, as shown in FIG. 17. Droplet size remained in the range of 50 µm. These relatively big oil droplets are thought to be a favourable trait in mouthfeel/mouthcoating enhancement (FIG. 18).

Next, five different formulations were produced in the experimental kitchen by partially or fully replacing Na-Caseinate in liquid creamers, which is the primary emulsifier used currently, with varying concentrations of PHF (Table 12).

TABLE 12

Formulations of liquid creamer prototypes and reference.

| Code | A | B | C | D | E | F |
|---|---|---|---|---|---|---|
| Sample | Reference | Control | 100% caseinate replacement 0.1 g PHF[a]/oil | 100% caseinate replacement gPHF[a]/g oil | 100% caseinate 1 g replacement gPHF[a]/g oil | 50% caseinate 7.3 replacement 1 g PHF[a]/g oil |
| Sugar (g) | 30 | 30 | 30 | 30 | 30 | 30 |
| Oil (g) | 8.4 | 8.4 | 8.4 | 8.4 | 8.4 | 8.4 |
| Sodium Caseinate (g) | 0.9 | 0.9 | 0 | 0 | 0 | 0.45 |
| Dipotassium phosphate (g) | 0.4 | 0.4 | 0.4 | 0.4 | 0.4 | 0.4 |
| PHF (g) | 0 | 0 | 0.84 | 8.4 | 61.2 | 4.2 |
| Water (g) | 60.3 | 60.3 | 60.36 | 52.8 | 0 | 56.55 |
| Total (g) | 100 | 100 | 100 | 100 | 100 | 100 |

[a] Here, PHF refers PHF − Pec + Cell 8 panelists were invited for a sensory evaluation with the aim to obtain information about stability, taste, mouthfeel and appearance of liquid creamers stabilized with enzymatically treated PHF in accordance with the invention compared to the reference. Panelists were given five different samples and one control which was again the reference, to assess the validity of this trial.

Figure 19:
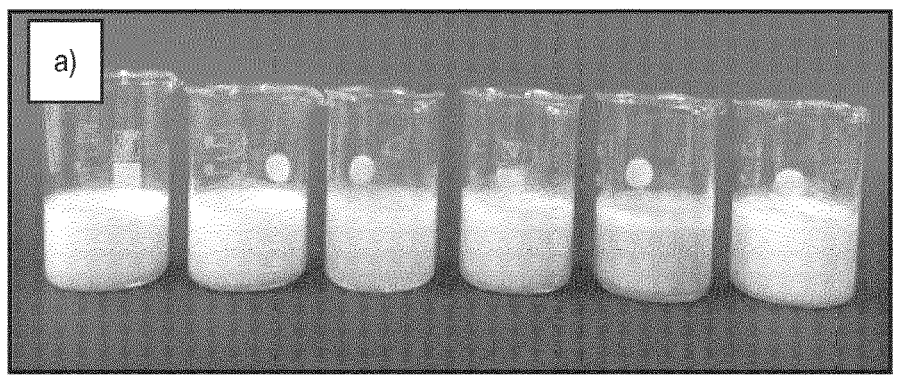
FIG. 19 shows liquid creamers prepared according to table 12. From left to right: Creamer A, B, C, D, E and F. a) Right after preparation and b) 30 minutes after preparation.
Figure 19:
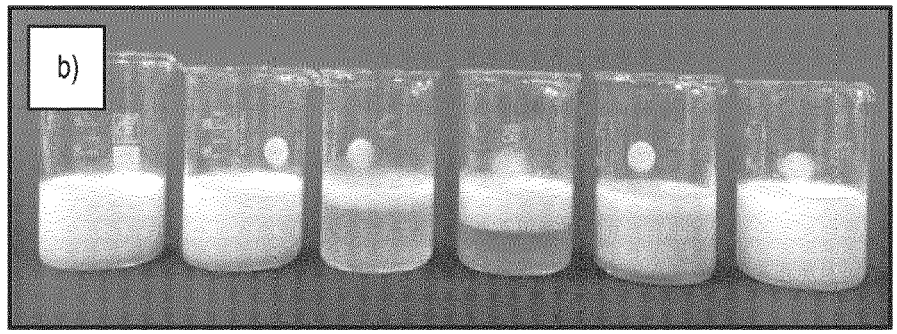

Pictures of the creamers are depicted in FIG. 19. Replacement of Na-Caseinate with PHF resulted in a slightly beige colour. For all the samples, creaming occurred, and was most pronounced for samples C and D. The 50:50 PHF:Na-Caseinate blend masked all adverse effects on appearance.

Figure 20:
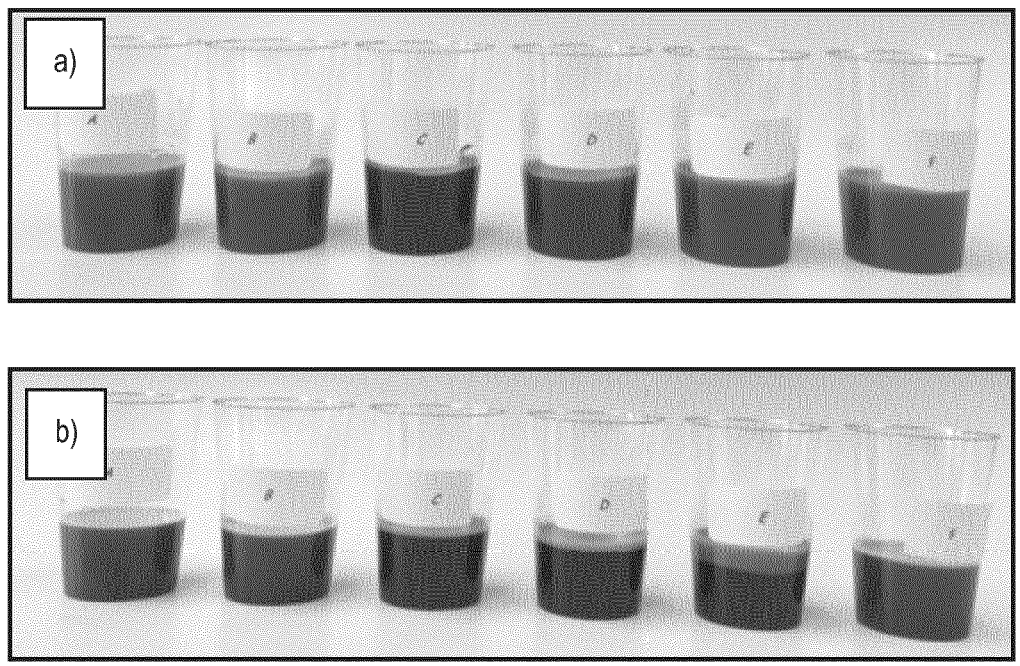
FIG. 20 shows coffee mixed with liquid creamers in a 1:6 ratio. From left to right: Creamer A, B, C, D, E, F. a) Right after preparation and b) 30 minutes after preparation.

The same held for samples that were prepared with coffee and creamer (FIG. 20).

Panelists' comments indicate that liquid creamers prepared with PHF showed overall good sensory acceptance compared to the reference.

The main advantages of liquid creamers stabilized with PHF would be the substitution of conventional emulsifiers by fibres as a clean-label alternative. A functional advantage is that bigger oil droplets are expected that would enhance mouth feeling. Another advantage is the incomplete surface coverage that favours increased mass transfer between oil and water phase and could catch aggressive lipophilic aroma compounds (in for example coffee).

Example 4: Technical Trials "Solution Pea Hulls"

Kitchen scale trials were performed on chocolate mousse to see the extent to which treated PHF could allow a partial/total substitution of artificial emulsifiers and/or gelatin.

| | | | |
|---|---|---|---|
| Recipe Reference | Fresh milk 36.1 g fat /L | 63.50 | 0.635 |
| | Cream 30-32% fat | 8.75 | 0.088 |
| | Liquid milk chocolate (incl. Sunflower lecithin) | 7.00 | 0.070 |
| | Cristal sugar | 11.40 | 0.114 |
| | Skim milk powder Medium Heat | 2.00 | 0.020 |
| | Bovine Gelatin 150 bloom | 1.05 | 0.011 |
| | Lactic acid ester (Lactem PQ 22-K) | 0.50 | 0.005 |
| | Caramel | 1.00 | 0.010 |
| | Cocoa powder (10-12% cocoa butter) | 3.10 | 0.031 |
| | Cocoa powder (20-22% cocoa butter) | 1.70 | 0.017 |
| | Treated pea hulls | 0.00 | 0.000 |
| | Final product (%) | 100 | 1.000 |
| Recipe 1 | Fresh milk 36.1 g fat /L | 64.15 | 0.642 |
| | Cream 30-32% fat | 9.25 | 0.093 |
| | Liquid milk chocolate (incl. Sunflower lecithin) | 7.00 | 0.070 |
| | Cristal sugar | 11.40 | 0.114 |
| | Skim milk powder Medium Heat | 2.00 | 0.020 |
| | Bovine Gelatin 150 bloom | 0.00 | 0.000 |
| | Lactic acid ester (Lactem PQ 22-K) | 0.00 | 0.000 |
| | Caramel | 1.00 | 0.010 |
| | Cocoa powder (10-12% cocoa butter) | 3.10 | 0.031 |
| | Cocoa powder (20-22% cocoa butter) | 1.70 | 0.017 |
| | Treated pea hulls | 0.40 | 0.004 |
| | Final product (%) | 100 | 1.000 |
| Recipe 2 | Fresh milk 36.1 g fat /L | 64.15 | 0.642 |
| | Cream 30-32% fat | 8.75 | 0.088 |
| | Liquid milk chocolate (incl. Sunflower lecithin) | 7.00 | 0.070 |
| | Cristal sugar | 11.40 | 0.114 |
| | Skim milk powder Medium Heat | 2.00 | 0.020 |
| | Bovine Gelatin 150 bloom | 0.00 | 0.000 |

|  |  | | |
|---|---|---:|---:|
| | Lactic acid ester (Lactem PQ 22-K) | 0.50 | 0.005 |
| | Caramel | 1.00 | 0.010 |
| | Cocoa powder (10-12% cocoa butter) | 3.10 | 0.031 |
| | Cocoa powder (20-22% cocoa butter) | 1.70 | 0.017 |
| | Treated pea hulls | 0.40 | 0.004 |
| | Final product (%) | 100 | 1.000 |
| Recipe 3 | Fresh milk 36.1 g fat /L | 63.95 | 0.640 |
| | Cream 30-32% fat | 8.95 | 0.090 |
| | Liquid milk chocolate (incl. Sunflower lecithin) | 7.00 | 0.070 |
| | Cristal sugar | 11.40 | 0.114 |
| | Skim milk powder Medium Heat | 2.00 | 0.020 |
| | Bovine Gelatin 150 bloom | 0.50 | 0.005 |
| | Lactic acid ester (Lactem PQ 22-K) | 0.00 | 0.000 |
| | Caramel | 1.00 | 0.010 |
| | Cocoa powder (10-12% cocoa butter) | 3.10 | 0.031 |
| | Cocoa powder (20-22% cocoa butter) | 1.70 | 0.017 |
| | Treated pea hulls | 0.40 | 0.004 |
| | Final product (%) | 100 | 1.000 |
| Recipe 4 | Fresh milk 36.1 g fat /L | 63.50 | 0.635 |
| | Cream 30-32% fat | 8.75 | 0.088 |
| | Liquid milk chocolate (incl. Sunflower lecithin) | 7.00 | 0.070 |
| | Cristal sugar | 11.40 | 0.114 |
| | Skim milk powder Medium Heat | 2.15 | 0.022 |
| | Bovine Gelatin 150 bloom | 0.50 | 0.005 |
| | Lactic acid ester (Lactem PQ 22-K) | 0.50 | 0.005 |
| | Caramel | 1.00 | 0.010 |
| | Cocoa powder (10-12% cocoa butter) | 3.10 | 0.031 |
| | Cocoa powder (20-22% cocoa butter) | 1.70 | 0.017 |
| | Treated pea hulls | 0.40 | 0.004 |
| | Final product (%) | 100 | 1.000 |
| Recipe 5 | Fresh milk 36.1 g fat /L | 63.50 | 0.635 |
| | Cream 30-32% fat | 8.85 | 0.089 |
| | Liquid milk chocolate (incl. Sunflower lecithin) | 7.00 | 0.070 |
| | Cristal sugar | 11.40 | 0.114 |
| | Skim milk powder Medium Heat | 2.00 | 0.020 |
| | Bovine Gelatin 150 bloom | 1.05 | 0.011 |
| | Lactic acid ester (Lactem PQ 22-K) | 0.00 | 0.000 |
| | Caramel | 1.00 | 0.010 |
| | Cocoa powder (10-12% cocoa butter) | 3.10 | 0.031 |
| | Cocoa powder (20-22% cocoa butter) | 1.70 | 0.017 |
| | Treated pea hulls | 0.40 | 0.004 |
| | Final product (%) | 100 | 1.000 |
| Recipe 6 | Fresh milk 36.1 g fat /L | 63.50 | 0.635 |
| | Cream 30-32% fat | 9.25 | 0.093 |
| | Liquid milk chocolate (incl. Sunflower lecithin) | 7.00 | 0.070 |
| | Cristal sugar | 11.40 | 0.114 |
| | Skim milk powder Medium Heat | 3.05 | 0.031 |
| | Bovine Gelatin 150 bloom | 0.00 | 0.000 |
| | Lactic acid ester (Lactem PQ 22-K) | 0.00 | 0.000 |
| | Caramel | 1.00 | 0.010 |
| | Cocoa powder (10-12% cocoa butter) | 3.10 | 0.031 |
| | Cocoa powder (20-22% cocoa butter) | 1.70 | 0.017 |
| | Treated pea hulls | 0.00 | 0.000 |
| | Final product (%) | 100 | 1.000 |

| | OR (%) | pH | Process | Weight/cup | Comments |
|---|---|---|---|---|---|
| Recipe 1 | 62 | 6.61 | 15 min/ 2nd speed | 60 g | Slight whipping, small collapse of the mousse. Whipped aspect only visible on the surface Dark colour. Not very stable |
| Recipe 2 | 202 | 6.60 | 15 min/ 2nd speed | 40 g | Liquid texture before whipping at 4° C. Quick whipping. Aerated texture. Not very stable Slight collapse during dosing No bubbles. Fits quickly to cup's contours. Light colour |
| Recipe 3 | 61 | 6.58 | 15 min/ 2nd speed | 60 g | Liquid texture Difficult to whip. Whipping starts after 10 minutes. |

| | | | | | |
|---|---|---|---|---|---|
| Recipe 4 | 232 | 6.55 | 15 min/ 2nd speed | 40 g | Lack of stability and lack of cohesion of the ingredients<br>Ascent of air bubbles at dosing<br>Dark colour<br>Whipping behavior similar to the one of recipe No 2<br>Quick whipping<br>Firmer texture compared to recipe No 2 - small sculpted dome at dosing<br>Slight collapse of the mousse<br>Light colour (milk chocolate mousse colour) |
| Recipe 5 | 68 | 6.54 | 15 min/ 2nd speed | 60 g | Firm texture before whipping (when taken out of the fridge)<br>Difficult to whip. Collapsed mousse. Very dark colour. |
| Recipe 6 | 68 | 6.52 | 15 min/ 2nd speed | 60 g | No whipping<br>Very liquid texture before whipping<br>Mousse texture only at the surface. Liquid texture at the bottom of the cup. |

OR = overrun values

Figure 26:
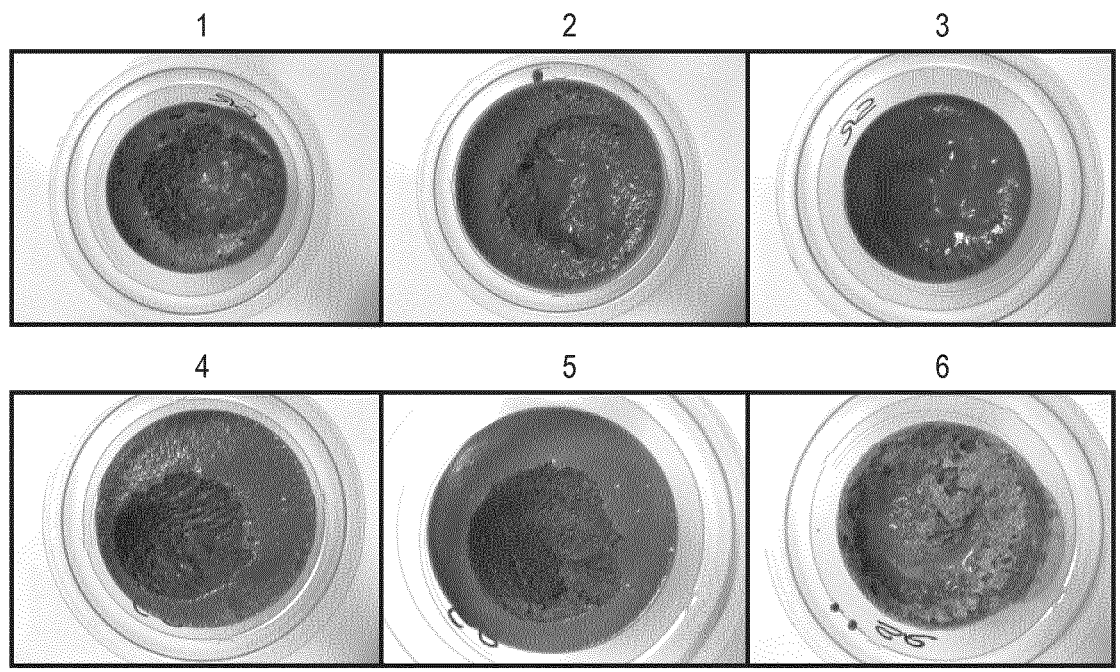
FIG. 26 shows pictures of chocolate mousse resulting from kitchen scale trials (top view)
Figure 27:
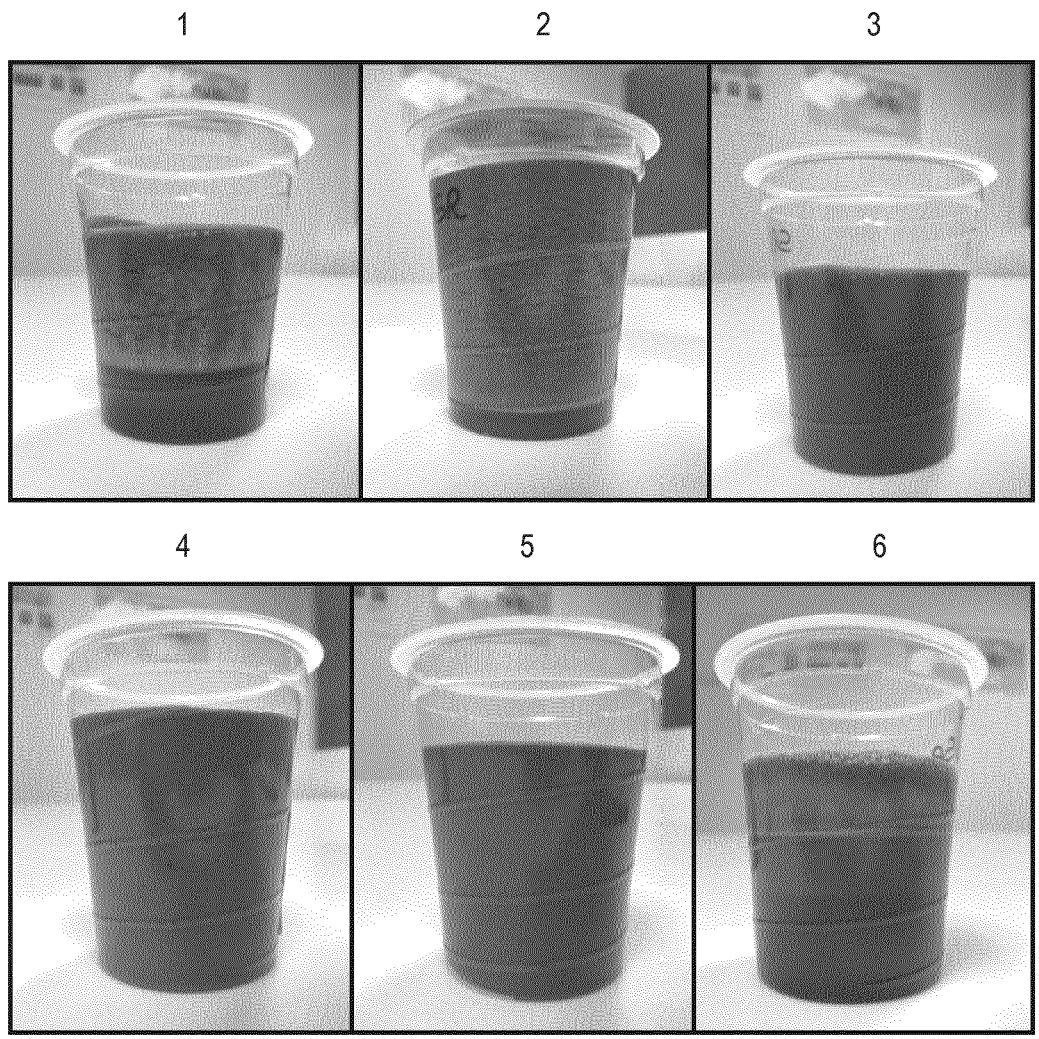
FIG. 27 shows pictures of chocolate mousse resulting from kitchen scale trials (front view)

Pictures of the chocolate mousse recipes 1 to 6 during shelf-life are shown from the top after removal of a spoonful of mousse (FIG. 26) and from the front (FIG. 27).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A process for forming a functionalised and amphiphilic dietary fiber, the process comprising:
  admixing an enzyme and an aqueous suspension of dietary fiber selected from the group consisting of pea hull fiber, pulse hulls, bamboo fiber, cocoa fibers and coffee fibers, wherein the dietary fiber has a $D_{50}$ particle size distribution of less than 30 microns after degradation by the enzyme, and the dietary fiber comprises less than 25 wt. % soluble fibers and at least 40 wt. % cellulose; and
  denaturing the enzyme to form the functionalised and amphiphilic dietary fiber with the denatured enzyme adsorbed on a surface of the functionalised and amphiphilic dietary fiber.

2. The process according to claim 1 further comprising hydrolysing the dietary fiber with the enzyme for a period up to 24 hours after the admixing of the enzyme and the aqueous suspension of the dietary fiber.

3. The process according to claim 1, wherein the enzyme comprises one or more enzymes selected from the group consisting of endo-1,4-β-glucanase, cellobiohydrolase, β-glucosidase, endo-polygalacturonase, exo-polygalacturonase, pectin-methyl-esterase, endo-pectate lyase, exo-pectate lyase and pectin lyase.

4. The process according to claim 1, wherein the dietary fiber comprises pea hull fiber.

* * * * *

SEQUENCE LISTING

```
<160> NUMBER OF SEQ ID NOS: 3

<210> SEQ ID NO 1
<211> LENGTH: 471
<212> TYPE: PRT
<213> ORGANISM: Trichoderma reesei
<220> FEATURE:
<223> OTHER INFORMATION: Cellobiohydrolase

<400> SEQUENCE: 1

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
        50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
        130                 135                 140

Ala Thr Ala Ala Ala Ala Val Ala Lys Val Pro Ser Phe Met Trp Leu
```

```
               145                 150                 155                 160
Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
                180                 185                 190

Tyr Asp Leu Pro Asp Arg Asp Cys Ala Ala Leu Ala Ser Asn Gly Glu
                195                 200                 205

Tyr Ser Ile Ala Asp Gly Gly Val Ala Lys Tyr Lys Asn Tyr Ile Asp
                210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
                260                 265                 270

Ala Val Thr Gln Leu Asn Leu Pro Asn Val Ala Met Tyr Leu Asp Ala
                275                 280                 285

Gly His Ala Gly Trp Leu Gly Trp Pro Ala Asn Gln Asp Pro Ala Ala
                290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
                340                 345                 350

Tyr Ile His Ala Ile Gly Arg Leu Leu Ala Asn His Gly Trp Ser Asn
                355                 360                 365

Ala Phe Phe Ile Thr Asp Gln Gly Arg Ser Gly Lys Gln Pro Thr Gly
                370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
                420                 425                 430

Pro Arg Phe Asp Ser His Cys Ala Leu Pro Asp Ala Leu Gln Pro Ala
                435                 440                 445

Pro Gln Ala Gly Ala Trp Phe Gln Ala Tyr Phe Val Gln Leu Leu Thr
                450                 455                 460

Asn Ala Asn Pro Ser Phe Leu
465                 470

<210> SEQ ID NO 2
<211> LENGTH: 513
<212> TYPE: PRT
<213> ORGANISM: Trichoderma reesei
<220> FEATURE:
<223> OTHER INFORMATION: Cellobiohydrolase

<400> SEQUENCE: 2

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
                20                  25                  30

Trp Gln Lys Cys Ser Ser Gly Gly Thr Cys Thr Gln Gln Thr Gly Ser
```

```
                35                  40                  45
Val Val Ile Asp Ala Asn Trp Arg Trp Thr His Ala Thr Asn Ser Ser
 50                  55                  60

Thr Asn Cys Tyr Asp Gly Asn Thr Trp Ser Ser Thr Leu Cys Pro Asp
 65                  70                  75                  80

Asn Glu Thr Cys Ala Lys Asn Cys Cys Leu Asp Gly Ala Ala Tyr Ala
                 85                  90                  95

Ser Thr Tyr Gly Val Thr Thr Ser Gly Asn Ser Leu Ser Ile Gly Phe
                100                 105                 110

Val Thr Gln Ser Ala Gln Lys Asn Val Gly Ala Arg Leu Tyr Leu Met
                115                 120                 125

Ala Ser Asp Thr Thr Tyr Gln Glu Phe Thr Leu Leu Gly Asn Glu Phe
                130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
                195                 200                 205

Trp Glu Pro Ser Ser Asn Asn Ala Asn Thr Gly Ile Gly Gly His Gly
                210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
                260                 265                 270

Cys Asp Pro Asp Gly Cys Asp Trp Asn Pro Tyr Arg Leu Gly Asn Thr
                275                 280                 285

Ser Phe Tyr Gly Pro Gly Ser Ser Phe Thr Leu Asp Thr Thr Lys Lys
                290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
                340                 345                 350

Ala Glu Phe Gly Gly Ser Ser Phe Ser Asp Lys Gly Gly Leu Thr Gln
                355                 360                 365

Phe Lys Lys Ala Thr Ser Gly Gly Met Val Leu Val Met Ser Leu Trp
                370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
                420                 425                 430

Val Thr Phe Ser Asn Ile Lys Phe Gly Pro Ile Gly Ser Thr Gly Asn
                435                 440                 445

Pro Ser Gly Gly Asn Pro Pro Gly Gly Asn Arg Gly Thr Thr Thr Thr
                450                 455                 460
```

```
Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
                500                 505                 510

Leu

<210> SEQ ID NO 3
<211> LENGTH: 339
<212> TYPE: PRT
<213> ORGANISM: Aspergillus aculeatus
<220> FEATURE:
<223> OTHER INFORMATION: Polygalacturonase

<400> SEQUENCE: 3

Ala Thr Thr Cys Thr Phe Ser Gly Ser Asn Gly Ala Ser Ser Ala Ser
1               5                   10                  15

Lys Ser Lys Thr Ser Cys Ser Thr Ile Val Leu Ser Asn Val Ala Val
                20                  25                  30

Pro Ser Gly Thr Thr Leu Asp Leu Thr Lys Leu Asn Asp Gly Thr His
            35                  40                  45

Val Ile Phe Ser Glu Thr Thr Phe Gly Tyr Lys Glu Trp Ser Gly
50                  55                  60

Pro Leu Ile Ser Val Ser Gly Ser Asp Leu Thr Ile Thr Gly Ala Ser
65                  70                  75                  80

Gly His Ser Ile Asn Gly Asp Gly Ser Arg Trp Trp Asp Gly Glu Gly
                85                  90                  95

Gly Asn Gly Gly Lys Thr Lys Pro Lys Phe Ala Ala His Ser Leu
            100                 105                 110

Thr Asn Ser Val Ile Ser Gly Leu Lys Ile Val Asn Ser Pro Val Gln
            115                 120                 125

Val Phe Ser Val Ala Gly Ser Asp Tyr Leu Thr Leu Lys Asp Ile Thr
130                 135                 140

Ile Asp Asn Ser Asp Gly Asp Asn Gly His Asn Thr Asp Ala
145                 150                 155                 160

Phe Asp Ile Gly Thr Ser Thr Tyr Val Thr Ile Ser Gly Ala Thr Val
                165                 170                 175

Tyr Asn Gln Asp Asp Cys Val Ala Val Asn Ser Gly Glu Asn Ile Tyr
                180                 185                 190

Phe Ser Gly Gly Tyr Cys Ser Gly Gly His Gly Leu Ser Ile Gly Ser
            195                 200                 205

Val Gly Gly Arg Ser Asp Asn Thr Val Lys Asn Val Thr Phe Val Asp
210                 215                 220

Ser Thr Ile Ile Asn Ser Asp Asn Gly Val Arg Ile Lys Thr Asn Ile
225                 230                 235                 240

Asp Thr Thr Gly Ser Val Ser Asp Val Thr Tyr Lys Asp Ile Thr Leu
            245                 250                 255

Thr Ser Ile Ala Lys Tyr Gly Ile Val Gln Gln Asn Tyr Gly Asp
            260                 265                 270

Thr Ser Ser Thr Pro Thr Thr Gly Val Pro Ile Thr Asp Phe Val Leu
        275                 280                 285

Asp Asn Val His Gly Ser Val Val Ser Ser Gly Thr Asn Ile Leu Ile
    290                 295                 300
```

-continued

```
Ser Cys Gly Ser Gly Ser Cys Ser Asp Trp Thr Trp Thr Asp Val Ser
305                 310                 315                 320

Val Ser Gly Gly Lys Thr Ser Ser Lys Cys Thr Asn Val Pro Ser Gly
            325                 330                 335

Ala Ser Cys
```